(12) United States Patent
Bednar et al.

(10) Patent No.: US 8,617,563 B2
(45) Date of Patent: Dec. 31, 2013

(54) ANTICHLAMYDIAL AGENTS

(75) Inventors: Maria M. Bednar, Durham, NC (US); Ine Jorgensen, Durham, NC (US); Dewey G. McCafferty, Chapel Hill, NC (US); Raphael H. Valdivia, Carrboro, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 13/361,706

(22) Filed: Jan. 30, 2012

(65) Prior Publication Data

US 2012/0263745 A1 Oct. 18, 2012

Related U.S. Application Data

(60) Provisional application No. 61/474,301, filed on Apr. 12, 2011.

(51) Int. Cl.
*A61K 39/00* (2006.01)
*C07K 1/00* (2006.01)
*C07K 2/00* (2006.01)

(52) U.S. Cl.
USPC .................. 424/185.1; 530/300; 530/350

(58) Field of Classification Search
None
See application file for complete search history.

(56) References Cited

U.S. PATENT DOCUMENTS

2008/0124338 A1  5/2008  Li et al.
2009/0098165 A1*  4/2009  Arulanandam et al. ... 424/263.1

OTHER PUBLICATIONS

Abdul-Sater, A.A., et al., "Inflammasome-dependent caspase-1 activation in cervical epithelial cells stimulates growth of the intracellular pathogen *Chlamydia trachomatis*" J Biol Chem 284, (2009) 26789-26796.
Adderley-Kelly, B., et al., "Chlamydia: a major health threat to adolescents and young adults" ABNF J 16, (2005) 52-55.
Arnold, R., et al., "Sequence-based prediction of type III secreted proteins" PLoS Pathog 5, (2009) e1000376.
Ausubel et al., Current Protocols in Molecular Biology, (2002) John Wiley & Sons, Somerset, NJ.
Belland, R.J., et al., "Genomic transcriptional profiling of the developmental cycle of *Chlamydia trachomatis*" Proc Natl Acad Sci USA 100, (2003) 8478-8483.
Bergsbaken, T., et al., "Macrophage activation redirects *yersinia*-infected host cell death from apoptosis to caspase-1-dependent pyroptosis" PLoS Pathog 3, (2007) e161.
Bergsbaken, T., et al., Pyroptosis: host cell death and inflammation. Nat Rev Microbiol 7, (2009) 99-109.
Bodansky, Principles of Peptide Synthesis, (1984) Springer-Verlag, Berlin.
Brennan, M.A., et al., "*Salmonella* induces macrophage death by caspase-1-dependent necrosis" Mol Microbiol 38, (2000) 31-40.
Caldwell, H.D., et al. "Purification and Piltial characterization of the major outer membrane protein of *Chlamydia trachomatis*" Infect Immun 31, (1981) 1161-1176.
Cervantes, J., et al., "Intracytosolic *Listeria monocytogenes* induces cell death through caspase-1 activation in murine macrophages" Cell Microbiol 10, (2008) 41-52.
Chen, D., et al., "Secretion of the chlamydial virulence factor CPAF requires the Sec-dependent pathway" Microbiology 156, (2010) 3031-3040.
Christian, J.G., et al., "Cleavage of the Nf-{kappa}B-family protein p65/RelA by the chlamydial protease chlamydial protease-like activity factor (CPAF) impairs pro-inflammatory signalling in cells Infected with chlamydiae" J Biol Chem, (2010).
Clifton, D.R., et al., "A chlamydial type III translocated protein is tyrosine-phosphorylated at the site of entry and associated with recruitment of actin" Proc Natl Acad Sci USA 101, (2004) 10166-10171.
Darzynkiewicz, Z., et al., "Fluorochrome-labeled inhibitors of caspases: convenient in vitro and in vivo markers of apoptotic cells for cytometric analysis" Methods Mol Biol 682, (2011) 103-114.
Dong, F., et al., "Cleavage of host keratin 8 by a *Chlamydia*-secreted protease" Infect Immun 72, (2004) 3863-3868.
Fields, K.A.,et al., "The chlamydial inclusion: escape from the endocytic pathway" Annu Rev Cell Dev Biol 18, (2002) 221-245.
Galluzzi, L., et al., "Guidelines for the use and interpretation of assays for monitoring cell death in higher eukaryotes" Cell Death Differ 16, (2009) 1093-1107.
Greene, W., et al., "*Chlamydia*-infected cells continue to undergo mitosis and resist induction of apoptosis" Infect Immun 72, (2004) 451-460.
Gurcel, L., et al., "Caspase-1 activation of lipid metabolic pathways in response to bacterial pore-forming toxins promotes cell survival" Cell 126, (2006) 1135-1145.
Hower, S., et al., "Evidence that CT694 is a novel *Chlamydia trachomatis* T3S substrate capable of functioning during invasion or early cycle development" Mol Microbiol 72, (2009) 1423-1437.
Hu, V. H., et al., "Epidemiology and control of trachoma: systematic review" In Tropical Medicine & International Health, (2010) pp. 673-691.
Huang, et al., "Structural Basis for Activation and Inhibition of the Secreted *Chlamydia* Protease CPAF" Cell Host & Microbe, 4:529-542 (2008).

(Continued)

*Primary Examiner* — Albert Navarro
(74) *Attorney, Agent, or Firm* — Michael Best & Friedrich LLP

(57) ABSTRACT

An antichlamydial agent comprising an inhibitor of Chlamydial Protease-like Activity Factor (CPAF). The inhibitor of CPAF can comprise a CPAF inhibitory segment and can optionally include one or more additional residues or domains. Also provided are compositions comprising an inhibitor of CPAF, methods of identifying an inhibitor of CPAF, and methods of treating a *Chlamydia* infection in a subject comprising administering an inhibitor of CPAF or a composition comprising an inhibitor of CPAF to the subject.

15 Claims, 21 Drawing Sheets

(56) References Cited

OTHER PUBLICATIONS

Jesenberger, V., et al., *Salmonella*-induced caspase-2 activation in macrophages: a novel mechanism in pathogen-mediated apoptosis. J Exp Med 192, (2000) 1035-1046.

Jewett, T.J., et al., "*Chlamydia trachomatis* tarp is phosphorylated by src family tyrosine kinases" Biochem Biophys Res Commun 371, (2008) 339-344.

Johnston, J.B., et al., "A poxvirus-encoded pyrhi domain protein interacts with ASC-I to inhibit host inflammatory and apoptotic responses to infection" Immunity 23, (2005) 587-598.

Kawana, K., et al., "CD1d degradation in *Chlamydia trachomatis*-infected epithelial cells is the result of both cellular and chlamydial proteasomal activity" J Bioi Chem 282, (2007) 7368-7375.

Knodler, L.A., et al., "Dissemination of invasive *Salmonella* via bacterial-induced extrusion of mucosal epithelia" Proc Natl Acad Sci USA 107, (2010) 17733-17738.

Kubori, T., et al., "Legionella Metaeffector Exploits Host Proteasome to Temporally Regulate Cognate Effector" PLoS Pathog 6 (2010).

Kumar, Y., et al., "Actin and intermediate filaments stabilize the *Chlamydia trachomatis* vacuole by forming dynamic structural Scaffolds" Cell Host Microbe 4, (2008) 159-169.

Li, Z., et al., "Characterization of fifty putative inclusion membrane proteins encoded in the *Chlamydia trachomatis* genome" Infect Immun 76, (2008) 2746-2757.

Lu, H., et al., "*Chlamydia trachomatis* infection of epithelial cells induces the activation of caspase-1 and release of mature IL-18" J Immunol 165, (2000) 1463-1469.

Martinon, F., et al., "The inflammasome: a molecular platform triggering activation of inflammatory caspases and processing of proIL-beta" Mol Cell 10, (2002) 417-426.

McOmie, "Protective Groups in Organic Chemistry" (1973) Plenum Press, New York.

Mehlitz, A., et al., "Complex kinase requirements for *Chlamydia trachomatis* Tarp phosphorylation" FEMS Microbiol Lett 289, (2008) 233-240.

Mital, J., et al., "Specific chlamydial inclusion membrane proteins associate with active Src family kinases in microdomains that interact with the host microtubule network" Cell Microbiol 12, (2010) 1235-1249.

O'Hayer, K.M., et al., "A genetically defined normal human somatic cell system to study ras oncogenesis in vivo and in vitro" Methods Enzymol 407, (2006) 637-647.

Paschen, S.A., et al., "Cytopathicity of *Chlamydia* is largely reproduced by expression of a single chlamydial protease" J Cell Biol 182, (2008) 117-127.

Pirbhai, M., et al., "The secreted protease factor CPAF is responsible for degrading pro-apoptotic BH3-only proteins in *Chlamydia trachomatis*-infected cells" J Biol Chem 281, (2006) 31495-31501.

Remington: the Science and Practice of Pharmacy, 21st ed., Lippincott Williams & Wilkins, A Wolters Kluwer Company, Philadelphia, Pa (2005).

Roan, N. R., et al. "Immune-mediated control of *Chlamydia* infection" Cell Microbiol 10, (2008) 9-19.

Rzomp, K.A., et al., "The GTPase Rab4 interacts with *Chlamydia trachomatis* inclusion membrane protein CT229" Infect Immun 74, (2006) 5362-5373.

Sambrook et al., Molecular Cloning: A Laboratory Manual, (2001) Cold Spring Harbor Laboratory Press, Cold Spring Harbor, NY.

Sansonetti, P.J., et al., "Caspase-1 activation of IL- lbeta and IL-18 are essential for Shigella flexneriinduced inflammation" Immunity 12, (2000) 581-590.

Schotte, P., et al., "Targeting Racl by the Yersinia effector protein YopE inhibits caspase- 1 -mediated maturation and release of interleukin-1 beta" J Bioi Chem 279, (2004) 25134-25142.

Scidmpre-Carlson, M.A., et al., "Identification and characterization of a *Chlamydia trachomatis* early operon encoding four novel inclusion membrane proteins" Mol Microbiol 33, (1999) 753-765.

Shaw, A. C., et al., "Characterization of a secreted *Chlamydia* protease." Cell Microbiol 4, (2002) 411-424.

Sisko, J.L., et al., "Multifunctional analysis of Chlamydiaspecific genes in a yeast expression system" Mol Miorobiol 60, (2006) 51-66.

Stewart and Young, Solid Phase Peptide Synthesis, 2nd ed., (1984) Pierce Chem. Co., Rockford Ill.

Stewart, K.M., et al., "Cell-penetrating peptides as delivery vehicles for biology and medicine" Org Biomol Chem 6, (2008) 2242-2255.

Sun, J., et al., "The host adherens junction molecule nectin-1 is downregulated in *Chlamydia trachomatis*-infected genital epithelial cells" Microbiology 154, (2008) 1290-1299.

The Peptides: Analysis, Synthesis, Biology, Gross and Meienhofer, Eds., vols. 1-2 (1980) Academic Press, New York.

Valdivia, R.H., et al., "*Chlamydia* effector proteins and new insights into chlamydial cellular microbiology" Curr Opin Microbiol 11, (2008) 53-59.

van Deventer, H.W., et al., "C—C chemokine receptor 5 on pulmonary fibrocytes facilitates migration and promotes metastasis via matrix metalloproteinase 9" Am J Pathol 173, (2008) 253-264.

Verbeke, P., et al., "Recruitment of BAD by the *Chlamydia trachomatis* vacuole correlates with host-cell survival" PLoS Pathog 2, (2006) e45.

Vermes, I., et al., "A novel assay for apoptosis. Flow cytometric detection of phosphatidylserine expression on early apoptotic cells using fluorescein labelled Annexin V" Jimmunol Methods 184, (1995) 39-51.

Yu, H., et al., "Role of high-mobility group box 1 protein and poly(ADP-ribose) polymerase 1 degradation in *Chlamydia trachomatis*-induced cytopathicity" Infect Immun 78, (2010) 3288-3297.

Zhong, G. "Killing me softly: chlamydial use of proteolysis for evading host defenses" Trends Microbiol 17, (2009) 467-474.

Zhong, G., et al., "Degradation of transcription factor RFX5 during the inhibition of both constitutive and interferon gamma-inducible major histocompatibility complex class I expression in *Chlamydia*-infected cells" J Exp Med 191, (2000) 1525-1534.

Zhong, G., et al., "Identification of a chlamydial protease-like activity factor responsible for the degradation of host transcription factors" J Exp Med 193, (2001) 935-942.

* cited by examiner

SEQUENCE LISTING

<160> NUMBER OF SEQ ID NOS: 153

<210> SEQ ID NO 1
<211> LENGTH: 609
<212> TYPE: PRT
<213> ORGANISM: Chlamydia trachomatis

<400> SEQUENCE: 1

```
Met Gly Phe Trp Arg Thr Ser Ile Met Lys Met Asn Arg Ile Trp Leu
1               5                   10                  15

Leu Leu Leu Thr Phe Ser Ser Ala Ile His Ser Pro Val Gln Gly Glu
            20                  25                  30

Ser Leu Val Cys Lys Asn Ala Leu Gln Asp Leu Ser Phe Leu Glu His
        35                  40                  45

Leu Leu Gln Val Lys Tyr Ala Pro Lys Thr Trp Lys Glu Gln Tyr Leu
    50                  55                  60

Gly Trp Asp Leu Val Gln Ser Ser Val Ser Ala Gln Gln Lys Leu Arg
65                  70                  75                  80

Thr Gln Glu Asn Pro Ser Thr Ser Phe Cys Gln Gln Val Leu Ala Asp
                85                  90                  95

Phe Ile Gly Gly Leu Asn Asp Phe His Ala Gly Val Thr Phe Phe Ala
            100                 105                 110

Ile Glu Ser Ala Tyr Leu Pro Tyr Thr Val Gln Lys Ser Ser Asp Gly
        115                 120                 125

Arg Phe Tyr Phe Val Asp Ile Met Thr Phe Ser Ser Glu Ile Arg Val
    130                 135                 140

Gly Asp Glu Leu Leu Glu Val Asp Gly Ala Pro Val Gln Asp Val Leu
145                 150                 155                 160

Ala Thr Leu Tyr Gly Ser Asn His Lys Gly Thr Ala Ala Glu Glu Ser
                165                 170                 175

Ala Ala Leu Arg Thr Leu Phe Ser Arg Met Ala Ser Leu Gly His Lys
            180                 185                 190

Val Pro Ser Gly Arg Thr Thr Leu Lys Ile Arg Arg Pro Phe Gly Thr
        195                 200                 205

Thr Arg Glu Val Arg Val Lys Trp Arg Tyr Val Pro Glu Gly Val Gly
    210                 215                 220

Asp Leu Ala Thr Ile Ala Pro Ser Ile Arg Ala Pro Gln Leu Gln Lys
225                 230                 235                 240

Ser Met Arg Ser Phe Phe Pro Lys Lys Asp Asp Ala Phe His Arg Ser
                245                 250                 255

Ser Ser Leu Phe Tyr Ser Pro Met Val Pro His Phe Trp Ala Glu Leu
            260                 265                 270
```

```
Arg Asn His Tyr Ala Thr Ser Gly Leu Lys Ser Gly Tyr Asn Ile Gly
            275                 280                 285

Ser Thr Asp Gly Phe Leu Pro Val Ile Gly Pro Val Ile Trp Glu Ser
        290                 295                 300

Glu Gly Leu Phe Arg Ala Tyr Ile Ser Ser Val Thr Asp Gly Asp Gly
305                 310                 315                 320

Lys Ser His Lys Val Gly Phe Leu Arg Ile Pro Thr Tyr Ser Trp Gln
                325                 330                 335

Asp Met Glu Asp Phe Asp Pro Ser Gly Pro Pro Trp Glu Glu Phe
            340                 345                 350

Ala Lys Ile Ile Gln Val Phe Ser Ser Asn Thr Glu Ala Leu Ile Ile
                355                 360                 365

Asp Gln Thr Asn Asn Pro Gly Gly Ser Val Leu Tyr Leu Tyr Ala Leu
        370                 375                 380

Leu Ser Met Leu Thr Asp Arg Pro Leu Glu Leu Pro Lys His Arg Met
385                 390                 395                 400

Ile Leu Thr Gln Asp Glu Val Val Asp Ala Leu Asp Trp Leu Thr Leu
                405                 410                 415

Leu Glu Asn Val Asp Thr Asn Val Glu Ser Arg Leu Ala Leu Gly Asp
            420                 425                 430

Asn Met Glu Gly Tyr Thr Val Asp Leu Gln Val Ala Gly Tyr Leu Lys
            435                 440                 445

Ser Phe Gly Arg Gln Val Leu Asn Cys Trp Ser Lys Gly Asp Ile Glu
        450                 455                 460

Leu Ser Thr Pro Ile Pro Leu Phe Gly Phe Glu Lys Ile His Pro His
465                 470                 475                 480

Pro Arg Val Gln Tyr Ser Lys Pro Ile Cys Val Leu Ile Asn Glu Gln
                485                 490                 495

Asp Phe Ser Cys Ala Asp Phe Phe Pro Val Val Leu Lys Asp Asn Asp
            500                 505                 510

Arg Ala Leu Ile Val Gly Thr Arg Thr Ala Gly Ala Gly Gly Phe Val
        515                 520                 525

Phe Asn Val Gln Phe Pro Asn Arg Thr Gly Ile Lys Thr Cys Ser Leu
        530                 535                 540

Thr Gly Ser Leu Ala Val Arg Glu His Gly Ala Phe Ile Glu Asn Ile
545                 550                 555                 560

Gly Val Glu Pro His Ile Asp Leu Pro Phe Thr Ala Asn Asp Ile Arg
                565                 570                 575

Tyr Lys Gly Tyr Ser Glu Tyr Leu Asp Lys Val Lys Lys Leu Val Cys
            580                 585                 590

Gln Leu Ile Asn Asn Asp Gly Thr Ile Ile Leu Ala Glu Asp Gly Ser
            595                 600                 605

Phe

<210> SEQ ID NO 2
<211> LENGTH: 25
<212> TYPE: PRT
<213> ORGANISM: Chlamydia trachomatis

<400> SEQUENCE: 2

Ser Leu Phe Tyr Ser Pro Met Val Pro His Phe Trp Ala Glu Leu Arg
1               5                   10                  15

Asn His Tyr Ala Thr Ser Gly Leu Lys
            20                  25
```

```
<210> SEQ ID NO 3
<211> LENGTH: 242
<212> TYPE: PRT
<213> ORGANISM: Chlamydia trachomatis

<400> SEQUENCE: 3

Met Gly Phe Trp Arg Thr Ser Ile Met Lys Met Asn Arg Ile Trp Leu
1               5                   10                  15

Leu Leu Leu Thr Phe Ser Ser Ala Ile His Ser Pro Val Gln Gly Glu
            20                  25                  30

Ser Leu Val Cys Lys Asn Ala Leu Gln Asp Leu Ser Phe Leu Glu His
        35                  40                  45

Leu Leu Gln Val Lys Tyr Ala Pro Lys Thr Trp Lys Glu Gln Tyr Leu
    50                  55                  60

Gly Trp Asp Leu Val Gln Ser Val Ser Ala Gln Gln Lys Leu Arg
65                  70                  75                  80

Thr Gln Glu Asn Pro Ser Thr Ser Phe Cys Gln Gln Val Leu Ala Asp
                85                  90                  95

Phe Ile Gly Gly Leu Asn Asp Phe His Ala Gly Val Thr Phe Phe Ala
            100                 105                 110

Ile Glu Ser Ala Tyr Leu Pro Tyr Thr Val Gln Lys Ser Ser Asp Gly
        115                 120                 125

Arg Phe Tyr Phe Val Asp Ile Met Thr Phe Ser Glu Ile Arg Val
    130                 135                 140

Gly Asp Glu Leu Leu Glu Val Asp Gly Ala Pro Val Gln Asp Val Leu
145                 150                 155                 160

Ala Thr Leu Tyr Gly Ser Asn His Lys Gly Thr Ala Ala Glu Glu Ser
                165                 170                 175

Ala Ala Leu Arg Thr Leu Phe Ser Arg Met Ala Ser Leu Gly His Lys
            180                 185                 190

Val Pro Ser Gly Arg Thr Thr Leu Lys Ile Arg Arg Pro Phe Gly Thr
        195                 200                 205

Thr Arg Glu Val Arg Val Lys Trp Arg Tyr Val Pro Glu Gly Val Gly
    210                 215                 220

Asp Leu Ala Thr Ile Ala Pro Ser Ile Arg Ala Pro Gln Leu Gln Lys
225                 230                 235                 240

Ser Met

<210> SEQ ID NO 4
<211> LENGTH: 326
<212> TYPE: PRT
<213> ORGANISM: Chlamydia trachomatis

<400> SEQUENCE: 4

Gly Tyr Asn Ile Gly Ser Thr Asp Gly Phe Leu Pro Val Ile Gly Pro
1               5                   10                  15

Val Ile Trp Glu Ser Glu Gly Leu Phe Arg Ala Tyr Ile Ser Ser Val
            20                  25                  30

Thr Asp Gly Asp Gly Lys Ser His Lys Val Gly Phe Leu Arg Ile Pro
        35                  40                  45

Thr Tyr Ser Trp Gln Asp Met Glu Asp Phe Asp Pro Ser Gly Pro Pro
    50                  55                  60

Pro Trp Glu Glu Phe Ala Lys Ile Ile Gln Val Phe Ser Ser Asn Thr
65                  70                  75                  80

Glu Ala Leu Ile Ile Asp Gln Thr Asn Asn Pro Gly Gly Ser Val Leu
                85                  90                  95
```

-continued

```
Tyr Leu Tyr Ala Leu Leu Ser Met Leu Thr Asp Arg Pro Leu Glu Leu
            100                 105                 110

Pro Lys His Arg Met Ile Leu Thr Gln Asp Glu Val Val Asp Ala Leu
            115                 120                 125

Asp Trp Leu Thr Leu Leu Glu Asn Val Asp Thr Asn Val Glu Ser Arg
130                 135                 140

Leu Ala Leu Gly Asp Asn Met Glu Gly Tyr Thr Val Asp Leu Gln Val
145                 150                 155                 160

Ala Glu Tyr Leu Lys Ser Phe Gly Arg Gln Val Leu Asn Cys Trp Ser
                165                 170                 175

Lys Gly Asp Ile Glu Leu Ser Thr Pro Ile Pro Leu Phe Gly Phe Glu
            180                 185                 190

Lys Ile His Pro His Pro Arg Val Gln Tyr Ser Lys Pro Ile Cys Val
            195                 200                 205

Leu Ile Asn Glu Gln Asp Phe Ser Cys Ala Asp Phe Phe Pro Val Val
            210                 215                 220

Leu Lys Asp Asn Asp Arg Ala Leu Ile Val Gly Thr Arg Thr Ala Gly
225                 230                 235                 240

Ala Gly Gly Phe Val Phe Asn Val Gln Phe Pro Asn Arg Thr Gly Ile
                245                 250                 255

Lys Thr Cys Ser Leu Thr Gly Ser Leu Ala Val Arg Glu His Gly Ala
            260                 265                 270

Phe Ile Glu Asn Ile Gly Val Glu Pro His Ile Asp Leu Pro Phe Thr
            275                 280                 285

Ala Asn Asp Ile Arg Tyr Lys Gly Tyr Ser Glu Tyr Leu Asp Lys Val
290                 295                 300

Lys Lys Leu Val Cys Gln Leu Ile Asn Asn Asp Gly Thr Ile Ile Leu
305                 310                 315                 320

Ala Glu Asp Gly Ser Phe
                325

<210> SEQ ID NO 5
<211> LENGTH: 41
<212> TYPE: PRT
<213> ORGANISM: Chlamydia trachomatis

<400> SEQUENCE: 5

Arg Ser Phe Phe Pro Lys Lys Asp Asp Ala Phe His Arg Ser Ser
1               5                   10                  15

Leu Phe Tyr Ser Pro Met Val Pro His Phe Trp Ala Glu Leu Arg Asn
                20                  25                  30

His Tyr Ala Thr Ser Gly Leu Lys Ser
            35                  40

<210> SEQ ID NO 6
<211> LENGTH: 35
<212> TYPE: PRT
<213> ORGANISM: Artificial Sequence
<220> FEATURE:
<223> OTHER INFORMATION: Inhibitor of CPAF comprising SEQ ID NO:2.
<220> FEATURE:
<221> NAME/KEY: MISC_FEATURE
<222> LOCATION: (26)..(35)
<223> OTHER INFORMATION: Each Xaa is optional and can be any amino acid
      or amino acid mimetic.

<400> SEQUENCE: 6

Ser Leu Phe Tyr Ser Pro Met Val Pro His Phe Trp Ala Glu Leu Arg
1               5                   10                  15
```

-continued

Asn His Tyr Ala Thr Ser Gly Leu Lys Xaa Xaa Xaa Xaa Xaa Xaa
                20                  25                  30

Xaa Xaa Xaa
        35

<210> SEQ ID NO 7
<211> LENGTH: 34
<212> TYPE: PRT
<213> ORGANISM: Artificial Sequence
<220> FEATURE:
<223> OTHER INFORMATION: Inhibitor of CPAF comprising SEQ ID NO:2.

<400> SEQUENCE: 7

Ser Leu Phe Tyr Ser Pro Met Val Pro His Phe Trp Ala Glu Leu Arg
1               5                   10                  15

Asn His Tyr Ala Thr Ser Gly Leu Lys Arg Arg Arg Arg Arg Arg
                20                  25                  30

Arg Arg

<210> SEQ ID NO 8
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 8

Val Arg Leu Arg Ser Ser Val Pro Gly Val
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Fluorphore-tagged artificial sequence.
<220> FEATURE:
<221> NAME/KEY: MISC_FEATURE
<222> LOCATION: (1)..(1)
<223> OTHER INFORMATION: Val is modified with Abz.

<400> SEQUENCE: 9

Val Arg Leu Arg Ser Ser Val Pro Gly Val
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Fluorophore-tagged artificial sequence.
<220> FEATURE:
<221> NAME/KEY: MISC_FEATURE
<222> LOCATION: (1)..(1)
<223> OTHER INFORMATION: Val is modified with Abz.
<220> FEATURE:
<221> NAME/KEY: MISC_FEATURE
<222> LOCATION: (10)..(10)
<223> OTHER INFORMATION: Val is modified with 3-nitrotyrosine.

<400> SEQUENCE: 10

Val Arg Leu Arg Ser Ser Val Pro Gly Val
1               5                   10

<210> SEQ ID NO 11
<211> LENGTH: 34
<212> TYPE: PRT

-continued

<213> ORGANISM: Artificial Sequence
<220> FEATURE:
<223> OTHER INFORMATION: Synthetic Peptide

<400> SEQUENCE: 11

Asn Phe Ala Leu Ser His Phe Arg Leu Pro Leu Ser Thr Tyr Lys Glu
1               5                   10                  15

Met Pro Tyr Val Ser His Trp Ala Gly Arg Arg Arg Arg Arg Arg Arg
            20                  25                  30

Arg Arg

<210> SEQ ID NO 12
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 12
cgtcaaggag aaaaaacccc ggattctaga actagtatgg aaacagcca gaat         54

<210> SEQ ID NO 13
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 13
tccagtgaaa agttcttctc ctttactcat aagcttaagt cgtgaaacta gcat         54

<210> SEQ ID NO 14
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 14
cgtcaaggag aaaaaacccc ggattctaga actagtatga ctcaaaccgc ggaa         54

<210> SEQ ID NO 15
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 15
tccagtgaaa agttcttctc ctttactcat aagcttagaa acaccttcta tagc         54

<210> SEQ ID NO 16
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 16
cgtcaaggag aaaaaacccc ggattctaga actagtatgt ctatcaaaca tcgc         54

<210> SEQ ID NO 17
<211> LENGTH: 51
<212> TYPE: DNA
<213> ORGANISM: Artificial Sequence
<220> FEATURE:

<223> OTHER INFORMATION: Synthetic Oligonucleotide

<400> SEQUENCE: 17
tccagtgaaa agttcttctc ctttactcat aagctttcag taataataaa c          51

<210> SEQ ID NO 18
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 18
cgtcaaggag aaaaaacccc ggattctaga actagtatgg taagcttcga ttta       54

<210> SEQ ID NO 19
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 19
tccagtgaaa agttcttctc ctttactcat aagctttacg caactcatca t          51

<210> SEQ ID NO 20
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 20
cgtcaaggag aaaaaacccc ggattctaga actagtatgg tttccggaat ctgc       54

<210> SEQ ID NO 21
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 21
tccagtgaaa agttcttctc ctttactcat aagcttttac tctatacgcg a          51

<210> SEQ ID NO 22
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 22
cccactagta tgcgccctct cttctct                                     27

<210> SEQ ID NO 23
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 23
cccaagcttt taatcgcaag agat                                        24

<210> SEQ ID NO 24

```
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 24
cccactagta acaccgtaac tattg                                         25

<210> SEQ ID NO 25
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 25
cccaagcttt tcttgaggtt ttgttg                                        26

<210> SEQ ID NO 26
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 26
cgtcaaggag aaaaaacccc ggattctaga actagtatgc ttggaatacg caaa         54

<210> SEQ ID NO 27
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 27
tccagtgaaa agttcttctc ctttactcat aagcttgaat actcctccca aggc         54

<210> SEQ ID NO 28
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 28
cccactagta aaagttctt attac                                          25

<210> SEQ ID NO 29
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 29
cccactagtt taattatttt gaaa                                          24

<210> SEQ ID NO 30
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 30
```
cgtcaaggag aaaaaacccc ggattctaga actagtatga gaatgaataa acga            54

<210> SEQ ID NO 31
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 31
tccagtgaaa agttcttctc ctttactcat aagctttctc ttcttattga taat            54

<210> SEQ ID NO 32
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 32
cccactagta tcgctggcgt ttgt                                             24

<210> SEQ ID NO 33
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 33
cccactagtt taactagggt tgtg                                             24

<210> SEQ ID NO 34
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 34
cccactagta tgttacgata cttatat                                          27

<210> SEQ ID NO 35
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 35
cccaagcttt tagatttcga tttg                                             24

<210> SEQ ID NO 36
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 36
cccactagta tgcaacttcc gtctatt                                          27

<210> SEQ ID NO 37
<211> LENGTH: 24
<212> TYPE: DNA
<213> ORGANISM: Artificial Sequence
<220> FEATURE:

<223> OTHER INFORMATION: Synthetic Oligonucleotide

<400> SEQUENCE: 37
cccaagctta gctatattga tgat          24

<210> SEQ ID NO 38
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 38
cccactagta tgccggatat tgaaaaa          27

<210> SEQ ID NO 39
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 39
cccaagcttc taatgagctg cttt          24

<210> SEQ ID NO 40
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 40
cccactagta tgtcctcatc aaccaag          27

<210> SEQ ID NO 41
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 41
cccaagcttt tattgttgtt tctt          24

<210> SEQ ID NO 42
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 42
cgtcaaggag aaaaacccc ggattctaga actagtatgc gtctttgttt tatt          54

<210> SEQ ID NO 43
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 43
tccagtgaaa agttcttctc ctttactcat aagcttctta tctagcctgt gacg          54

<210> SEQ ID NO 44

```
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 44
cgtcaaggag aaaaaacccc ggattctaga actagtatgg tttttgttta gtattg        56

<210> SEQ ID NO 45
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 45
tccagtgaaa agttcttctc ctttactcat aagcttgcca acatagcctc c             51

<210> SEQ ID NO 46
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 46
cgtcaaggag aaaaaacccc ggattctaga actagtatgg ttaattagtg gtac          54

<210> SEQ ID NO 47
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 47
tccagtgaaa agttcttctc ctttactcat aagcttgatc atgcgagcac c             51

<210> SEQ ID NO 48
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 48
cccactagta tggctcttat ctat                                           24

<210> SEQ ID NO 49
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 49
cccaagcttt tattttctct ttgt                                           24

<210> SEQ ID NO 50
<211> LENGTH: 57
<212> TYPE: DNA
<213> ORGANISM: Artificial Sequence
<220> FEATURE:
<223> OTHER INFORMATION: Synthetic Oligonucleotide

<400> SEQUENCE: 50
```

```
tccagtgaaa agttcttctc ctttactcat aagctttgat atagatttta gaaggat         57
```

<210> SEQ ID NO 51
<211> LENGTH: 57
<212> TYPE: DNA
<213> ORGANISM: Artificial Sequence
<220> FEATURE:
<223> OTHER INFORMATION: Synthetic Oligonucleotide

<400> SEQUENCE: 51

```
cgtcaaggag aaaaaacccc ggattctaga actagtatga tgagattcgc tcgcttt         57
```

<210> SEQ ID NO 52
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 52

```
cgtcaaggag aaaaaacccc ggattctaga actagtatga gcactgtacc cgtt            54
```

<210> SEQ ID NO 53
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 53

```
tccagtgaaa agttcttctc ctttactcat aagcttttgg gtctgatcca ccag            54
```

<210> SEQ ID NO 54
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 54

```
cgtcaaggag aaaaaacccc ggattctaga actagtatgc gaataggaga tcct            54
```

<210> SEQ ID NO 55
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 55

```
tccagtgaaa agttcttctc ctttactcat aagcttatag atgtgtgtat tctc            54
```

<210> SEQ ID NO 56
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 56

```
cgtcaaggag aaaaaacccc ggattctaga actagtatga aaaaaactgc ttta            54
```

<210> SEQ ID NO 57
<211> LENGTH: 54
<212> TYPE: DNA
<213> ORGANISM: Artificial Sequence
<220> FEATURE:

<223> OTHER INFORMATION: Synthetic Oligonucleotide

<400> SEQUENCE: 57
tccagtgaaa agttcttctc ctttactcat aagcttttgt ctgcatttgc cgtc        54

<210> SEQ ID NO 58
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 58
cccactagtg ctaatatgcg tcttc        25

<210> SEQ ID NO 59
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 59
cccactagtc tgaataggcg cttc        24

<210> SEQ ID NO 60
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 60
cccactagta tggattttat gtctgtt        27

<210> SEQ ID NO 61
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 61
cccaagcttt tcgtatcgag cgcg        24

<210> SEQ ID NO 62
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 62
cccactagta tggtacagca ggaaacg        27

<210> SEQ ID NO 63
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 63
cccaagcttc tacggggtag tagc        24

<210> SEQ ID NO 64

<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 64
cgtcaaggag aaaaaacccc ggattctaga actagtatgt ttcgttatac tctt      54

<210> SEQ ID NO 65
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 65
tccagtgaaa agttcttctc ctttactcat aagcttagcg tcctcgttat tctc      54

<210> SEQ ID NO 66
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 66
cgtcaaggag aaaaaacccc ggattctaga actagtatga gaaagactat tttt      54

<210> SEQ ID NO 67
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 67
tccagtgaaa agttcttctc ctttactcat aagcttgcga gcatggatct taaa      54

<210> SEQ ID NO 68
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 68
cgtcaaggag aaaaaacccc ggattctaga actagtatga aaatagttgt ttct      54

<210> SEQ ID NO 69
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 69
tccagtgaaa agttcttctc ctttactcat aagcttcgag gaggttacca catt      54

<210> SEQ ID NO 70
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 70

-continued

```
cgtcaaggag aaaaaacccc ggattctaga actagtatga aaaaactctt gaaa            54

<210> SEQ ID NO 71
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 71
tccagtgaaa agttcttctc ctttactcat aagcttgaag cggaattgtg catt            54

<210> SEQ ID NO 72
<211> LENGTH: 52
<212> TYPE: DNA
<213> ORGANISM: Artificial Sequence
<220> FEATURE:
<223> OTHER INFORMATION: Synthetic Oligonucleotide

<400> SEQUENCE: 72
cgtcaaggag aaaaaacccc ggattctaga actagtatga caaaaaaaaa tc              52

<210> SEQ ID NO 73
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 73
tccagtgaaa agttcttctc ctttactcat aagcttagca atcgcctctg g               51

<210> SEQ ID NO 74
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 74
cgtcaaggag aaaaaacccc ggattctaga actagtatga gtagcaagct agtg            54

<210> SEQ ID NO 75
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 75
tccagtgaaa agttcttctc ctttactcat aagcttgaat tggaatcctc cgga            54

<210> SEQ ID NO 76
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 76
cccactagta tttcaaatat agaa                                             24

<210> SEQ ID NO 77
<211> LENGTH: 24
<212> TYPE: DNA
<213> ORGANISM: Artificial Sequence
<220> FEATURE:
```

<223> OTHER INFORMATION: Synthetic Oligonucleotide

<400> SEQUENCE: 77
cccactagtc ttttgcttag gatg        24

<210> SEQ ID NO 78
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 78
cgtcaaggag aaaaaacccc ggattctaga actagtatga gagtgagctt acca        54

<210> SEQ ID NO 79
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 79
tccagtgaaa agttcttctc ctttactcat aagctttgac tcgccatccg gcga        54

<210> SEQ ID NO 80
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 80
cgtcaaggag aaaaaacccc ggattctaga actagtatgg attccaacta atgac        55

<210> SEQ ID NO 81
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 81
tccagtgaaa agttcttctc ctttactcat aagcttaaag atcaatcgca atcc        54

<210> SEQ ID NO 82
<211> LENGTH: 52
<212> TYPE: DNA
<213> ORGANISM: Artificial Sequence
<220> FEATURE:
<223> OTHER INFORMATION: Synthetic Oligonucleotide

<400> SEQUENCE: 82
cgtcaaggag aaaaaacccc ggattctaga actagtatga tgaaaagatt at        52

<210> SEQ ID NO 83
<211> LENGTH: 52
<212> TYPE: DNA
<213> ORGANISM: Artificial Sequence
<220> FEATURE:
<223> OTHER INFORMATION: Synthetic Oligonucleotide

<400> SEQUENCE: 83
tccagtgaaa agttcttctc ctttactcat aagcttctcg tctgatttca ag        52

<210> SEQ ID NO 84

```
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 84
cgtcaaggag aaaaaacccc ggattctaga actagtatgg ctaaagataa a            51

<210> SEQ ID NO 85
<211> LENGTH: 52
<212> TYPE: DNA
<213> ORGANISM: Artificial Sequence
<220> FEATURE:
<223> OTHER INFORMATION: Synthetic Oligonucleotide

<400> SEQUENCE: 85
tccagtgaaa agttcttctc ctttactcat aagctttgtg ctagtattaa ac           52

<210> SEQ ID NO 86
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 86
cgtcaaggag aaaaaacccc ggattctaga actagtatgc tacattcact attt         54

<210> SEQ ID NO 87
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 87
tccagtgaaa agttcttctc ctttactcat aagcttaggt gtaacataat accc         54

<210> SEQ ID NO 88
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 88
cgtcaaggag aaaaaacccc ggattctaga actagtatgg actggtcatt tttt         54

<210> SEQ ID NO 89
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 89
tccagtgaaa agttcttctc ctttactcat aagctttagg aaagtttgtt gtag         54

<210> SEQ ID NO 90
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 90
```
cgtcaaggag aaaaaacccc ggattctaga actagtatgg cccggcagga agcc        54

<210> SEQ ID NO 91
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 91
tccagtgaaa agttcttctc ctttactcat aagcttgaat cgcagagcaa tttc        54

<210> SEQ ID NO 92
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 92
cgtcaaggag aaaaaacccc ggattctaga actagtatgg tgtttggtaa tcg         53

<210> SEQ ID NO 93
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 93
tccagtgaaa agttcttctc ctttactcat aagcttaaag accagagctc ctcc        54

<210> SEQ ID NO 94
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 94
cgtcaaggag aaaaaacccc ggattctaga actagtatgg tatttgctgt attag       55

<210> SEQ ID NO 95
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 95
tccagtgaaa agttcttctc ctttactcat aagcttgaac cggactttac ttcc        54

<210> SEQ ID NO 96
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 96
cgtcaaggag aaaaaacccc ggattctaga actagtatgg ccattagtaa aggttc      56

<210> SEQ ID NO 97
<211> LENGTH: 54
<212> TYPE: DNA
<213> ORGANISM: Artificial Sequence
<220> FEATURE:

```
<223> OTHER INFORMATION: Synthetic Oligonucleotide

<400> SEQUENCE: 97
tccagtgaaa agttcttctc ctttactcat aagcttaaag attctattca agcc      54

<210> SEQ ID NO 98
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 98
cgtcaaggag aaaaaacccc ggattctaga actagtatgg atggtcatct aaactg    56

<210> SEQ ID NO 99
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 99
tccagtgaaa agttcttctc ctttactcat aagcttgaac ctgtaagtgg tccc      54

<210> SEQ ID NO 100
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 100
cttactagta tgactccagt aacacca                                    27

<210> SEQ ID NO 101
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 101
cttaagcttt ttacgagagg gtttctt                                    27

<210> SEQ ID NO 102
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 102
cttactagta tggaatccca gaaaagt                                    27

<210> SEQ ID NO 103
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 103
cttaagcttt ttacgagagg gtttctt                                    27

<210> SEQ ID NO 104
```

```
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 104
cttactagta tgtacaccta ttccgtt                                          27

<210> SEQ ID NO 105
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 105
cttaagcttt ttacgagagg gtttctt                                          27

<210> SEQ ID NO 106
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 106
cttactagta tggaatcctc ctcttct                                          27

<210> SEQ ID NO 107
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 107
cttaagcttt ttacgagagg gtttctt                                          27

<210> SEQ ID NO 108
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 108
cttactagta tgactgcatc aggaggagc                                        29

<210> SEQ ID NO 109
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 109
cttactagtt tagggtgatg gagg                                             24

<210> SEQ ID NO 110
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 110
```

```
cttactagta tgtctatcaa acatcgc                                        27
```

<210> SEQ ID NO 111
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 111

```
cttaagcttt cagtaataat aaac                                           24
```

<210> SEQ ID NO 112
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 112

```
cccactagta tgtctccgaa aacgaca                                        27
```

<210> SEQ ID NO 113
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 113

```
cttaagcttt ttacgagagg gtttctt                                        27
```

<210> SEQ ID NO 114
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 114

```
ccccatatga tgactaaggt ttatgcga                                       28
```

<210> SEQ ID NO 115
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 115

```
cttaagctta actgccacca atctttt                                        27
```

<210> SEQ ID NO 116
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 116

```
ccccatatga cagaagctgt gact                                           24
```

<210> SEQ ID NO 117
<211> LENGTH: 27
<212> TYPE: DNA
<213> ORGANISM: Artificial Sequence
<220> FEATURE:

```
<223> OTHER INFORMATION: Synthetic Oligonucleotide

<400> SEQUENCE: 117
cttaagcttc tcaccgagtt tacgagt                                              27

<210> SEQ ID NO 118
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 118
cttactagta tggtttccgg aatctgc                                              27

<210> SEQ ID NO 119
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 119
cttaagcttt tactcttata cgcgc                                                25

<210> SEQ ID NO 120
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 120
ccactagttt cttgagtagt ggtc                                                 24

<210> SEQ ID NO 121
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 121
cccactagta ccaaataatg caggtag                                              27

<210> SEQ ID NO 122
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 122
cccactagta tcgctggcgt ttgt                                                 24

<210> SEQ ID NO 123
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 123
cccactagtt taactagggt tgtg                                                 24

<210> SEQ ID NO 124
```

<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 124
cttactagta tgttacgata cttatat                                27

<210> SEQ ID NO 125
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 125
cttactagta tgttagattt cgatttg                                27

<210> SEQ ID NO 126
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 126
cttactagta tgcaacttcc gtctattatt                             30

<210> SEQ ID NO 127
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 127
cttaagcttc taatgagctg cttt                                   24

<210> SEQ ID NO 128
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 128
cttactagta tgtcctcatc aaccaag                                27

<210> SEQ ID NO 129
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 129
cttaagcttt tattgttgtt tctt                                   24

<210> SEQ ID NO 130
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 130

```
cttactagta tgaaagttgt tgtgaat                                          27

<210> SEQ ID NO 131
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 131
cttaagcttt tattttctt ttgt                                              24

<210> SEQ ID NO 132
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 132
cttactagta tggattttat gtctgtt                                          27

<210> SEQ ID NO 133
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 133
cttaagcttt tcgtatcgag cgcg                                             24

<210> SEQ ID NO 134
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 134
cttactagta tggtacagca ggaaacg                                          27

<210> SEQ ID NO 135
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 135
cttaagcttc tacggggtag tagc                                             24

<210> SEQ ID NO 136
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 136
gtcggatcca ttatggcagc aacg                                             24

<210> SEQ ID NO 137
<211> LENGTH: 30
<212> TYPE: DNA
<213> ORGANISM: Artificial Sequence
<220> FEATURE:
```

<223> OTHER INFORMATION: Synthetic Oligonucleotide

<400> SEQUENCE: 137
gagtgcggcc gcaccggtta gtaattgtac          30

<210> SEQ ID NO 138
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 138
cccactagta tgagaaacca tccgattcca g          31

<210> SEQ ID NO 139
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 139
cccaagcttg ctagaagcca atgttc          26

<210> SEQ ID NO 140
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 140
cccactagta gtagcataag ccctatag          28

<210> SEQ ID NO 141
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 141
cccactagtg atattcccaa ccgaagaag          29

<210> SEQ ID NO 142
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 142
cccactagta tggacaacca ccctcctg          28

<210> SEQ ID NO 143
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 143
cccaagctta gaactcggta gggtagc          27

<210> SEQ ID NO 144

```
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 144
cccactagta tgtgggagaa tgcagatg                                    28

<210> SEQ ID NO 145
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 145
cccaagctta gtcgataata aattg                                       25

<210> SEQ ID NO 146
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 146
cccactagta tgttgttatc ttgg                                        24

<210> SEQ ID NO 147
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 147
cccaagcttt ttttcctgag acgag                                       25

<210> SEQ ID NO 148
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 148
cttactagta tgatgaaaaa atttctctttt c                               31

<210> SEQ ID NO 149
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 149
cttaagcttt taaggtgtaa cata                                        24

<210> SEQ ID NO 150
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 150
```

```
cttactagta tgtctttgca aacacca                                              27

<210> SEQ ID NO 151
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 151
cttaagcttt tataggaaag tttg                                                 24

<210> SEQ ID NO 152
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 152

Thr Leu Phe Tyr Ser Pro Met Val Pro His Phe Trp Ser Glu Phe Arg
1               5                   10                  15

Asn His Tyr Ala Thr Ser Gly Leu Lys
            20                  25

<210> SEQ ID NO 153
<211> LENGTH: 80
<212> TYPE: PRT
<213> ORGANISM: Artificial Sequence
<220> FEATURE:
<223> OTHER INFORMATION: Synthetic Peptide

<400> SEQUENCE: 153

Ser Ala Ser Glu Asn Cys Leu Phe Thr Asn Glu Met Val Pro Tyr Phe
1               5                   10                  15

Trp Lys Glu Leu Arg Gln Gln Tyr Lys Arg Gly Leu Ser Ser Asp Tyr
            20                  25                  30

Asn Ile Gly Ser Lys Arg Gly Phe Leu Pro Asp Phe Gly His Val Thr
            35                  40                  45

Trp Lys Ala Lys Ser Gly Pro Tyr His Ala Tyr Val Phe Thr Cys Thr
        50                  55                  60

Asp Asn His Gly Gln Ser His Ser Ile Gly Phe Leu Arg Ile Ser Thr
65                  70                  75                  80
```

ANTICHLAMYDIAL AGENTS

CROSS REFERENCE TO RELATED APPLICATIONS

This application claims priority to U.S. Provisional Patent Application Ser. No. 61/474,301, filed Apr. 12, 2011, and which is incorporated by reference herein in its entirety.

STATEMENT REGARDING FEDERAL FUNDING

This disclosure was produced in part using NIH/NIAID funds under grant 5R01-AI081694-02, entitled "*Chlamydia* Effector Proteins," and grant AI46611. Accordingly, the Federal Government has certain rights in this disclosure.

SEQUENCE LISTING

The sequence listing is provided with the filing of the application and is incorporated herein by reference. The sequence listing file ASFILED_SequenceListing_ST25.txt was generated on Jan. 30, 2012 and is 42,598 bytes in size.

BACKGROUND

The bacterial phylum Chlamydiae describes Gram-negative, obligate intracellular pathogens that infect a wide range of animal hosts. One species that affects humans is *Chlamydia trachomatis*, a globally prevalent, sexually transmitted pathogen that infects the urogenital tract and ocular epithelia and can cause infertility, pelvic inflammatory diseases, and blindness. Another species, *C. pneumoniae*, targets the upper respiratory tract and can cause both pneumonia and cardiovascular disease. *Chlamydia* infection begins with an elementary body (EB), the invasive form of the bacteria, binding to and entering an epithelial cell. Immediately after entry, an EB transitions into a replicative reticulate body (RB) and establishes a membrane-bound parasitophorous inclusion that avoids fusion with host lysosomal compartments. At mid-to-late stages of infection, RBs revert to EB form and emerge to infect neighboring cells.

As obligate intracellular pathogens, the Chlamydiae have necessarily developed diverse strategies for evading and suppressing host defenses. For example, invading *Chlamydia* cells infiltrate the host cytoplasm with effector proteins targeting a range of host processes to facilitate persistent infection and bacterial propagation. One such effector protein is Chlamydial Protease-like Activity Factor (CPAF), a multimeric serine protease that is produced in the inclusion lumen and transported to the host cytoplasm.

SUMMARY

In an aspect, the disclosure provides an inhibitor of Chlamydial Protease-like Activity Factor (CPAF) comprising SEQ ID NO:2 (SLFYSPMVPHFWAELRNHYATSGLK). In another aspect, the disclosure provides a polypeptide comprising SEQ ID NO:2 (SLFYSPMVPHFWAELRN HYATSGLK), wherein the polypeptide inhibits CPAF activity. Another aspect of the disclosure provides an inhibitor of CPAF comprising SEQ ID NO:6 (SLFYSPMVPHFWAELRNHYATSGLK $X_1X_2X_3X_4X_5X_6X_7X_8X_9X_{10}$), wherein X1-X10 are each independently optionally present and are selected from any amino acid. In certain embodiments, the disclosed inhibitors of CPAF can comprise SEQ ID NO:7 (SLFYSPMVPHFWAELRNHYATSGLKRRRRRRRRRR).

In an aspect, the disclosure provides methods of identifying an inhibitor of CPAF comprising contacting a first *Chlamydia*-infected cell with a candidate compound and monitoring the first *Chlamydia*-infected cell for one or more indicators of CPAF inhibition. In embodiments of this aspect, the first *Chlamydia*-infected cell can be a mammalian cell, and the mammalian cell can be, for example, a HeLa cell. In some embodiments, the first *Chlamydia*-infected cell is infected with *C. trachomatis*. Further embodiments provide that the disclosed one or more indicators of CPAF inhibitions can comprise inclusion structure collapse, aggregation of one or more inclusion membrane markers, IL-8 secretion, nuclear condensation, caspase-1 activity, and/or caspase-1 dependent apoptosis. Certain embodiments of this aspect provide for additional steps that can include monitoring a negative control *Chlamydia*-infected cell for the one or more indicators of CPAF inhibition and comparing the indicators of CPAF inhibition observed in the first *Chlamydia*-infected cell with the indicators of CPAF inhibition observed in the negative control *Chlamydia*-infected cell, wherein a greater magnitude of one or more indicators of CPAF inhibition in the first *Chlamydia*-infected cell relative to the negative control *Chlamydia*-infected cell indicates that the candidate compound is an inhibitor of CPAF.

In another aspect, the disclosure provides methods of identifying an inhibitor of CPAF comprising contacting a first sample, comprising CPAF and a candidate compound, with a first CPAF substrate and measuring cleavage of the first CPAF substrate in the first sample. In some embodiments, the disclosure provides CPAF substrates comprising SEQ ID NO:8 (VRLRSSVPGV). In embodiments of the disclosed methods, the measuring step comprising separating the CPAF substrate and a cleavage fragment of the CPAF substrate by high-performance liquid chromatography (HPLC). In other embodiments, the disclosed measuring step can comprise detecting cleavage of the CPAF substrate by fluorescence resonance energy transfer (FRET). Certain embodiments also provide methods further comprising contacting a second sample, comprising CPAF and a CPAF inhibitor, with a second CPAF substrate, measuring cleavage of the second CPAF substrate in the second sample, and comparing cleavage of the first CPAF substrate in the first sample to cleavage of the second CPAF substrate in the second sample. In embodiments, the CPAF inhibitor can comprise lactacystin, SEQ ID NO:2, and/or SEQ ID NO:7.

In a further aspect, the disclosure provides methods of treating a *Chlamydia* infection in a subject in need thereof, comprising administering an effective amount of an inhibitor CPAF to the subject. In some embodiments, the inhibitor of CPAF can comprise a CPAF inhibitory segment, and in certain embodiments, the inhibitor of CPAF can comprise SEQ ID NO:2. In embodiments, the inhibitor of CPAF can comprise a protein-transduction domain. In some embodiments, the inhibitor of CPAF can comprise SEQ ID NO:6, and in certain embodiments, SEQ ID NO:7. In some embodiments, the inhibitor of CPAF comprises a selective inhibitor of CPAF.

Another aspect of the disclosure provides compositions comprising an inhibitor of CPAF and one or more of a carrier, vehicle, diluent, or adjuvant. In another aspect, the disclosure provides methods of treating a *Chlamydia* infection in a subject in need thereof, comprising administering an effective amount of a composition comprising an inhibitor of CPAF to the subject. Another aspect provides methods of eliciting an anti-Chlamydia immune response in a subject comprising administering an effective amount of an inhibitor of CPAF to the subject. In embodiments, the anti-*Chlamydia* immune response comprises a humoral immune response, a cellular immune response, and/or a protective immune response.

Further aspects provide methods of treating or inhibiting a *Chlamydia* infection in a cell comprising contacting the cell with an inhibitor of CPAF, and another aspect provides methods of reducing the virulence of a *Chlamydia* infection, comprising contacting a *Chlamydia*-infected cell with an inhibitor of CPAF.

The disclosure provides for additional aspects and embodiments that will be apparent to one of ordinary skill in the art in light of the drawings and detailed description that follows.

DETAILED DESCRIPTION

Figure 1:
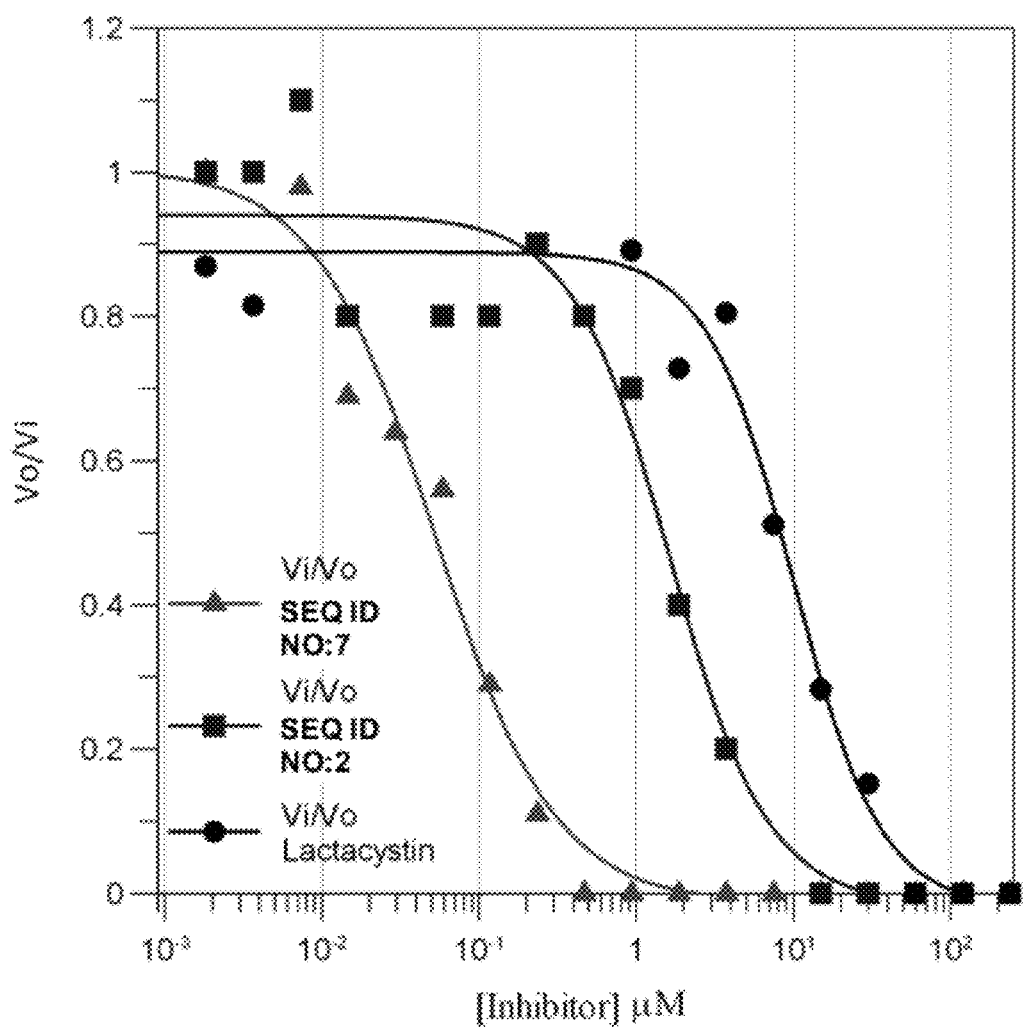
FIG. 1 depicts the results of HPLC-based CPAF inhibition assays using a model CPAF substrate (SEQ ID NO:9) to compare inhibition of CPAF protease activity by SEQ ID NO:7, SEQ ID NO:2, and lactacystin. HPLC-based assays were performed in a final volume of 100 µL containing assay buffer, CPAF (62.5 nM), substrate 1 (0.5 mM), and varying concentrations of inhibitor (0-240 µM).

It will be understood that the various aspects and embodiments described herein are merely intended to provide illustration and do not serve to limit the scope of the claims. Articles "a" and "an" are used herein to refer to one or to more than one (i.e. at least one) of the grammatical object of the article. By way of example, "an element" means at least one element and can include more than one element. Unless otherwise defined, all technical terms used herein have the same meaning as commonly understood by one of ordinary skill in the art to which this disclosure belongs, and all references cited herein are hereby incorporated by reference in their entireties for all purposes.

Further, no admission is made that any reference, including any patent or patent document, cited in this specification constitutes prior art. In particular, it will be understood that, unless otherwise stated, reference to any document herein does not constitute an admission that any of these documents form part of the general knowledge in the prior art in the United States or in any other country. Any discussion of the references states what their authors assert, and the applicant reserves the right to challenge the accuracy and pertinence of any of the documents cited herein.

In a general sense the disclosure relates to active agents and methods effective against *Chlamydia* and/or associated diseases and disorders, as well as methods for screening candidate compounds for anti-chlamydial activity. In embodiments, the disclosure relates to Chlamydial Protease-like Activity Factor (CPAF) and inhibitors thereof, including any small molecules, isolated and/or synthetic proteins or peptides, and/or other compounds that can inhibit an activity of CPAF (also referred to herein as "CPAF inhibitors" or "inhibitors of CPAF"). The disclosed CPAF inhibitors, as well as compositions and methods comprising the same, have broad applications as they can be used to treat a spectrum of diseases, disorders, and clinical indications associated with *Chlamydia* infection and/or to identify or evaluate candidate compounds as inhibitors of CPAF. Inhibitors of CPAF may be selective or non-selective. A selective inhibitor of CPAF selectively inhibits CPAF activity relative to the activity of proteins, enzymes, and proteases from a host organism (i.e., they reduce CPAF activity but do not significantly inhibit or interfere with host cell proteases, such as, for example, the proteasome). In contrast, a non-selective CPAF inhibitor reduces CPAF activity but can also inhibit or interfere with one or more host cell proteases.

*Chlamydia*, Chlamydiae, chlamydial, and the like refer to any infective organism of the phylum Chlamydiae. Non-limiting examples of *Chlamydia* include *Chlamydia trachomatis*, *C. pneumoniae*, *C. muridarum*, and *C. caviae*, including reference strains and clinical isolates thereof. A significant proportion of *Chlamydia* genomes (~10%) encode products known as effector proteins that are delivered to the host cell and can influence processes such as bacterial entry, replicative vacuole formation, modulation of immunity, inhibition of apoptosis, and/or exit from the host cell, and the like. CPAF is one such effector protein—widely conserved among chlamydial species—that is expressed by the invading bacteria and delivered to the host cytoplasm at around 14-16 hours post-infection. Among its activities, CPAF cleaves various host proteins, including but not limited to transcription factors required for major histocompatibility complex expression (RFX5 and USF1) and NFκB signaling (p65/RelA), the pro-apoptotic factors Bim and Puma, pro-apoptotic BH3-only proteins, intermediate filament proteins (including vimentin), cytokeratin 8, the adherence junction protein nectin-1, the lipid presentation protein CD1d, the pro-inflammatory mediator HMGB1, the cell-cycle regulator CyclinB, the DNA-repair factor PARP, and the hypoxia-inducible factor HIF1a. In addition, CPAF cleaves a number of bacterial proteins, such as, for example, Ct005, IncD (Ct115), IncE (Ct116), IncC (Ct233), Ct288, Ct694, Ct695, Ct813, Ct875, and Tarp (Ct456). "CPAF activity," as used herein, includes any biological activity, or combination of biological activities, that is associated with CPAF, whether in vitro or in vivo. CPAF activity can relate to, for example, any one or combination of protease activities (targeting one or more synthetic, bacterial, and/or host proteins or peptides), maintenance of inclusion integrity, immune suppression, remodeling of the host cytoskeleton, suppression of caspase-1 dependent cell death, and the like. Protease activity, proteolytic cleavage, substrate cleavage, and the like can include enzymatic processing of a polypeptide substrate, including exo- and endopeptidase activities, that yields, for example, two or more distinct substrate fragments, partial degradation, or complete degradation of the substrate.

Active CPAF is a heterodimeric serine protease that includes catalytic domains of approximately 29 kDa (CPAFn) and approximately 35 kDa (CPAFc), but CPAF is initially synthesized as a catalytically inactive zymogen of approximately 70 kDa. The CPAF zymogen comprises CPAFn at its N-terminal end, CPAFc at its C-terminal end, and an intervening polypeptide of about 40 amino acids. The intervening polypeptide includes a ~25 amino acid CPAF inhibitory segment that blocks the CPAF active site and substrate-binding pocket within the CPAF zymogen, preventing substrates from reaching the active site and inhibiting proteolytic activity. CPAF zymogen undergoes maturation into its active form via stepwise autocatalytic cleavage events. Huang, et al., *Cell Host & Microbe*, 4:529-542 (2008). Zymogen cleavage during CPAF maturation separates CPAFn and CPAFc from the intervening polypeptide comprising the CPAF inhibitory segment, thus opening the CPAF active site for substrate recognition and proteolytic activity. "Chlamydial Protease-like Activity Factor" or CPAF, as used herein, encompasses any of the various isoforms of CPAF protein expressed by a bacterium of the phylum Chlamydiae. This includes, for example, zymogen, proenzyme, and other precursor forms of CPAF; active forms of CPAF; active fragments, including CPAFn and CPAFc; CPAF intervening polypeptides; CPAF inhibitory segments; and the like, as well as fragments (N-terminal, C-terminal, and/or internal deletions) of any of the preceding and variants having amino acid sequence homology (e.g., at least about 70% sequence identity) to any of the preceding. CPAF thus includes, but is not limited to, the following polypeptide sequences expressed by *C. trachomatis*: a CPAF zymogen (SEQ ID NO:1), a CPAF inhibitory segment (SEQ ID NO:2), a CPAFn catalytic domain (SEQ ID NO:3), a CPAFc catalytic domain (SEQ ID NO:4), and a CPAF intervening polypeptide (SEQ ID NO:5).

In an aspect, the disclosure provides an inhibitor of CPAF comprising SEQ ID NO:2:

(SEQ ID NO: 2)
S-L-F-Y-S-P-M-V-P-H-F-W-A-E-L-R-N-H-Y-A-T-S-G-L-K

In embodiments, the disclosed inhibitors of CPAF can comprise a peptide having at least about 50%, at least about 55%, at least about 60%, at least about 65%, at least about 70%, at least about 75%, at least about 80%, at least about 85%, at least about 90%, at least about 92%, at least about 95%, at least about 96%, or at least about 100% identity with SEQ ID NO:2, provided that the peptide retains the ability to inhibit CPAF activity. In some embodiments, the inhibitors of CPAF can comprise modifications that, for example, add, delete, replace, and/or modify amino acids relative to SEQ ID NO:2, if such modifications result in a peptide that functions as an inhibitor of CPAF. In some embodiments, such modifications can preserve and/or enhance known or predicted interactions between the disclosed peptides and CPAF.

A "peptide" as used herein refers to a compound that comprises at least a single amino acid residue, or derivative thereof, or a compound that comprises at least one amino acid mimetic. Amino acids are well known in the art and include, for example, isoleucine, leucine, alanine, asparagine, glutamine, lysine, aspartic acid, glutamic acid, methionine, cysteine, phenylalanine, threonine, tryptophan, glycine, valine, proline, serine, tyrosine, arginine, histidine, norleucine, ornithine, taurine, selenocysteine, selenomethionine, lanthionine, 2-aminoisobutyric acid, dehydroalanine, hypusine, citrulline, 3-aminopropanoic acid, gamma-aminobutyric acid, and the like. An "amino acid side chain" refers to the various organic substituent groups that differentiate one amino acid from another. An amino acid having a hydrophobic side chain includes the non-limiting examples of alanine (A), isoleucine (I), leucine (L), methionine (M), phenylalanine (F), tryptophan (W), tyrosine (Y), and valine (V). An amino acid having a positively charged side chain, under typical physiological conditions, includes the non-limiting examples of arginine (R), histidine (H), and lysine (K). An amino acid having a negatively charged side chain, under typical physiological conditions, includes the non-limiting examples of aspartic acid (D) and glutamic acid (E). An amino acid having a polar uncharged side chain includes the non-limiting examples of serine (S), threonine (T), asparagine (N), and glutamine (Q). A "derivative" of an amino acid side chain refers to an amino acid side chain that has been modified structurally (e.g., through chemical reaction to form new species, covalent linkage to another molecule, and the like). Some embodiments provide for a peptide comprising modifications including, but not limited to, glycosylation, side chain oxidation, acetylation, amidation, or phosphorylation, as long as the modification does not destroy the biological activity of the peptides as herein described. Typically, a peptide comprises a sequence of at least 3 amino acids (amino acid residues) or amino acid mimetics. The peptides described herein can be provided in a charged form, typically with a net positive charge, and can be generated and used as salts (e.g., alkali metal salts, basic or acidic addition salts). The selection and formation of such salts are within the ability of one skilled in the art. See, e.g., *Remington: The Science and Practice of Pharmacy*, 21$^{st}$ ed., Lippincott Williams & Wilkins, A Wolters Kluwer Company, Philadelphia, Pa. (2005).

An "amino acid mimetic" as used herein is meant to encompass peptidomimetics, peptoids (poly-N-substituted glycines) and β-peptides (i.e., peptides that comprise one or more amino acids residues having the amino group attached at the β-carbon rather than the α-carbon). Suitably, the amino acid mimetic comprises an altered chemical structure that is designed to adjust molecular properties favorably (e.g., stability, activity, reduced immunogenic response, solubility, etc.). Typically, the altered chemical structure is thought to not occur in nature (e.g., incorporating modified backbones, non-natural amino acids, etc.). Thus, non-limiting examples of amino acid mimetic include D-peptides, retro-peptides, retro-inversion peptides, β-peptides, peptoids, and compounds that include one or more D-amino acids, poly-N-substituted glycine, or β-amino acid, or any combination thereof.

The disclosed peptides and polypeptides can be produced using any means for making polypeptides known in the art, including, e.g., synthetic and recombinant methods. For example, in some embodiments the peptides can be synthesized using synthetic chemistry techniques such as solid-phase synthesis, Merrifield-type solid-phase synthesis, t-Boc solid-phase synthesis, Fmoc solid-phase synthesis, BOP solid-phase synthesis, and solution-phase synthesis. See, for example, Stewart and Young, *Solid Phase Peptide Synthesis*, 2$^{nd}$ ed., (1984) Pierce Chem. Co., Rockford Ill.; *The Peptides: Analysis, Synthesis, Biology*, Gross and Meienhofer, Eds., vols. 1-2 (1980) Academic Press, New York; Bodansky, *Principles of Peptide Synthesis*, (1984) Springer-Verlag, Berlin. In other embodiments, the peptides can be produced, for example, by expressing the peptide from a nucleic acid encoding the peptide in a cell or in a cell-free system according to recombinant techniques familiar to those of skill in the art. See, e.g., Sambrook et al., *Molecular Cloning: A Laboratory Manual*, (2001) Cold Spring Harbor Laboratory Press, Cold Spring Harbor, N.Y.; Ausubel et al., *Current Protocols in Molecular Biology*, (2002) John Wiley & Sons, Somerset, N.J.; each of which are hereby incorporated by reference in their entireties. The peptides can incorporate any of the various modifications and protective groups described herein or otherwise known to those of skill in the art, such as, for example, those described in McOmie, *Protective Groups in Organic Chemistry*, (1973) Plenum Press, New York. In some embodiments, the peptides can be isolated and/or purified to a single active species.

In some embodiments, the disclosure provides selective inhibitors of CPAF. A selective inhibitor of CPAF inhibits one or more CPAF activity without significantly interfering with or inhibiting host functions, processes, proteins, and/or biochemical activities, such as, for example, host proteases or protease complexes (e.g., the proteasome). Because a selective inhibitor of CPAF does not significantly interfere with host functions, a normal host cell would exhibit normal or nearly normal function with mild or no side effects in the presence of the selective inhibitor of CPAF. In contrast, lactacystin, a cyclic amide synthesized by *Streptomyces* bacteria, is a non-selective inhibitor of CPAF. While lactacystin inhibits CPAF, it also inhibits the proteasome, a critical mediator of protein degradation in eukaryotic cells. In some embodiments, the disclosed selective CPAF inhibitors can bind CPAF with enhanced affinity relative to host proteins (such as host proteases). For example, the disclosed selective CPAF inhibitors may bind to CPAF with at least about 2-fold, at least about 3-fold, at least about 4-fold, at least about 5-fold, or at least about 10-fold greater affinity than to a host protein.

CPAF recognizes a sequence of SEQ ID NO:2 as a substrate, cleaving at a position corresponding to residues M7 and V8 of SEQ ID NO:2. Huang, et al., *Cell Host & Microbe*, 4:529-542 (2008). Prior studies have only evaluated peptides altered for resistance to cleavage by CPAF, comprising sequence mutations relative to SEQ ID NO:2, for interaction with or inhibition of CPAF. Huang, et al., *Cell Host & Microbe*, 4:529-542 (2008). As disclosed herein and contrary to any prior suggestion, peptides comprising SEQ ID NO:2 function as potent inhibitors of CPAF.

In some embodiments, the disclosure provides inhibitors of CPAF comprising SEQ ID NO:6:

```
                                          (SEQ ID NO: 6)
S-L-F-Y-S-P-M-V-P-H-F-W-A-E-L-R-N-H-Y-A-T-S-G-L-K-

X1-X2-X3-X4-X5-X6-X7-X8-X9-X10
```

Figure 2:
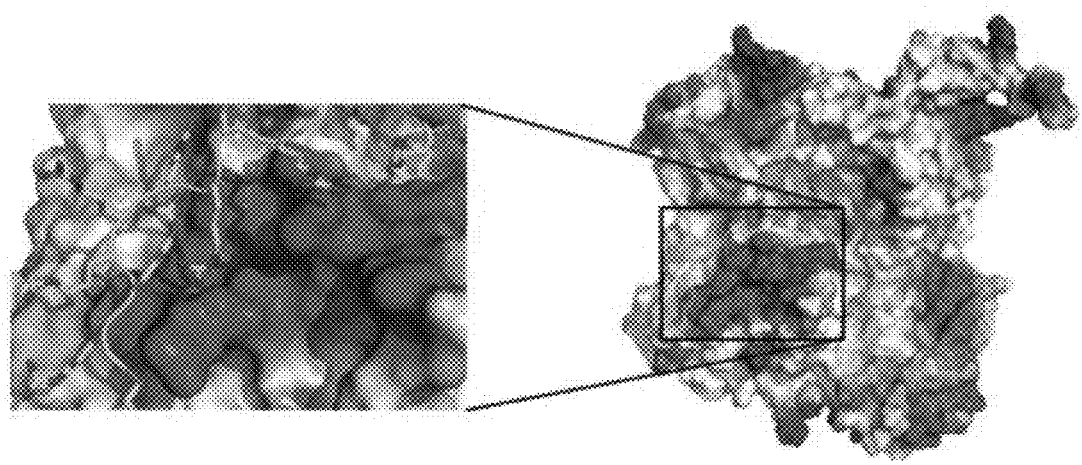
FIG. 2 depicts a molecular model of a peptide of SEQ ID NO:7 modeled into the crystal structure of CPAF. The globular space-filling model represents the three-dimensional structure of CPAF, and the associated ribbon model depicts the predicted position of SEQ ID NO:7 in complex with CPAF. Shading on the CPAF model depicts areas of surface charge on the CPAF protein. The inset focuses on a region of CPAF comprising a dense group of negatively charged residues on the CPAF surface predicted to interact with the polyarginine tail of SEQ ID NO:7 (see detail).

The disclosure thus provides inhibitors of CPAF comprising a CPAF inhibitory segment, such as, but not limited to, SEQ ID NO:2 and comprising one or more additional residues or domains as exemplified by SEQ ID NO:6. Each of additional residues represented by $X_1$-$X_{10}$ in SEQ ID NO:6 is optionally present, and each is independently selected from any amino acid. In some embodiments $X_1$-$X_{10}$ are selected such that the net charge of the $X_1$-$X_{10}$ portion of the sequence has a net consists of, or consists essentially of, SEQ ID NO:7. SEQ ID NO:7 comprises a CPAF inhibitory segment (SEQ ID NO:2) plus an additional C-terminal domain comprising nine arginine residues. SEQ ID NO:7 exhibits enhanced potency as an inhibitor of CPAF relative to a corresponding inhibitor of CPAF (SEQ ID NO:2) lacking the additional poly-arginine domain of SEQ ID NO:7. Accordingly, in some embodiments of the disclosure, a CPAF inhibitor can comprise a CPAF inhibitory segment plus one or more additional residues or domains with one or more properties similar to the poly-arginine domain of SEQ ID NO:7 for example, instead of or in addition to arginine, other polar or positively charged residues such as lysine, histidine, glutamine, ornithine, etc., could be selected to promote interactions between an inhibitor of CPAF and a cluster of negatively charged residues on the surface of CPAF indicated in FIG. 2. The CPAF inhibitors disclosed by SEQ ID NO:6 and SEQ ID NO:7 are merely illustrative, and the disclosure provides for CPAF inhibitors comprising additional residues or domains designed to confer, promote, enhance, mask, or eliminate any property of or intermolecular interaction comprising the disclosed CPAF inhibitors.

In some embodiments, the CPAF inhibitor can include one or more additional residues or domains that confer one or more additional properties or functions. For example, some embodiments provide additional residues or domains that facilitate detection, immunodetection, or purification; exemplary such modifications include HA, GFP, FLAG, GST, His, and the like. In some embodiments, additional residues or domains can extend the half-life of the CPAF inhibitor (such as, for example, human serum albumin, an immunoglobulin Fc domain, polyethylene glycol, etc.) or promote cellular uptake (such as, for example, protein transduction domains (PTDs) derived from *Drosophila*, herpes simplex virus VP22 protein, HIV-1 tat, and the like). For example, SEQ ID NO:7 includes a 25-residue CPAF inhibitory segment derived from *C. trachomatis* (SEQ ID NO:2) plus an additional C-terminal, poly-arginine PTD.

In further aspects, the disclosure provides compositions comprising an inhibitor of CPAF. In some embodiments, the disclosed compositions can comprise an inhibitor of CPAF and one or more of a carrier, vehicle, diluent, or adjuvant. In another aspect, the disclosure provides methods of treating a *Chlamydia* infection in a subject in need thereof. In some embodiments, the disclosed methods can comprise administering an effective amount of an inhibitor of CPAF to the subject. In some embodiments, the disclosed methods can comprise administering a composition or formulation comprising an inhibitor of CPAF to the subject. Embodiments also provide methods of inhibiting a *Chlamydia* infection in a cell comprising contacting the cell with an inhibitor of CPAF and methods of reducing the virulence of a *Chlamydia* infection comprising contacting a *Chlamydia*-infected cell with an inhibitor of CPAF.

In some embodiments, the disclosed inhibitors of CPAF and/or compositions comprising an inhibitor of CPAF can be used to reduce the virulence of a *Chlamydia* infection and/or treat, ameliorate, eliminate, or prevent certain signs, symptoms, and/or deleterious effects of acute and/or chronic *Chlamydia* infection. In some embodiments, the disclosed compositions, methods, and CPAF inhibitors can be used to treat or clear a *Chlamydia* infection. As used herein, *Chlamydia* infection includes but is not limited to urogenital, pulmonary, and/or ocular infections by any member of the Chlamydiae. Non-limiting examples of Chlamydiae include *Chlamydia trachomatis, C. pneumoniae, C. muridarum,* and *C. caviae,* including reference strains and clinical isolates thereof. In this regard, the disclosed inhibitors of CPAF and/or compositions comprising an inhibitor of CPAF can be used alone or in combination with other known anti-Chlamydial drugs or treatments to formulate pharmaceutical compositions for treating a *Chlamydia* infection.

In some embodiments, the disclosed inhibitors of CPAF, compositions, and methods, can act via mechanisms including, but not limited to destabilizing bacterial inclusions, reducing production of progeny bacteria, stunting inclusion growth, and/or promoting cell death in infected cells through mechanisms including caspase-1 mediated cell death.

In some embodiments, the disclosed inhibitors of CPAF, compositions, and methods, can act by facilitating anti-Chlamydia immune responses in the host. In embodiments, the disclosure provides a method of eliciting an anti-Chlamydia immune response in a subject comprising administering an effective amount of an inhibitor of CPAF to the subject. For example, cell death in *Chlamydia*-infected cells (e.g., caspase-1 mediated cell death) due to the disclosed inhibitors of CPAF, compositions, and methods can include cell lysis and consequent exposure of various *Chlamydia*-derived antigens to the host immune system. Access to *Chlamydia*-derived antigens can induce adaptive and/or innate immune responses in the host that aid in clearing an existing *Chlamydia* infection and/or protective immune responses that can prevent or reduce the incidence or severity of subsequent re-infection. In embodiments, anti-Chlamydia immune responses can include, but are not limited to, humoral responses (e.g., immune responses mediated by antigen-specific antibody molecules, including antibodies secreted produced in serum and at mucosal surfaces), cellular responses (e.g., proliferation, recruitment, cytotoxicity, and production of immune signaling and effector molecules by lymphocytes, including, for example, helper and cytotoxic T cells, etc.), innate responses (e.g., cytotoxicity, phagocytosis, and production of immune signaling and effector molecules by cells such as macrophages, NK cells, mast cells, etc.). The induction of host immunity can be assessed by various methods as would be apparent to those in the art; for example, measuring the presence or concentration of systemic or mucosal antibodies specific for a Chlamydial protein.

The terms "inhibiting," "treating," and "treatment," when used with reference to a disease, subject, or a subject in need of treatment include, but are not limited to, halting or slowing of disease progression, remission of disease, prophylaxis or lessening of symptoms and/or clinical indications, reduction in disease and/or symptom severity, or reduction in disease length as compared to an untreated subject, and/or in the absence of treatment. In embodiments, the disclosed methods of treatment can abate or ameliorate one or more clinical indications of the particular disease being treated. Certain embodiments relating to methods of treating a disease or condition associated with *Chlamydia* infection comprise administration of therapeutically effective amounts of a peptide that inhibits CPAF activity such as, for example, a peptide comprising SEQ ID NO:2, SEQ ID NO:6, or SEQ ID NO:7 as well as pharmaceutical compositions thereof. In embodiments, the method of treating can relate to any method that prevents further progression of the disease and/or symptoms, slows or reduces the further progression of the disease and/or symptoms, or reverses the disease and/or clinical symptoms associated with *Chlamydia* infection, such as are known in the art (see, e.g., Centers for Disease Control and Prevention (CDC) website).

Subjects to be treated by the methods described herein encompass mammalian subjects, including both human subjects and non-human (animal) subjects such as dogs, cats, rabbits, goats, horses, pigs, mice, guinea pigs, cattle, etc. (including both male and female subjects, subjects of all ages including infant, juvenile, adolescent and adult subjects, and pregnant subjects). Subjects may be treated for any purpose, such as for reducing inflammation, inducing immune responses, clearing infected cells, ameliorating chronic disease, etc. The term "concurrently administered" as used herein means that two compounds are administered sufficiently close in time to achieve a combined effect. Concurrent administration may thus be carried out by sequential administration or simultaneous administration (e.g., simultaneous administration in a common, or the same, carrier).

In some embodiments, the disclosed peptides and compositions may be administered by any suitable route of administration, including, but not limited to, injection (subcutaneous, intraperitoneal, intravenous, intramuscular), intranasal, oral, transdermal, parenteral, inhalation, urogenital, nasopharyngeal or transmucosal absorption. Administration encompasses the providing at least one inhibitor of CPAF as described herein (e.g., SEQ ID NO:2, SEQ ID NO:6, or SEQ ID NO:7) formulated as a pharmaceutical composition. Administration of an active agent (e.g., compound, peptide, etc.) is known in the art. Administration also includes targeted delivery wherein one or more inhibitors of CPAF according to the disclosure is active only in a targeted region of the body (for example, in ocular tissue), as well as sustained release formulations in which the inhibitor of CPAF is released over a period of time in a controlled manner. Sustained release formulations and methods for targeted delivery are known in the art and include, for example, use of liposomes, drug loaded biodegradable microspheres, drug-polymer conjugates, drug-specific binding agent conjugates and the like. Pharmaceutically acceptable carriers, vehicles, diluents, and adjuvants are well known to those of skill in the art. Determination of particular pharmaceutical formulations and therapeutically effective amounts and dosing regimen for a given treatment is within the ability of one of skill in the art taking into consideration, for example, patient age, weight, sex, ethnicity, organ (e.g., liver and kidney) function, the extent of desired treatment, the stage and severity of the disease and associated symptoms, and the tolerance of the patient for the treatment.

In embodiments relating to therapeutic applications, the administration can be performed on a subject already suffering from the disorder of interest. Those in the incubation phase or the acute phase of the disease can be treated by the methods described herein, either alone or in conjunction with other treatments, as suitably based on the particular disease/condition, patient, and combination. One of skill in the art will be able to determine when a combination treatment is or is not suitable.

In therapeutic methods and uses, the inhibitors of CPAF and compositions described herein can be administered to a subject in an amount sufficient to treat, or at least partially arrest, symptoms and/or complications. An amount adequate to accomplish this is often referred to as "therapeutically effective dose." Amounts effective for this use will depend in part on the inhibitor, composition, the manner of administration, the stage and severity of the condition being treated, the age, weight, and general health of the patient, and the judgment of the prescribing physician. The timing and interval of administration is varied according to the subject's symptoms, and may be administered at intervals spanning minutes, hours, or days, over a time course of hours, days, weeks or longer, as would be determined by one skilled in the art.

In embodiments, effective amounts of the inhibitors of CPAF and compositions disclosed herein can include about 0.1 µg/kg to up to about 100 mg/kg or more. In other embodiments, the dosage may range from 1 µg/kg up to about 100 mg/kg; or 5 µg/kg up to about 100 mg/kg; or 0.1 µg/kg up to about 50 mg/kg. In some embodiments, the methods, peptides, and compositions described herein can be employed in serious disease states, that is, potential permanent disability or death. In such cases, it is possible and may be felt desirable by the treating physician to administer substantial excesses of these compositions. Additionally, one of ordinary skill in the art would also know how to adjust or modify variables such as dosage, dosage schedules, and routes of administration, as appropriate, for a given subject.

Some embodiments relating to pharmaceutical compositions for therapeutic or prophylactic treatment provide for formulations specific for any of mucosal (oral, nasal, inhalation, rectal, vaginal, tracheal, ocular, etc.), parenteral, topical, or local administration. For purposes herein, mucosal administration is a subcategory of topical administration, as mucosal administration refers to application of a CPAF inhibitor or a composition comprising a CPAF inhibitor to a mucosal surface such as a surface of the respiratory tract, gastrointestinal tract, reproductive tract, eye, urogenital tract, etc. In some embodiments, the pharmaceutical compositions are suitably administered parenterally, e.g., intravenously, subcutaneously, intradermally, or intramuscularly. Topical administration (i.e., non-mucosal) can be to a non-mucosal surface of a subject, such as the ear, nails, hair, or skin, in any appropriate form such as aqueous or non-aqueous liquid (e.g., droplet), emulsion, paste, ointment, cream etc. Thus, the disclosure provides compositions for topical (mucosal or non-mucosal) or parenteral administration which comprise one or more inhibitors of CPAF, dissolved or suspended in an acceptable carrier, such as an aqueous carrier. Any variety of aqueous carriers may be used, e.g., water, buffered water, 0.9% saline, 0.3% glycine, hyaluronic acid and the like. These compositions can be sterilized by conventional, well known sterilization techniques, or may be sterile filtered. The resulting solutions may be packaged for use as is, or lyophilized, the lyophilized preparation being combined with a sterile solution prior to administration. The compositions can contain pharmaceutically acceptable auxiliary substances as required to approximate physiological conditions, such as buffering agents, tonicity adjusting agents, wetting agents and the like, for example, sodium acetate, sodium lactate, sodium chloride, potassium chloride, calcium chloride, sorbitan monolaurate, triethanolamine oleate, etc. Alternatively, the pharmaceutical compositions described herein can also be in dry powder formulations. In embodiments relating to dry powder formulations, typically the liquid is rapidly frozen and dried in a vacuum (e.g., freeze-dried) in the presence of at least one bulking agent (such as trehalose or other sugars) to provide a formulation that has superior temperature stability. Such dry powder formulations may be administered to the host as a dry powder, thereby eliminating the need for liquid reconstitution.

Methods and Assays for Identifying Anti-Chlamydial Agents

In an aspect, the disclosure provides methods of identifying an inhibitor of CPAF, comprising contacting CPAF with a candidate compound in the presence of a CPAF substrate, and measuring cleavage of the CPAF substrate. As described herein, inhibitors of CPAF can function as effective anti-chlamydial agents.

The disclosed methods may be used to test, screen, or evaluate any candidate compound or any group or library of candidate compounds to evaluate or identify one or more inhibitors of CPAF. In some embodiments, the disclosed methods of identifying an inhibitor of CPAF may include in vitro methods. In some embodiments, the disclosed methods of identifying an inhibitor of CPAF may include in vivo methods. In embodiments, the candidate compound or candidate compounds may comprise, for example, peptides, peptidomimetics, small molecules, natural products, and the like. In some embodiments, the candidate compound or candidate compounds may comprise a peptidomimetic or small molecule designed to mimic the physical, chemical, and/or structural features (e.g., relative size/steric hindrance, polar, nonpolar, charged, uncharged, hydropathy index (e.g., hydrophobicity, hydrophilicity), acidic, basic, ability to form bonds (e.g., covalent bonds, hydrogen bonds, van der Waals interactions), etc.) of all or part(s) of SEQ ID NO:2, SEQ ID NO:6, and/or SEQ ID NO:7. In embodiments, the disclosed methods of identifying an inhibitor of CPAF can assess a candidate compound's effectiveness for inhibiting any CPAF activity, such as, for example, CPAF protease activity. In some embodiments, the disclosed methods can measure the effect of a candidate inhibitor of CPAF on CPAF protease activity using model CPAF substrates based on proteins known to be cleaved by CPAF such as, for example, RFX5, vimentin or keratin. In some embodiments, a model CPAF substrate, comprising all or part of a protein known to be cleaved by CPAF, may be synthesized by any method known in the art. Purified CPAF may be produced by any method known in the art, such as, for example, expression of recombinant CPAF in $E.\ coli$.

In some embodiments, the disclosed methods of identifying an inhibitor of CPAF may employ inhibitors of CPAF such as lactacystin, SEQ ID NO:2, and/or SEQ ID NO:7 as positive control inhibitors of CPAF indicating a positive control level of CPAF inhibition and/or a positive control inhibited or reduced level of CPAF activity. In some embodiments, the disclosed methods of identifying an inhibitor of CPAF may employ negative controls lacking a candidate compound or an inhibitor of CPAF for indicating a negative control, baseline, or uninhibited level of CPAF activity or CPAF inhibition. In embodiments, a candidate compound producing a level of CPAF inhibition greater than the negative control or baseline level and/or a CPAF activity below the negative control or baseline level can be considered an inhibitor of CPAF. In embodiments, a candidate compound producing a level of CPAF inhibition comparable to or greater than the positive control level and/or a CPAF activity comparable to or below the positive control level for one or more positive control inhibitors of CPAF (such as, for example, lactacystin, SEQ ID NO:2, SEQ ID NO:7, etc.) can be considered an inhibitor of CPAF.

In some embodiments, the disclosed methods of identifying an inhibitor of CPAF may comprise a high-performance liquid chromatography (HPLC)-based in vitro assay for measuring CPAF activity. A mixture comprising suitable amounts of a model CPAF substrate, purified CPAF, and a candidate compound can be incubated under conditions suitable for the purified CPAF to cleave the model CPAF substrate in the absence of an inhibitor of CPAF. In some embodiments, the mixture may include at least about 0.01 mM, at least about 0.1 mM, at least about 0.5 mM, at least about 1 mM, at least about 2 mM, at least about 3 mM, at least about 4 mM, at least about 5 mM, at least about 6 mM, at least about 7 mM, at least about 8 mM, at least about 9 mM, or at least about 10 mM model CPAF substrate. In some embodiments, the mixture may include at least about 1 nM, at least about 5 nM, at least about 10 nM, at least about 20 nM, at least about 30 nM, at least about 40 nM, at least about 45 nM, at least about 50 nM, at least about 55 nM, at least about 60 nM, at least about 61 nM, at least about 62 nM, at least about 62.5 nM, at least about 63 nM, at least about 64 nM, at least about 65 nM, at least about 70 nM, at least about 75 nM, at least about 80 nM, at least about 90 nM, at least about 100 nM, at least about 150 nM, or at least about 200 nM purified CPAF. In some embodiments, the mixture may include at least about 0.001 µM, at least about 0.005 µM, at least about 0.01 µM, at least about 0.05 µM, at least about 0.1 µM, at least about 0.5 µM, at least about 1 µM, at least about 5 µM, at least about 10 µM, at least about 50 µM, at least about 100 µM, at least about 200 µM, at least about 240 µM, or at least about 500 µM candidate compound. In some embodiments, the model CPAF substrate may comprise a CPAF recognition site from human vimentin protein, such as VRLRSSVPGV (SEQ ID NO:8) or a site recognized for cleavage by CPAF and having at least about 50%, at least about 60%, at least about 70%, at least about 80%, or at least about 90% identity with SEQ ID NO:8. In some embodiments, the model disclosed model CPAF substrates may comprise one or more fluorescent tags, such as, for example, Abz and the like. In some embodiments, the degree of CPAF activity may be evaluated using HPLC to separate and quantify the intact and cleaved model CPAF substrate present in the mixture after incubation with purified CPAF. Any method known in the art may be used to detect and/or quantify the intact model CPAF substrate any cleavage fragments, such as, for example, UV absorbance, detection of one or more fluorescent tags, and the like.

In some embodiments, the disclosed methods of identifying an inhibitor of CPAF may comprise a fluorescence energy resonance transfer (FRET)-based in vitro assay for measuring CPAF activity. A mixture comprising suitable amounts of a model CPAF substrate, purified CPAF, and a candidate compound can be incubated under conditions suitable for the purified CPAF to cleave the model CPAF substrate in the absence of an inhibitor of CPAF. In some embodiments, the model CPAF substrate can comprise one or more suitable fluorescent tags and one or more suitable quenchers incorporated through methods known in the art. In some embodiments, the mixture may include at least about 0.01 mM, at least about 0.1 mM, at least about 0.5 mM, at least about 1 mM, at least about 2 mM, at least about 3 mM, at least about 4 mM, at least about 5 mM, at least about 6 mM, at least about 7 mM, at least about 8 mM, at least about 9 mM, or at least about 10 mM model CPAF substrate. In some embodiments, the mixture may include at least about 1 nM, at least about 5 nM, at least about 10 nM, at least about 20 nM, at least about 30 nM, at least about 40 nM, at least about 45 nM, at least about 50 nM, at least about 55 nM, at least about 60 nM, at least about 61 nM, at least about 62 nM, at least about 62.5 nM, at least about 63 nM, at least about 64 nM, at least about 65 nM, at least about 70 nM, at least about 75 nM, at least about 80 nM, at least about 90 nM, at least about 100 nM, at least about 150 nM, or at least about 200 nM purified CPAF. In some embodiments, the mixture may include at least about 0.001 µM, at least about 0.005 µM, at least about 0.01 µM, at least about 0.05 µM, at least about 0.1 µM, at least about 0.5 µM, at least about 1 µM, at least about 5 µM, at least about 10 µM, at least about 50 µM, at least about 100 µM, at least about 200 µM, at least about 240 µM, or at least about 500 µM candidate compound. In some embodiments, the model CPAF substrate may comprise a CPAF recognition site from human vimentin protein, such as VRLRSSVPGV (SEQ ID NO:8) or a site recognized for cleavage by CPAF and having at least about 50%, at least about 60%, at least about 70%, at least about 80%, or at least about 90% identity with SEQ ID NO:8. In some embodiments, the model disclosed model CPAF substrates may comprise one or more fluorescent tags such as, for example, Abz, and one or more quenchers, such as, for example, 3-nitrotyrosine and the like. In some embodiments, the degree of CPAF activity may be evaluated by measuring fluorescence of the fluorescent tag to detect and quantify the extent of model CPAF substrate cleavage after incubation with purified CPAF. In some embodiments, the disclosed FRET-based assays can provide rapid, scalable, and facile screening of candidate compounds and can be used for large-scale screening of many candidate compounds.

In an aspect, the disclosure provides methods of identifying an inhibitor of CPAF, comprising contacting a Chlamydia-infected cell with a candidate compound, and monitoring the cell for one or more indicators of CPAF inhibition.

In some embodiments, the disclosed methods of identifying an inhibitor of CPAF may comprise an in vivo assay for measuring CPAF activity. In some embodiments, the disclosed methods may comprise contacting a first Chlamydia-infected cell with a candidate compound and monitoring the cell for one or more indicators of CPAF inhibition. In embodiments, the Chlamydia-infected cell may be any suitable cultured mammalian cell such as, for example, mouse lung fibroblasts, HeLa cells, McCoy cells, monkey kidney cells, Hep2 cells, primary cervical epithelial cells, and the like infected through methods known in the art with any suitable member of the Chlamydiae, such as, for example, C. trachomatis, C. pneumoniae, C. muridarum, and C. caviae, and including reference strains and clinical isolates thereof. In some embodiments, the indicators of CPAF inhibition can be any detectable phenotypic, biochemical, immunological, or other process, change, or outcome observed in a Chlamydia-infected cell (or in a Chlamydia cell) that differs in timing, occurrence, extent, or degree between Chlamydia-infected cells and Chlamydia-infected cells that have been contacted with an inhibitor of CPAF. In some embodiments, indicators of CPAF inhibition can include, for example, disruption of inclusion membranes; inclusion structure collapse; loss of cytoskeletal reorganization (such as, for example, vimentin reorganization); aggregation of one or more inclusion membrane markers (such as IncA and/or Cap1); production of one or more cytokines, chemokines, or other immune mediators (such as, for example, IL-8 secretion); nuclear condensation; caspase activity (such as, for example, caspase-1 activity); apoptosis; cleavage of one or more CPAF substrates; reduced inclusion growth; reduced EB yield; and the like. In some embodiments, the disclosed in vivo assays for identifying an inhibitor of CPAF may employ inhibitors of CPAF such as lactacystin, SEQ ID NO:2, and/or SEQ ID NO:7 as baseline or positive control inhibitors of CPAF. In some embodiments, the disclosed in vivo assays for identifying an inhibitor of CPAF may employ a control or negative control Chlamydia-infected cell that is not contacted with a candidate compound or an inhibitor of CPAF for providing negative or baseline indicators of CPAF inhibition. In embodiments, more frequent, more pronounced, more extensive, or a greater magnitude of one or more indicators of CPAF inhibition in the first Chlamydia-infected cell relative to the negative control Chlamydia-infected cell indicates that the candidate compound is an inhibitor of CPAF.

While the following examples provide further detailed description of certain aspects and embodiments of the disclosure, they should be considered merely illustrative of those aspects and embodiments, and not in any way limiting to the scope of the disclosure.

EXAMPLES

Example 1

Cell Culture, Infection, Immunodetection, and Microscopy Methods

Mouse lung fibroblasts (MLF) from ASC−/−, ICE−/−, and wild type mice were isolated using standard techniques (see, e.g., van Deventer et al., Am. J. Pathol., 173:253-264 (2008)). Ex vivo lungs were minced, incubated with 1 mg/ml collagenase A and 0.02 mg/ml DNAse I in RPMI supplemented with 2% fetal calf serum (FBS) for 45 minutes at 37° C. Digested lungs were filtered and washed with 1×PBS. Red blood cells were lysed in ACK lysis buffer for 2 minutes. Single cell suspensions were seeded in DMEM supplemented with 10% FBS, L-glutamine, non-essential amino acids, and antibiotics. Cultured MLFs were immortalized by transformation with t-antigen and telomerase. HeLa cells (ATCC) and MLFs were maintained in DMEM supplemented with 10% FBS (CellGro Mediatech Inc). C. trachomatis strain LGV-L2 434/Bu was propagated in HeLa cells using techniques familiar in the art (see, e.g., Caldwell et al., Infect. Immun., 31:1161-1176 (1981)). EBs were added to HeLa cells at indicated MOIs and infections were synchronized by centrifugation at 300×g for 30 minutes at 4° C.

Table 3 contains a detailed list of antibodies used in the disclosed Examples:

TABLE 3

Summary of Antibody and Antisera Sources

| Host | Protein | Source |
|---|---|---|
| mouse monoclonal | Phosphotyrosine | Cell Signaling |
| rabbit polycloncal | Bim | Cell Signaling |
| rabbit polycloncal | Caspase-3 | Cell Signaling |
| mouse monoclonal | GFP | StressGen |
| rabbit monoclonal | GAPDH | Abcam |
| rabbit polyclonal | Puma | Abcam |
| mouse monoclonal | Tubulin | Sigma |
| mouse monoclonal | IncA | D. Rockey (Oregon State University) |
| rabbit polycloncal | RpoD | M. Tan (University of California, Irvine) |
| rabbit polycloncal | LGV-L2 | P. Bavoil (University of Maryland) |
| mouse monoclonal | Chlamydia LPS | H. Caldwell (RML/NIH) |
| mouse monoclonal | MOMP | H. Caldwell (RML/NIH) |
| rabbit polycloncal | Ct005 | R. Valdivia (Duke University) |
| rabbit polycloncal | IncD | R. Valdivia (Duke University) |
| rabbit polycloncal | IncC | R. Valdivia (Duke University) |
| rabbit polycloncal | CPAF | R. Valdivia (Duke University) |
| rabbit polycloncal | TARP | R. Valdivia (Duke University) |
| rabbit polycloncal | IncG | T. Hackstadt (NIAID) |
| rabbit polycloncal | Na/K ATPase | Hybridoma Bank, University of Iowa |
| rabbit polycloncal | Cap1 | A. Subtil (Institut Pasteur) |

Rabbits were immunized with recombinant GST fusions to Ct005, IncC, IncD, Tarp, and hexa-histidine-tagged CPAF produced in E. coli BL-21 (available from Stratagene) and purified by affinity chromatography. IgG antibodies were purified with Protein A-coated Sepharose beads (available from GE Healthcare). Membrane-associated Chlamydial proteins were harvested from infected HeLa by ultracentrifugation of whole cell lysates on an Optiprep (Sigma) discontinuous density gradient (25, 20, 17.5, 15, 12.5, 10%) and assessing the fractionation of IncA and IncG positive membranes by immunoblot analysis. To assess CPAF cleavage of membrane proteins and EB proteins, purified membranes and soluble EB protein lysate were incubated with 6× his-CPAF at 37° C., and resulting product analyzed by immunoblot. To assess CPAF-dependent cleavage during infection, HeLa cells were infected with LGV-L2 at an MOI of 1, treated with CPAF inhibitor (SEQ ID NO:7) or control peptide (SEQ ID NO:11) at 12 hours post-infection and harvested at 30 hours post-infection.

For routine indirect immunofluorescence, HeLa cells were grown on glass coverslips and infected with *Chlamydia* at an MOI of 1. At the indicated times post-infection, cells were fixed with cold 3% formaldehyde, permeabilized with 0.1% Tx-100, blocked in 2% bovine serum albumin (BSA), and incubated with primary antibody followed by secondary fluorophore-conjugated anti-rabbit or anti-mouse IgG (available from Molecular Probes). Host and Chlamydial DNA were stained with 1 µM Hoechst (available from Invitrogen). Infected cells were imaged with a Zeiss Axioscope epifluorescence microscope and Axiovision v3.0 software on a Leica TCS SL confocal microscope and processed with Leica software. For transmission electron midt6scopy (TEM), HeLa cells grown on thermanox coverslips (Electron Microscopy Services) were fixed with 0.05% malachite green/2.5% gluteraldehyde, post-fixed with 0.8% osmium tetroxide and 1% tannic acid and 1% uranyl acetate. Following dehydration of samples, sections were post-stained and imaged with a Tecnai $G^{12}$ Twin electron microscope (available from FEI).

Example 2

Protein and Peptide Synthesis

Recombinant CPAF was expressed and purified to homogeneity from *E. coli* BL21 (DE3) cells harboring the pET30b-CPAF plasmid. Briefly, cells were grown in Luria broth at 37° C. with 50 µg/mL kanamycin to an OD580 of 0.6. IPTG (0.3 mM) was added to induce expression of CPAF, and cells were incubated at 15° C. until harvested after 15 h. Cells were resuspended in 150 mM NaCl, 50 mM Tris, 10 mM imidazole (pH 7.5) and lysed using an EmulsiFlex-05 high-pressure homogenizer (available from Avestin, Inc). The resultant lysate was clarified by ultra centrifugation and applied to a chelating Sepharose fast flow column (available from GE Healthcare). The column was washed first with 10 mM imidazole, 150 mM NaCl, 0.1% triton x-100 followed by 60 mM imidazole, 150 mM NaCl, 50 mM Tris pH 7.5, and finally 60 mM imidazole, 150 mM NaCl, 0.1% triton x-100, finished by an elution using a linear gradient from 60 mM imidazole to 500 mM imidazole in 150 mM NaCl and 50 mM Tris (pH 7.5). Fractions containing CPAF were pooled, concentrated, and loaded onto a HiPrep 26/60 Sephacryl S-200 gel filtration column (available from GE Healthcare) previously equilibrated with 150 mM NaCl and 50 mM Tris (pH 7.5). Fractions containing pure CPAF were concentrated an Amicon spin column concentrator (available from Millipore) to a concentration of 1 mg/mL, determined using the calculated molar extinction coefficient € 280=77997 $M^{-1}$ $cm^{-1}$.

Standard Fmoc amino acids (Anaspec, Novabiochem) and Boc-anthranilic acid (Boc-Abz) (Bachem) were purchased and used without further purification. 4-(2',4'-Dimethoxyphenyl-Fmoc-aminomethyl)-phenoxy (Rink) resin SS (Advanced Chemtech) was used for solid-phase peptide synthesis. All peptides (SEQ ID NOs: 2, 7-10) were synthesized using standard Fmoc/piperidine solid-phase strategy with RINK amide resin on a 0.25 mmol scale using a CEM Liberty synthesizer. Peptides were cleaved using a TFA/H2O/TIS/EDT mixture (95:2.5:2.5) for 30 min using the Discovery microwave (36° C., 36 W, 30 min) Excess TFA was removed by rotary evaporation, and the peptides were precipitated using cold diethyl ether, filtered using a fine porosity frilled glass filter, dissolved in water, and lyophilized to afford the desired crude peptide product. Peptides were purified by HPLC using a Vydac reverse-phase C8 preparative column to >96% purity and confirmed for composition by mass spectrometry. Purified peptides were lyophilized and stored desiccated at −20° C.

Example 3

A Subset of Chlamydial Effector Proteins is Sensitive to Proteolysis

Figure 3:
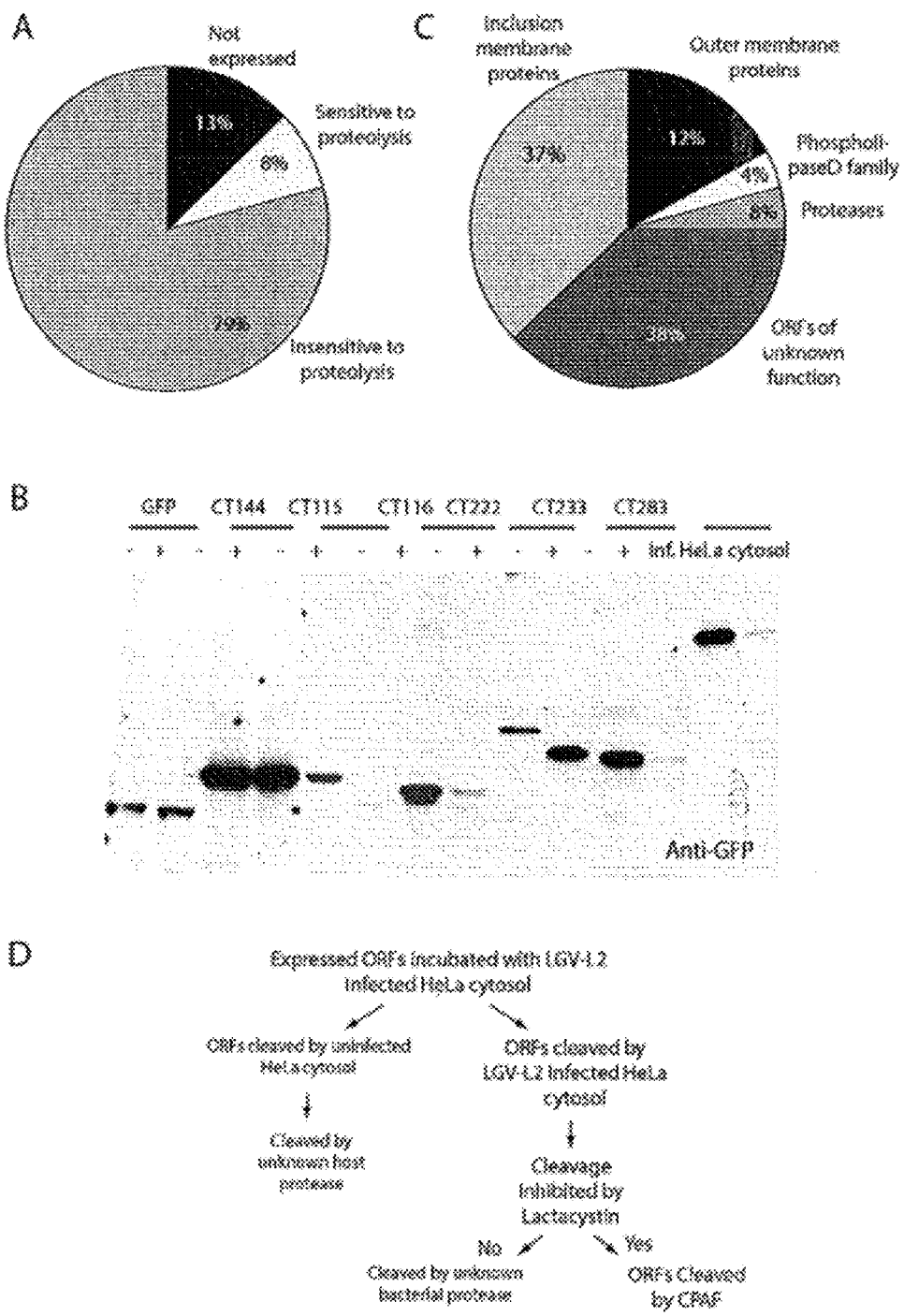
FIG. 3 depicts the results of a systematic screen of chlamydial proteins for protease sensitivity. (A) *C. trachomatis* ORFs (n=309) were cloned into either yeast or *E. coli* expression vectors (see Table 1 and Sisko, et al., *Mol. Microbiol.* 60:51-66 (2008)), and crude protein extracts were tested for proteolytic processing of the recombinant proteins after incubation with cytosols derived from *Chlamydia*-infected or uninfected HeLa cells. Twenty-five chlamydial proteins (8%) were sensitive to proteolysis (see Table 2). (B) Representative immunoblot analysis of GFP-tagged chlamydial proteins expressed in yeast that are cleaved after incubation with cytosols from *Chlamydia*-infected cells. Recombinant proteins were identified with an anti-GFP antibody. Ct144 and free GFP were included as negative controls. (C) Protease-sensitive chlamydial proteins (n=25) consisted of *Chlamydia*-specific proteins of unknown function, inclusion membrane proteins, outer membrane proteins, proteases, and phospholipase D-like proteins. (D) An approach to screening for putative CPAF substrates based on sensitivity of observed processing to protease-inhibitors.

Recombinant *Chlamydia* ORFs were tested for sensitivity to host and *Chlamydia*-derived proteases. Approximately 10% of the *Chlamydia* genome encodes proteins that access the cytoplasm of the infected host cell. A panel of recombinant *Chlamydia* proteins (~30% of the genome) were tested for sensitivity to proteolysis after incubation with lysates from *Chlamydia*-infected and uninfected HeLa cells (FIG. 3).

*C. trachomatis* ORFs cloned into the yeast expression vector pSDY8 (Sisko, et al., *Mol. Microbiol.*, 60:51-66 (2006)) or the *E. coli* expression vector pGEX-4T-1 (available from GE Healthcare) are listed in Table 1. *Chlamydia* ORFs were amplified from *C. trachomatis* serovar D genome using the Expand High Fidelity PCR kit (available from Roche).

TABLE 1

Amplification and Cloning of Chlamydia ORFs.

| Vector | CT# | FL (bp) | Cloned (bp) | N-terminal primer | C-terminal primer |
|---|---|---|---|---|---|
| pSDY8 | CT047 | 942 | FL | CGTCAAGGAGAAAAAACC CCGGATTCTAGAACTAGTA TGGGAAACAGCCAGAAT (SEQ ID NO: 12) | TCCAGTGAAAAGTTCTTCT CCTTTACTCATAAGCTTAA GTCGTGAAACTAGCAT (SEQ ID NO: 13) |
| pSDY8 | CT065 | 1548 | FL | CGTCAAGGAGAAAAAACC CCGGATTCTAGAACTAGTA TGACTCAAACCGCGGAA (SEQ ID NO: 14) | TCCAGTGAAAAGTTCTTCT CCTTTACTCATAAGCTTAG AAACACCTTCTATAGC (SEQ ID NO: 15) |
| pSDY8 | CT101 | 462 | 163-459 | CGTCAAGGAGAAAAAACC CCGGATTCTAGAACTAGTA TGTCTATCAAACATCGC (SEQ ID NO: 16) | TCCAGTGAAAAGTTCTTCT CCTTTACTCATAAGCTTTC AGTAATAATAAAC (SEQ ID NO: 17) |

TABLE 1-continued

Amplification and Cloning of Chlamydia ORFs.

| Vector | CT# | FL (bp) | Cloned (bp) | N-terminal primer | C-terminal primer |
|---|---|---|---|---|---|
| pSDY8 | CT135a | 1083 | 1-378 | CGTCAAGGAGAAAAAACC CCGGATTCTAGAACTAGTA TGGTAAGCTTCGATTTA (SEQ ID NO: 18) | TCCAGTGAAAAGTTCTTCT CCTTTACTCATAAGCTTTA CGCAACTCATCAT (SEQ ID NO: 19) |
| pSDY8 | CT135b | 1083 | 795-1083 | CGTCAAGGAGAAAAAACC CCGGATTCTAGAACTAGTA TGGTTTCCGGAATCTGC (SEQ ID NO: 20) | TCCAGTGAAAAGTTCTTCT CCTTTACTCATAAGCTTTT ACTCTATACGCGA (SEQ ID NO: 21) |
| pSDY8 | CT196 | 321 | FL | CCCACTAGTATGCGCCCTC TCTTCTCT (SEQ ID NO: 22) | CCCAAGCTTTTAATCGCA AGAGAT (SEQ ID NO: 23) |
| pSDY8 | CT232 | 345 | 193-345 | CCCACTAGTAACACCGTAA CTATTG (SEQ ID NO: 24) | CCCAAGCTTTTCTTGAGGT TTTGTTG (SEQ ID NO: 25) |
| pSDY8 | CT241 | 2376 | FL | CGTCAAGGAGAAAAAACC CCGGATTCTAGAACTAGTA TGCTTGGAATACGCAAA (SEQ ID NO: 26) | TCCAGTGAAAAGTTCTTCT CCTTTACTCATAAGCTTGA ATACTCCTCCCAAGGC (SEQ ID NO: 27) |
| pSDY8 | CT242 | 522 | FL | CCCACTAGTAAAAAGTTCT TATTAC (SEQ ID NO: 28) | CCCACTAGTTTAATTATTT TGAAA (SEQ ID NO: 29) |
| pSDY8 | CT251 | 2361 | FL | CGTCAAGGAGAAAAAACC CCGGATTCTAGAACTAGTA TGAGAATGAATAAACGA (SEQ ID NO: 30) | TCCAGTGAAAAGTTCTTCT CCTTTACTCATAAGCTTTC TCTTCTTATTGATAAT (SEQ ID NO: 31) |
| pSDY8 | CT283 | 2097 | 73-2097 | CCCACTAGTATCGCTGGCG TTTGT (SEQ ID NO: 32) | CCCACTAGTTTAACTAGG GTTGTG (SEQ ID NO: 33) |
| pSDY8 | CT300 | 348 | FL | CCCACTAGTATGTTACGAT ACTTATAT (SEQ ID NO: 34) | CCCAAGCTTTTAGATTTCG ATTTG (SEQ ID NO: 35) |
| pSDY8 | CT345a | 366 | 1-105 | CCCACTAGTATGCAACTTC CGTCTATT (SEQ ID NO: 36) | CCCAAGCTTAGCTATATTG ATGAT (SEQ ID NO: 37) |
| pSDY8 | CT345b | 366 | 247-366 | CCCACTAGTATGCCGGATA TTGAAAAA (SEQ ID NO: 38) | CCCAAGCTTCTAATGAGC TGCTTT (SEQ ID NO: 39) |
| pSDY8 | CT357 | 330 | FL | CCCACTAGTATGTCCTCAT CAACCAAG (SEQ ID NO: 40) | CCCAAGCTTTTATTGTTGT TTCTT (SEQ ID NO: 41) |
| pSDY8 | CT371 | 783 | FL | CGTCAAGGAGAAAAAACC CCGGATTCTAGAACTAGTA TGCGTCTTTGTTTTATT (SEQ ID NO: 42) | TCCAGTGAAAAGTTCTTCT CCTTTACTCATAAGCTTCT TATCTAGCCTGTGACG (SEQ ID NO: 43) |
| pSDY8 | CT412 | 2925 bp | 1-2025 | CGTCAAGGAGAAAAAACC CCGGATTCTAGAACTAGTA TGGTTTTTGTTTAGTATTG (SEQ ID NO: 44) | TCCAGTGAAAAGTTCTTCT CCTTTACTCATAAGCTTGC CAACATAGCCTCC (SEQ ID NO: 45) |
| pSDY8 | CT413 | 5253 bp | 1-4353 | CGTCAAGGAGAAAAAACC CCGGATTCTAGAACTAGTA TGGTTAATTAGTGGTAC (SEQ ID NO: 46) | TCCAGTGAAAAGTTCTTCT CCTTTACTCATAAGCTTGA TCATGCGAGCACC (SEQ ID NO: 47) |
| pSDY8 | CT440 | 339 | FL | CCCACTAGTATGGCTCTTA TCTAT (SEQ ID NO: 48) | CCCAAGCTTTTATTTTTCT TTTGT (SEQ ID NO: 49) |
| pSDY8 | CT441 | 1932 | FL | TCCAGTGAAAAGTTCTTCT CCTTTACTCATAAGCTTTG ATATAGATTTTAGAAGGAT (SEQ ID NO: 50) | CGTCAAGGAGAAAAAACC CCGGATTCTAGAACTAGT ATGATGAGATTCGCTCGC TTT (SEQ ID NO: 51) |
| pSDY8 | CT442 | 450 | FL | CGTCAAGGAGAAAAAACC CCGGATTCTAGAACTAGTA TGAGCACTGTACCCGTT (SEQ ID NO: 52) | TCCAGTGAAAAGTTCTTCT CCTTTACTCATAAGCTTTT GGGTCTGATCCACCAG (SEQ ID NO: 53) |

TABLE 1-continued

Amplification and Cloning of Chlamydia ORFs.

| Vector | CT# | FL (bp) | Cloned (bp) | N-terminal primer | C-terminal primer |
|---|---|---|---|---|---|
| pSDY8 | CT443 | 1659 | FL | CGTCAAGGAGAAAAAACC CCGGATTCTAGAACTAGTA TGCGAATAGGAGATCCT (SEQ ID NO: 54) | TCCAGTGAAAAGTTCTTCT CCTTTACTCATAAGCTTAT AGATGTGTATTCTC (SEQ ID NO: 55) |
| pSDY8 | CT444 | 264 | FL | CGTCAAGGAGAAAAAACC CCGGATTCTAGAACTAGTA TGAAAAAAACTGCTTTA (SEQ ID NO: 56) | TCCAGTGAAAAGTTCTTCT CCTTTACTCATAAGCTTTT GTCTGCATTTGCCGTC (SEQ ID NO: 57) |
| pSDY8 | CT449 | 330 | 271-330 | CCCACTAGTGCTAATATGC GTCTTC (SEQ ID NO: 58) | CCCACTAGTCTGAATAGG CGCTTC (SEQ ID NO: 59) |
| pSDY8 | CT483a | 366 | 1-111 | CCCACTAGTATGGATTTTA TGTCTGTT (SEQ ID NO: 60) | CCCAAGCTTTTCGTATCGA GCGCG (SEQ ID NO: 61) |
| pSDY8 | CT483b | 366 | 313-363 | CCCACTAGTATGGTACAGC AGGAAACG (SEQ ID NO: 62) | CCCAAGCTTCTACGGGGT AGTAGC (SEQ ID NO: 63) |
| pSDY8 | CT559 | 978 | FL | CGTCAAGGAGAAAAAACC CCGGATTCTAGAACTAGTA TGTTTCGTTATACTCTT (SEQ ID NO: 64) | TCCAGTGAAAAGTTCTTCT CCTTTACTCATAAGCTTAG CGTCCTCGTTATTCTC (SEQ ID NO: 65) |
| pSDY8 | CT600 | 564 | FL | CGTCAAGGAGAAAAAACC CCGGATTCTAGAACTAGTA TGAGAAAGACTATTTTT (SEQ ID NO: 66) | TCCAGTGAAAAGTTCTTCT CCTTTACTCATAAGCTTGC GAGCATGGATCTTAAA (SEQ ID NO: 67) |
| pSDY8 | CT634 | 1395 | FL | CGTCAAGGAGAAAAAACC CCGGATTCTAGAACTAGTA TGAAAATAGTTGTTTCT (SEQ ID NO: 68) | TCCAGTGAAAAGTTCTTCT CCTTTACTCATAAGCTTCG AGGAGGTTACCACATT (SEQ ID NO: 69) |
| pSDY8 | CT681 | 1179 | FL | CGTCAAGGAGAAAAAACC CCGGATTCTAGAACTAGTA TGAAAAAACTCTTGAAA (SEQ ID NO: 70) | TCCAGTGAAAAGTTCTTCT CCTTTACTCATAAGCTTGA AGCGGAATTGTGCATT (SEQ ID NO: 71) |
| pSDY8 | CT705 | 1257 | FL | CGTCAAGGAGAAAAAACC CCGGATTCTAGAACTAGTA TGACAAAAAAAAATC (SEQ ID NO: 72) | TCCAGTGAAAAGTTCTTCT CCTTTACTCATAAGCTTAG CAATCGCCTCTGG (SEQ ID NO: 73) |
| pSDY8 | CT713 | 1020 | FL | CGTCAAGGAGAAAAAACC CCGGATTCTAGAACTAGTA TGAGTAGCAAGCTAGTG (SEQ ID NO: 74) | TCCAGTGAAAAGTTCTTCT CCTTTACTCATAAGCTTGA ATTGGAATCCTCCGGA (SEQ ID NO: 75) |
| pSDY8 | CT789 | 249 | FL | CCCACTAGTATTTCAAATA TAGAA (SEQ ID NO: 76) | CCCACTAGTCTTTTGCTTA GGATG (SEQ ID NO: 77) |
| pSDY8 | CT797 | 606 | FL | CGTCAAGGAGAAAAAACC CCGGATTCTAGAACTAGTA TGAGAGTGAGCTTACCA (SEQ ID NO: 78) | TCCAGTGAAAAGTTCTTCT CCTTTACTCATAAGCTTTG ACTCGCCATCCGGCGA (SEQ ID NO: 79) |
| pSDY8 | CT812 | 4593 | 1-3693 bp | CGTCAAGGAGAAAAAACC CCGGATTCTAGAACTAGTA TGGATTCCAACTAATGAC (SEQ ID NO: 80) | TCCAGTGAAAAGTTCTTCT CCTTTACTCATAAGCTTAA AGATCAATCGCAATCC (SEQ ID NO: 81) |
| pSDY8 | CT823 | 1491 | FL | CGTCAAGGAGAAAAAACC CCGGATTCTAGAACTAGTA TGATGAAAAGATTAT (SEQ ID NO: 82) | TCCAGTGAAAAGTTCTTCT CCTTTACTCATAAGCTTCT CGTCTGATTTCAAG (SEQ ID NO: 83) |
| pSDY8 | CT841 | 2739 | FL | CGTCAAGGAGAAAAAACC CCGGATTCTAGAACTAGTA TGGCTAAAGATAAA (SEQ ID NO: 84) | TCCAGTGAAAAGTTCTTCT CCTTTACTCATAAGCTTTG TGCTAGTATTAAAC (SEQ ID NO: 85) |

TABLE 1-continued

Amplification and Cloning of Chlamydia ORFs.

| Vector | CT# | FL (bp) | Cloned (bp) | N-terminal primer | C-terminal primer |
|---|---|---|---|---|---|
| pSDY8 | CT852 | 612 | FL | CGTCAAGGAGAAAAAACC CCGGATTCTAGAACTAGTA TGCTACATTCACTATTT (SEQ ID NO: 86) | TCCAGTGAAAAGTTCTTCT CCTTTACTCATAAGCTTAG GTGTAACATAATACCC (SEQ ID NO: 87) |
| pSDY8 | CT853 | 597 | FL | CGTCAAGGAGAAAAAACC CCGGATTCTAGAACTAGTA TGGACTGGTCATTTTTT (SEQ ID NO: 88) | TCCAGTGAAAAGTTCTTCT CCTTTACTCATAAGCTTTA GGAAAGTTTGTTGTAG (SEQ ID NO: 89) |
| pSDY8 | CT869 | 2892 | 1-1992 bp | CGTCAAGGAGAAAAAACC CCGGATTCTAGAACTAGTA TGGCCCGGCAGGAAGCC (SEQ ID NO: 90) | TCCAGTGAAAAGTTCTTCT CCTTTACTCATAAGCTTGA ATCGCAGAGCAATTTC (SEQ ID NO: 91) |
| pSDY8 | CT870 | 3102 | 1-2202 bp | CGTCAAGGAGAAAAAACC CCGGATTCTAGAACTAGTA TGGTGTTTGGTAATCG (SEQ ID NO: 92) | TCCAGTGAAAAGTTCTTCT CCTTTACTCATAAGCTTAA AGACCAGAGCTCCTCC (SEQ ID NO: 93) |
| pSDY8 | CT871 | 3039 | 1-2139 bp | CGTCAAGGAGAAAAAACC CCGGATTCTAGAACTAGTA TGGTATTTGCTGTATTAG (SEQ ID NO: 94) | TCCAGTGAAAAGTTCTTCT CCTTTACTCATAAGCTTGA ACC GGAC TTTACTTCC (SEQ ID NO: 95) |
| pSDY8 | CT872 | 3048 | 1-2148 bp | CGTCAAGGAGAAAAAACC CCGGATTCTAGAACTAGTA TGGCCATTAGTAAAGGTTC (SEQ ID NO: 96) | TCCAGTGAAAAGTTCTTCT CCTTTACTCATAAGCTTAA AGATTCTATTCAAGCC (SEQ ID NO: 97) |
| pSDY8 | CT874 | 2634 | 1-1734 bp | CGTCAAGGAGAAAAAACC CCGGATTCTAGAACTAGTA TGGATGGTCATCTAAACTG (SEQ ID NO: 98) | TCCAGTGAAAAGTTCTTCT CCTTTACTCATAAGCTTGA ACCTGTAAGTGGTCCC (SEQ ID NO: 99) |
| pGEX 4T-1 | CT005 | 1089 | FL | CTTACTAGTATGACTCCAG TAACACCA (SEQ ID NO: 100) | CTTAAGCTTTTTACGAGAG GGTTTCTT (SEQ ID NO: 101) |
| pGEX 4T-1 | CT005 | 1089 | 85-363 | CTTACTAGTATGGAATCCC AGAAAAGT (SEQ ID NO: 102) | CTTAAGCTTTTTACGAGAG GGTTTCTT (SEQ ID NO: 103) |
| pGEX 4T-1 | CT005 | 1089 | 212-363 | CTTACTAGTATGTACACCT ATTCCGTT (SEQ ID NO: 104) | CTTAAGCTTTTTACGAGAG GGTTTCTT (SEQ ID NO: 105) |
| pGEX 4T-1 | CT005 | 1089 | 255-363 | CTTACTAGTATGGAATCCT CCTCTTCT (SEQ ID NO: 106) | CTTAAGCTTTTTACGAGAG GGTTTCTT (SEQ ID NO: 107) |
| pGEX 4T-1 | CT089 | 1266 | FL | CTTACTAGTATGACTGCAT CAGGAGGAGC (SEQ ID NO: 108) | CTTACTAGTTTAGGGTGAT GGAGG (SEQ ID NO: 109) |
| pGEX 4T-1 | CT101 | 462 | 55-153 | CTTACTAGTATGTCTATCA AACATCGC (SEQ ID NO: 110) | CTTAAGCTTTCAGTAATAA TAAAC (SEQ ID NO: 111) |
| pGEX 4T-1 | CT105 | 1971 | FL | Subcloned from pSDY8 | |
| pGEX 4T-1 | CT115 | 423 | 310-363 | CCCACTAGTATGTCTCCGA AAACGACA (SEQ ID NO: 112) | CTTAAGCTTTTTACGAGAG GGTTTCTT (SEQ ID NO: 113) |
| pGEX 4T-1 | CT115 | 423 | .1-40 | CCCCATATGATGACTAAGG TTTATGCGA (SEQ ID NO: 114) | CTTAAGCTTAACTGCCACC AATCTTTT (SEQ ID NO: 115) |
| pGEX 4T-1 | CT115 | 423 | 93-141 | CCCCATATGACAGAAGCTG TGACT (SEQ ID NO: 116) | CTTAAGCTTCTCACCGAGT TTACGAGT (SEQ ID NO: 117) |
| pGEX 4T-1 | CT116 | 396 | 99-132 | Subcloned from pSDY8 | |
| pGEX 4T-1 | CT134 | 414 | 99-132 | Subcloned from pSDY8 | |

TABLE 1-continued

Amplification and Cloning of Chlamydia ORFs.

| Vector | CT# | FL (bp) | Cloned (bp) | N-terminal primer | C-terminal primer |
|---|---|---|---|---|---|
| pGEX 4T-1 | CT135 | 1083 | 266-360 | CTTACTAGTATGGTTTCCG GAATCTGC (SEQ ID NO: 118) | CTTAAGCTTTTACTCTTAT ACGCGC (SEQ ID NO: 119) |
| pGEX 4T-1 | CT142 | 858 | FL | Subcloned from pSDY8 | |
| pGEX 4T-1 | CT159 | 933 | FL | Subcloned from pSDY8 | |
| pGEX 4T-1 | CT196 | 321 | 87-106 | Subcloned from pSDY8 | |
| pGEX 4T-1 | CT214 | 1641 | 100-547 | CCACTAGTTTCTTGAGTAG TGGTC (SEQ ID NO: 120) | CCCACTAGTACCAAATAA TGCAGGTAG (SEQ ID NO: 121) |
| pGEX 4T-1 | CT222 | 387 | 89-129 | Subcloned from pSDY8 | |
| pGEX 4T-1 | CT223 | 813 | 86-270 | Subcloned from pSDY8 | |
| pGEX 4T-1 | CT225 | 369 | FL | Subcloned from pSDY8 | |
| pGEX 4T-1 | CT233 | 810 | .1-97 | Subcloned from pSDY8 | |
| pGEX 4T-1 | CT260 | 489 | FL | Subcloned from pSDY8 | |
| pGEX 4T-1 | CT283 | 2094 | 24-698 | CCCACTAGTATATCGCTGGCG TTTGT (SEQ ID NO: 122) | CCCACTAGTTTAACTAGG GTTGTG (SEQ ID NO: 123) |
| pGEX 4T-1 | CT288 | 1689 | FL | Subcloned from pSDY8 | |
| pGEX 4T-1 | CT300 | 348 | 92-115 | CTTACTAGTATGTTACGAT ACTTATAT (SEQ ID NO: 124) | CTTACTAGTATGTTAGATT TCGATTTG (SEQ ID NO: 125) |
| pGEX 4T-1 | CT301 | 934 | FL | Subcloned from pSDY8 | |
| pGEX 4T-1 | CT345 | 366 | .1-35 | CTTACTAGTATGCAACTTC CGTCTATTATT (SEQ ID NO: 126) | CTTAAGCTTCTAATGAGCT GCTTT (SEQ ID NO: 127) |
| pGEX 4T-1 | CT357 | 333 | 87-110 | CTTACTAGTATGTCCTCAT CAACCAAG (SEQ ID NO: 128) | CTTAAGCTTTTATTGTTGT TTCTT (SEQ ID NO: 129) |
| pGEX 4T-1 | CT383A | 732 | 1-101 | Subcloned from pSDY8 | |
| pGEX 4T-1 | CT383B | 732 | 88-264 | Subcloned from pSDY8 | |
| pGEX 4T-1 | CT423 | 1110 | FL | Subcloned from pSDY8 | |
| pGEX 4T-1 | CT440 | 339 | 81-112 | CTTACTAGTATGAAAGTTG TTGTGAAT (SEQ ID NO: 130) | CTTAAGCTTTTATTTTTCT TTTGT (SEQ ID NO: 131) |
| pGEX 4T-1 | CT483 | 366 | .1-37 | CTTACTAGTATGGATTTTA TGTCTGTT (SEQ ID NO: 132) | CTTAAGCTTTTCGTATCGA GCGCG (SEQ ID NO: 133) |
| pGEX 4T-1 | CT483 | 366 | 105-121 | CTTACTAGTATGGTACAGC AGGAAACG (SEQ ID NO: 134) | CTTAAGCTTCTACGGGGT AGTAGC (SEQ ID NO: 135) |

TABLE 1-continued

Amplification and Cloning of Chlamydia ORFs.

| Vector | CT# | FL (bp) | Cloned (bp) | N-terminal primer | C-terminal primer |
|---|---|---|---|---|---|
| pGEX 4T-1 | CT559 | 981 | FL | Subcloned from pSDY8 | |
| pGEX 4T-1 | CT618 | 801 | .1-96 | GTCGGATCCATTATGGCAG CAACG (SEQ ID NO: 136) | GAGTGCGGCCGCACCGGT TAGTAATTGTAC (SEQ ID NO: 137) |
| pGEX 4T-1 | CT632 | 1587 | FL 1-529 | Subcloned from pSDY8 | |
| pGEX 4T-1 | CT712 | 1170 | FL | CCCACTAGTATGAGAAACC ATCCGATTCCAG (SEQ ID NO: 138) | CCCAAGCTTGCTAGAAGC CAATGTTC (SEQ ID NO: 139) |
| pGEX 4T-1 | CT695 | 1194 | FL | CCCACTAGTAGTAGCATAA GCCCTATAG (SEQ ID NO: 140) | CCCACTAGTGATATTCCCA ACCGAAGAAG (SEQ ID NO: 141) |
| pGEX 4T-1 | CT806A | 2868 | 1-478 | CCCACTAGTATGGACAACC ACCCTCCTG (SEQ ID NO: 142) | CCCAAGCTTAGAACTCGG TAGGGTAGC (SEQ ID NO: 143) |
| pGEX 4T-1 | CT806B | 2868 | 479-739 | CCCACTAGTATGTGGGAGA ATGCAGATG (SEQ ID NO: 144) | CCCAAGCTTAGTCGATAA TAAATTG (SEQ ID NO: 145) |
| pGEX 4T-1 | CT806C | 2868 | 786-956 | CCCACTAGTATGTTGTTAT CTTGG (SEQ ID NO: 146) | CCCAAGCTTTTTTTCCTGA GACGAG (SEQ ID NO: 147) |
| pGEX 4T-1 | CT813 | 792 | 283-792 | Subcloned from pSDY8 | |
| pGEX 4T-1 | CT849 | 480 | FL | Subcloned from pSDY8 | |
| pGEX 4T-1 | CT852 | 615 | 30-204 | CTTACTAGTATGATGAAAA AATTTCTCTTTC (SEQ ID NO: 148) | CTTAAGCTTTTAAGGTGTA ACATA (SEQ ID NO: 149) |
| pGEX 4T-1 | CT853 | 600 | 67-199 | CTTACTAGTATGTCTTTGC AAACACCA (SEQ ID NO: 150) | CTTAAGCTTTTATAGGAA AGTTTG (SEQ ID NO: 151) |
| pGEX 4T-1 | CT863 | 1446 | FL | Subcloned from pSDY8 | |

Figure 4:
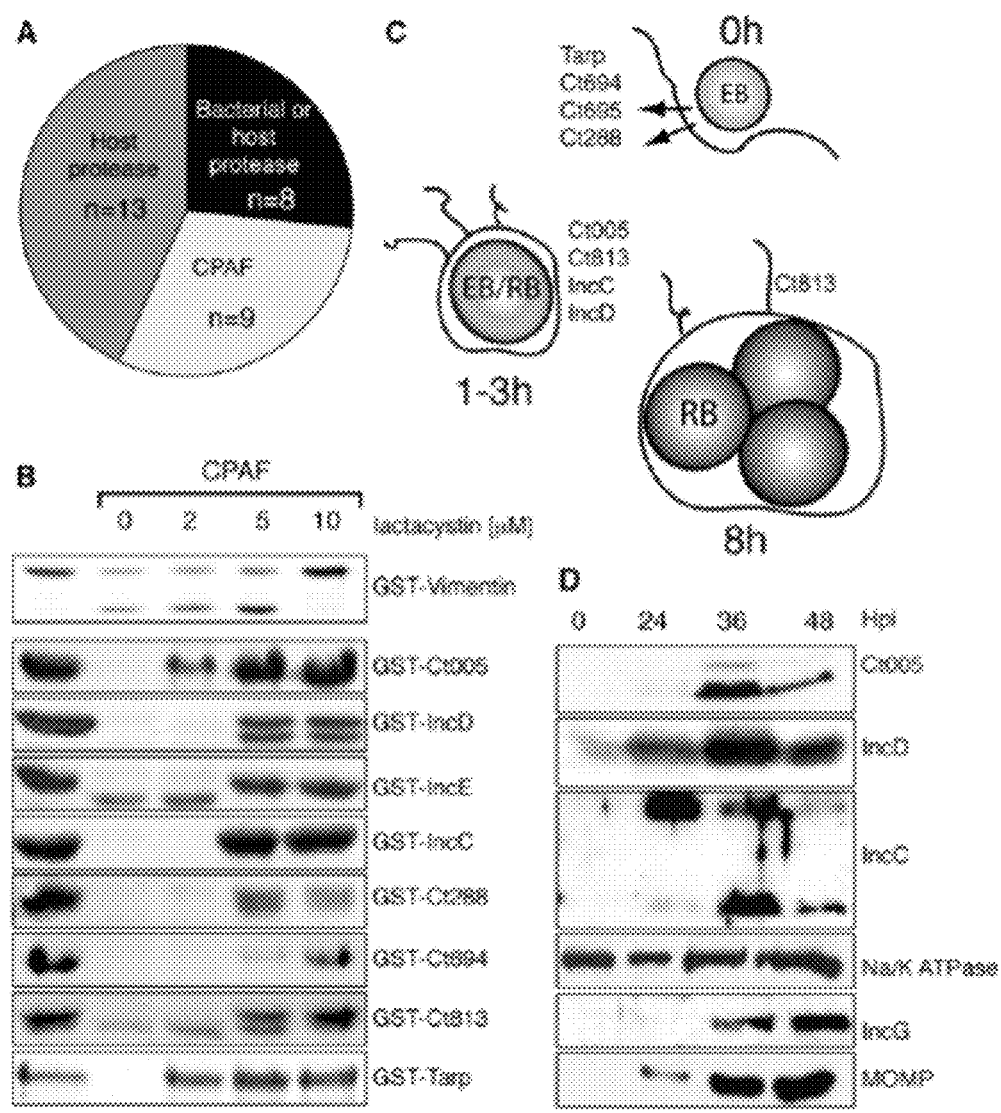
FIG. 4 depicts (A) Recombinant *Chlamydia* ORFs were tested for sensitivity to host and bacterial derived proteases. (B) Recombinant CPAF cleaves chlamydial substrates in a cell-free proteolysis assay. Purified his-tagged CPAF was incubated with GST-tagged chlamydial substrates at 37° C. for 20 min with increasing amounts of lactacystin. Cleavage products were run on an SDS PAGE gel and visualized with Coomassie blue staining. (C) Schematic summary of CPAF targets. CPAF specifically cleaves chlamydial effectors translocated during EB entry and early inclusion biogenesis. (D) The steady state levels of the inclusion membrane targets of CPAF decrease at late stages of infection. Membranes from *Chlamydia*-infected HeLa cells were harvested and purified at 0, 24, 36 and 48 hours post-infection, and the abundance of the chlamydial proteins Ct005, IncC and IncD were monitored with specific antibodies. Na/K ATPase and IncG served as host and bacterial-loading controls, respectively.

Recombinant CPAF was generated using pET30b (Huang et al., *Cell Host & Microbe*, 4:529-542 (2008). For in vitro cleavage assays, *Chlamydia* ORFs were expressed in either yeast or E. coli. Crude recombinant proteins were incubated for 30 minutes with cytosol from uninfected or LGV-L2 infected (40 h) HeLa cells, and processing was assessed by SDS-PAGE and immunoblotting using standard techniques. Approximately 8% of the expressed chlamydial proteins were sensitive to degradation after incubation with cytosol derived from infected cells (FIG. 3A). Processing ranged from the generation of distinct cleavage fragments to complete degradation (FIG. 3B). The protease-sensitive Chlamydial proteins comprised inclusion membrane proteins (n=9), outer membrane proteins (n=3), proteases (n=2), and ORFS of unknown function (n=9) (FIG. 3C and Table 2). Thirteen chlamydial proteins were also sensitive to proteolysis when treated with lysates from uninfected cells, indicating that these proteins are likely targets of host proteases (FIG. 3D, FIG. 4A, and Table 2).

TABLE 2

Summary of *Chlamydia* ORFs Sensitive to Host or Bacterial Proteolytic Activity

| ORF | Proteolytic activity | Predicted/confirmed function |
|---|---|---|
| CT005 | CPAF | Inclusion membrane protein |
| CT058 | bacterial | Inclusion membrane protein |
| CT082 | host | ORF of unknown function |
| CT105 | host | Inclusion membrane protein |
| CT113 | bacterial | ClpB-like ATP-dependent protease |
| CT115 | CPAF | Inclusion membrane protein |
| CT116 | CPAF | Inclusion membrane protein |
| CT134 | host | Inclusion membrane protein |
| CT142 | bacterial | ORF of unknown function |
| CT159 | host | ORF of unknown function |
| CT222 | host | Inclusion membrane protein |
| CT225 | host | Inclusion membrane protein |
| CT233 | CPAF | Inclusion membrane protein |
| CT242 | bacterial | Outer membrane protein |
| CT283 | bacterial | ORF of unknown function |
| CT288 | CPAF | Inclusion membrane protein/early effector |
| CT301 | bacterial | Serine/threonine kinase |
| CT371 | host | ORF of unknown function |

TABLE 2-continued

Summary of *Chlamydia* ORFs Sensitive to Host or Bacterial Proteolytic Activity

| ORF | Proteolytic activity | Predicted/confirmed function |
|---|---|---|
| CT384 | host | ORF of unknown function |
| CT423 | host | ORF of unknown function |
| CT456 | CPAF | Invasin, early effector |
| CT559 | host | Flagellar M-ring protein |
| CT568 | host | ORF of unknown function |
| CT632 | host | ORF of unknown function |
| CT694 | CPAF | Early effector, ORF of unknown function |
| CT695 | CPAF | Early effector, ORF of unknown function |
| CT813 | CPAF | Inclusion membrane protein/early effector |
| CT849 | bacterial | ORF of unknown function |
| CT852 | bacterial | Outer membrane protein |
| CT863 | host | ORF of unknown function |

Example 4

CPAF Cleaves a Subset of Chlamydial Effector Proteins

Nine Chlamydial proteins that were cleaved after incubation with cytosols derived from *Chlamydia*-infected cells were protected from degradation by pre-treatment with the proteasomal inhibitor lactacystin but not the unrelated proteasomal inhibitors MG132 and ALLN. To determine the role of CPAF in the cleavage of Chlamydial proteins, cytosols from infected HeLa cells were treated with anti-CPAF antisera.

Figure 5:
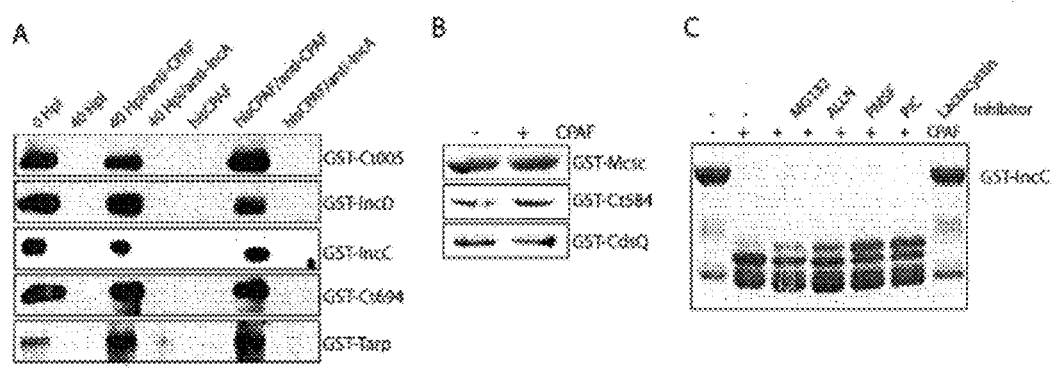
FIG. 5 depicts (A) that Polyclonal anti-CPAF antisera blocks proteolysis of chlamydial substrates. Cytosols from *Chlamydia*-infected HeLa cells (40 hrs) or recombinant his-tagged CPAF were pre-treated with rabbit polyclonal anti-CPAF or anti-IncA antisera, and incubated with GST-tagged *Chlamydia* proteins for 20 min at 37° C. (B) Recombinant CPAF does not cleave chlamydial proteins that are resistant to processing by cytosols form infected HeLa cells. Three example proteins shown include a type-III secretion (T3S) core component (CdsQ) a T3S chaperone (Mcsc) and a T3S needle component (Ct584). Processing of recombinant proteins in A-B were monitored by immunoblot analysis with specific antibodies. (C) Protease inhibitor profile of recombinant CPAF. Example shown for the chlamydial substrate GST-IncC. Degradation products were visualized by SDS-PAGE followed by staining with Coomassie blue. MG132, ALLN and lactacystin are all proteosome inhibitors. PMSF is a broad-spectrum serine protease inhibitor.

Lysates treated with polyclonal anti-CPAF antibodies, but not a control antibody, failed to cleave recombinant bacterial proteins (FIG. 5A). It was thus determined that nine of the proteolysis-sensitive Chlamydial proteins were likely CPAF substrates (FIG. 4A). Subsequent experiments tested whether CPAF was sufficient for this cleavage event. Recombinant CPAF readily cleaved vimentin, a known CPAF substrate, and recombinant Chlamydial proteins Ct005, IncD (Ct115), IncE (Ct116), IncC (Ct233), Ct288, Ct694, Ct695, Ct813 and Tarp (Ct456) (FIG. 4B). In contrast, GST-tagged proteins that were not identified as sensitive to proteolysis or those processed by host proteases were not cleaved by CPAF (FIG. 5B). As with endogenous CPAF, proteolysis by recombinant CPAF was inhibited by lactacystin but not by MG132, ALLN or a range of serine protease inhibitors (FIGS. 4B and 5C).

Figure 6:
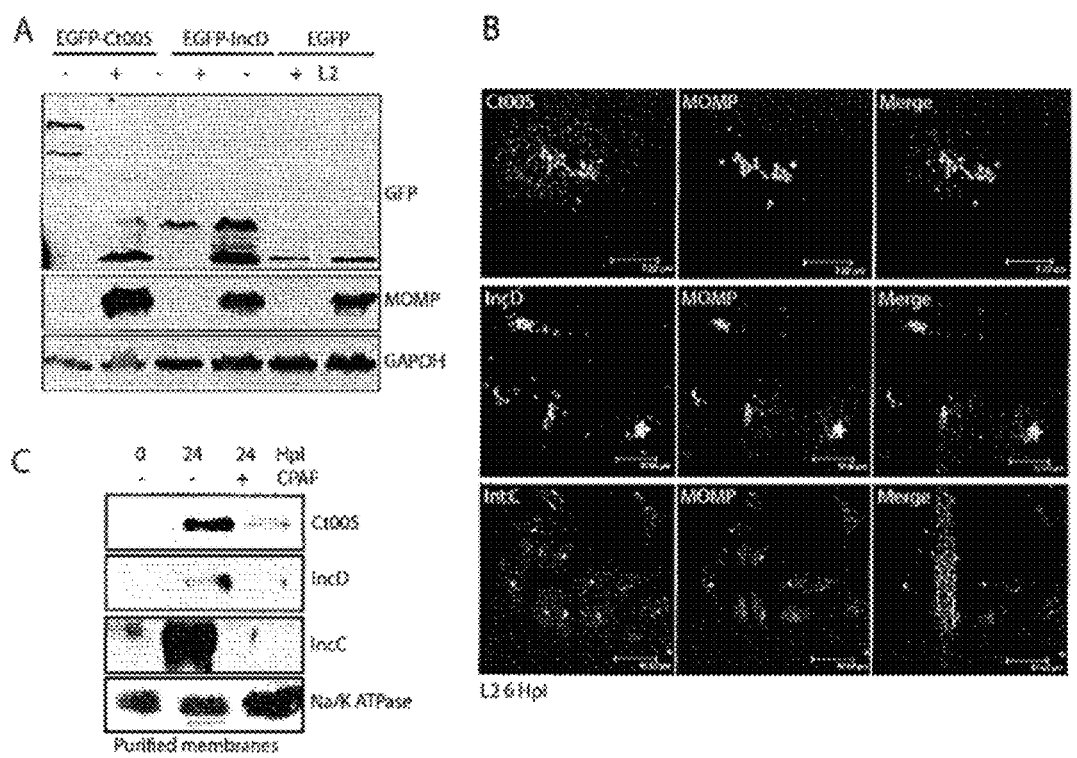
FIG. 6 depicts (A) HeLa cells transiently transfected with EGFP-tagged Ct005 and Ct115 mammalian expression constructs (Clontech) and infected with *C. trachomatis* (L2) for 36 hours or left uninfected. EGFP-tagged proteins were detected by immunoblot analysis of total protein lysates with anti-GFP monoclonal antibodies. Note accumulation of processed forms (*) in infected samples. MOMP and GAPDH levels were assessed to monitor chlamydial and host protein levels, respectively. (B) Recombinant CPAF cleaves Ct005, IncC and IncD from membranes isolated from infected cells. Density gradient purified membranes from L2 infected HeLa cell (24 hrs) were incubated with 6×His-tagged CPAF for 20 min at 37° C., and the levels of Inc proteins and a host membrane protein (Na/K ATPase) were assessed by immunoblot analysis with specific antibodies. (C) Ct005, IncC and IncD are expressed early in infection. HeLa cells were infected with L2 at MOI of 20, fixed at 6 hours, and analyzed by immunofluorescence microscopy with antisera specific for Ct005 (top panel), Ct115 (middle panel) and CT233 (bottom panel). Bacteria were stained with the outer membrane marker MOMP (red).

Additional experiments established that the Chlamydial CPAF substrates identified in vitro are cleaved during infection. First, EGFP-tagged CPAF substrates were expressed in infected cells and were processed, suggesting that GPAF can target these proteins in the cytoplasm of live cells (FIG. 6A). Next, antibodies were generated against three of these proteins (Ct005, IncC and IncD), and immunofluorescence microscopy (IF) confirmed that all were expressed by six hours post-infection (FIG. 6B). Changes in protein abundance were semi-quantitatively assessed by immunoblot analysis of membranes isolated from *Chlamydia*-infected HeLa cells. The levels of the major outer membrane protein MOMP, IncA and IncG, which are not CPAF substrates, increased throughout infection, reflecting the increased bacterial loads in these cells. CPAF is not expressed until the middle to late stages of infection (16-18 h post-infection), and, consistent with the predicted behavior of a CPAF substrate, the levels of Ct005, IncC and IncD increased from 24-36 h but dropped at 48 h (FIG. 4D). In addition, endogenous membrane-associated Ct005, IncC and IncD were also efficiently cleaved by recombinant CPAF in vitro (FIG. 6C).

Example 5

CPAF Cleaves Tarp During *Chlamydia* Entry into Pre-Infected Cells

Figure 7:
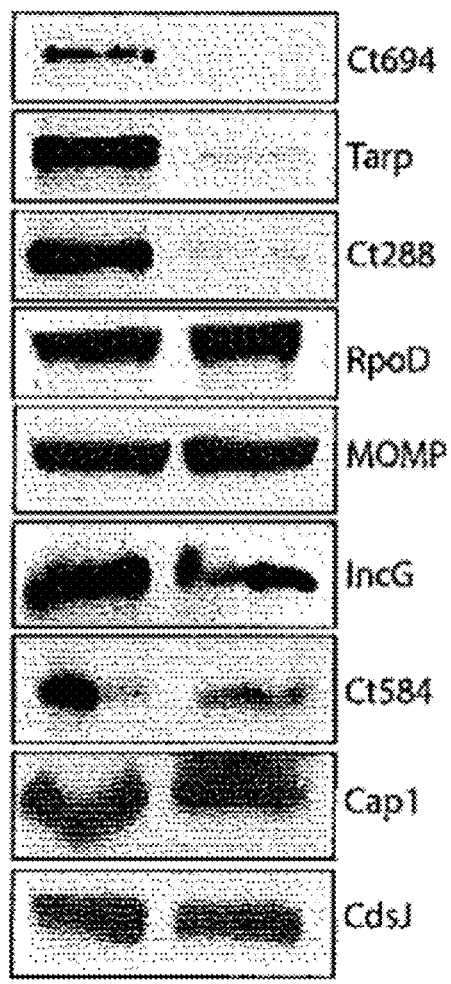
FIG. 7 depicts (A-B) Recombinant CPAF was incubated with EB lysates, resolved by SDS-PAGE and analyzed by immunoblotting with specific antibodies. Ct694, TARP and Ct288 were cleaved, but not other abundant EB proteins (A), and CPAF treatment did not lead to a broad degradation of EB proteins. Total proteins were detected by SDS-PAGE and Sypro-Orange staining.
Figure 7:
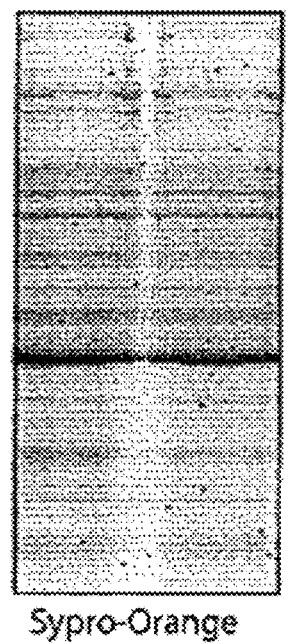

Tarp and Ct694, chlamydial proteins that get pre-packaged into EBs and translocated into the host cell during invasion, were identified as potential substrates of CPAF-mediated degradation (FIGS. 4B-4C). Initial experiments analyzed whether endogenous Tarp and Ct694 from EB lysates could be cleaved by CPAF. Recombinant CPAF specifically degraded endogenous Tarp and Ct694, but not housekeeping proteins, from EB lysates, and recombinant CPAF caused no non-specific degradation of EB proteins (FIG. 7).

One scenario where Tarp and Ct694 would encounter CPAF would be if an EB infected a cell that already contains a mature inclusion. The levels of Tarp at EB entry sites were compared upon attachment to uninfected or pre-infected HeLa cells. Tarp is phosphorylated at multiple tyrosine residues by host tyrosine kinases, and immunofluorescent staining with anti-phosphotyrosine antibodies revealed a prominent cup of immunoreactive material at EB attachments sites. Consistent with this data, multiple phosphotyrosine-positive foci were observed immediately adjacent to EBs attached to the plasma membrane of HeLa cells. These foci, however, were largely absent at EB attachment sites in HeLa cells that were pre-infected with *Chlamydia* for 30 hours (FIGS. 8A-8B), indicating that either Tarp translocation or phosphorylation is inhibited, or that translocated Tarp is degraded.

Figure 8:
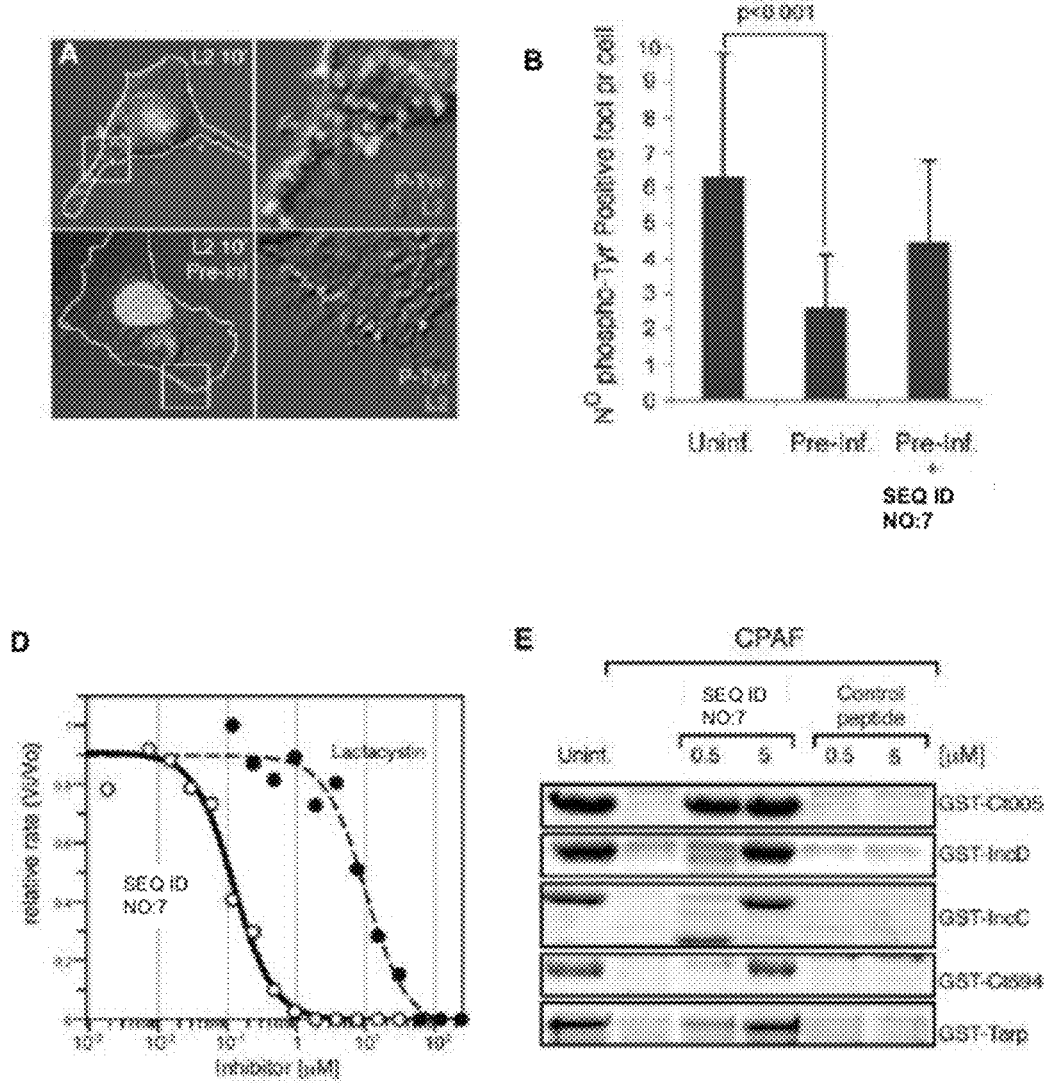
FIG. 8 depicts (A-C(I-IV)) Tarp translocated by EBs is a target of CPAF-mediated degradation. Uninfected and HeLa cells pre-infected with L2 for 30 hrs were treated with inhibitory peptides and infected with EBs for 10 min Tarp translocation was indirectly visualized with an anti-phosphotyrosine antibody (A) and quantified by counting 50 separate cells (B). The stability of newly translocated Tarp was assessed by infecting cells as in (A) but with $S^{35}$-labeled EBs, followed by sequential immunoprecipitation of Tarp and MOMP and Phosphoimager analysis of precipitated material (C (I-IV)). Tarp is degraded in pre-infected HeLa cells in a CPAF-dependent manner. (D) Effective inhibition of CPAF activity by inhibitory peptide. $IC_{50}$ values were determined by assessing CPAF cleavage of an Abz-tagged CPAF substrate (SEQ ID NO:9) by HPLC. Assays were performed the presence of increasing amount of inhibitors. (E-F) SEQ ID NO:7 peptide, but not a scrambled sequence of equal molecular weight (SEQ ID NO:11), broadly inhibited degradation of CPAF substrates in vitro and in vivo. CPAF cleavage of GST-chlamydial substrates was performed as in FIG. 4B but in the presence of SEQ ID NO:7 and SEQ ID NO:11 peptides (E). For in vivo inhibition effects on Chlamydia (L2), infected HeLa cells were treated with peptides at 12 hpi, and harvested at 30 hpi (F). Vimentin and Puma cleavage was inhibited in infected cells treated with SEQ ID NO:7 peptide. (G and H) CPAF restricts EB entry into preinfected cells. Cells were infected as in (A), except that the secondary infections (30 min) were performed with fluorescently labeled EBs and infected cells were not permeabilized. Extracellular EBs were distinguished from intracellular EBs based on their immunoreactivity to anti-L2 antibodies. Extracellular bacteria were determined. There was clustering of internalized bacteria at a perinuclear site. The number of internalized EBs was quantified per cell (H). Representative of two experiments performed in duplicate (n=40 cells). Error bars represent±standard error.
Figure 8C:
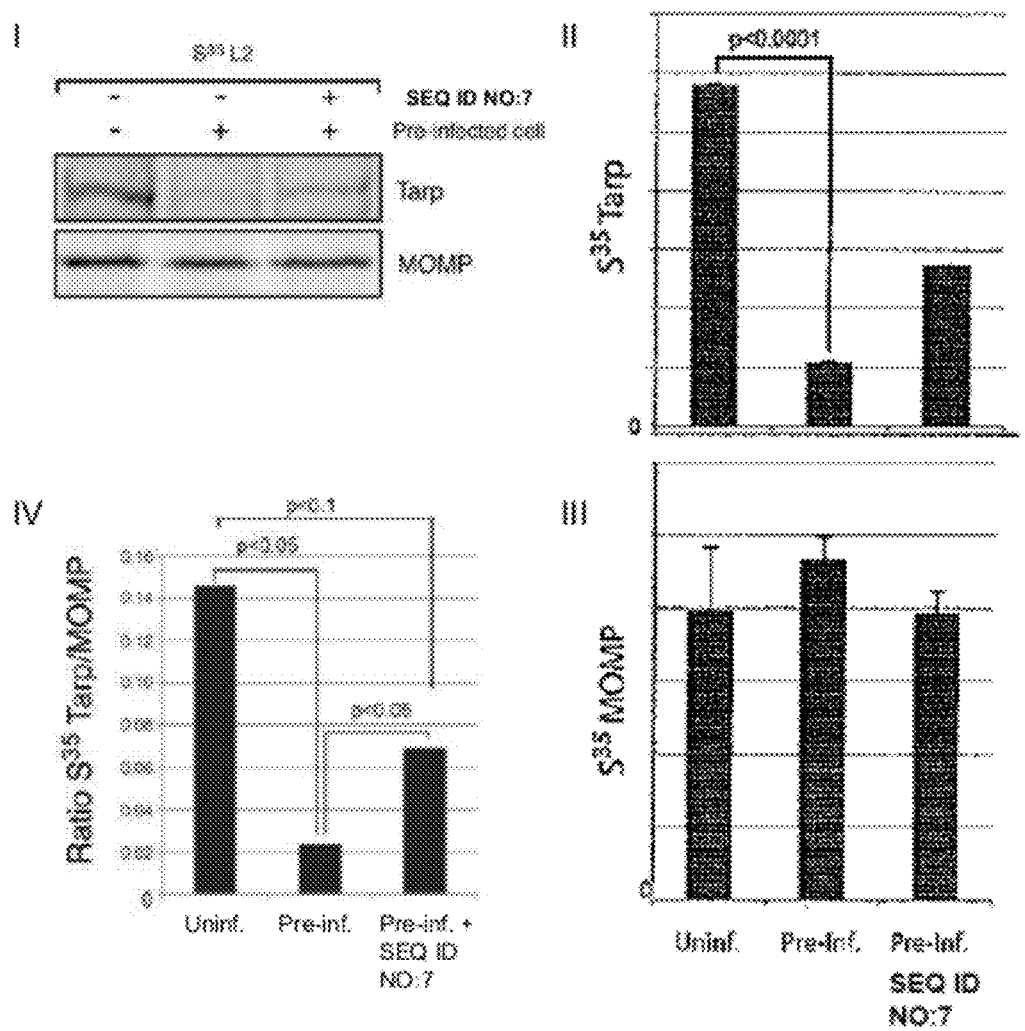
Figure 8:
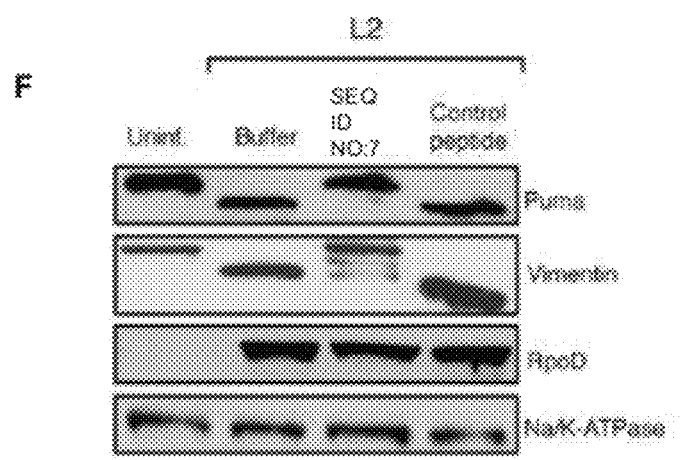
Figure 8:
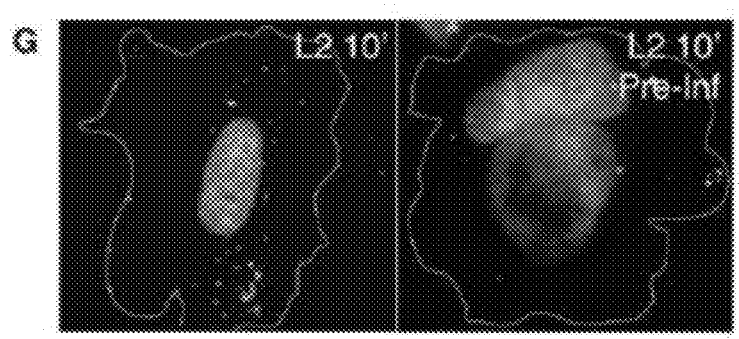
Figure 8:
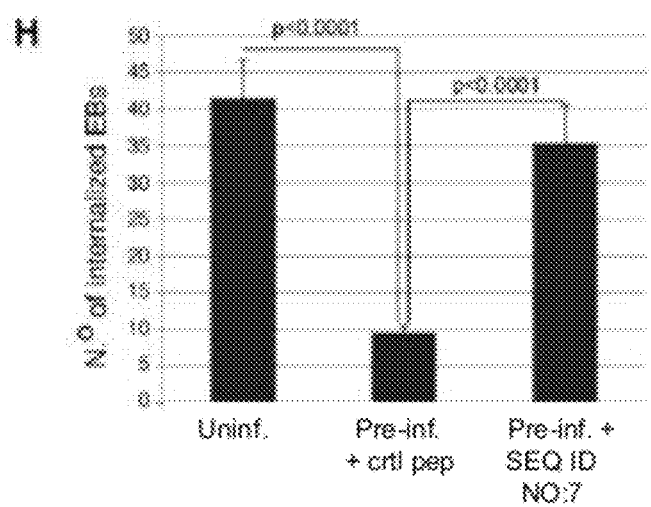

Next, HeLa cells or inclusion-containing HeLa cells were infected with $^{35}$S-radiolabeled EBs, followed by immunoprecipitation of Tarp at various times after infection to determine the stability of translocated Tarp under these conditions. HeLa cells were infected with *C. trachomatis* for 18 hours and labeled with 300 µCi $^{35}$S-labeled cysteine/methionine (available from Perkin Elmer) in the presence of 40 µg/ml cyclohexamide (available from Sigma) for 22 hours. Radiolabeled EB seed were harvested following gentle sonication and stored at −80° C. in SPG bugger (0.25 M sucrose, 10 mM sodium phosphate, 5 mM L-glutamic acid). Uninfected HeLa cells or HeLa cells infected for 30 hours with cold LGV-L2 at an MOI of 1 were then infected with cold or 35S-labeled EBs at an MOI of 50. Cells were washed extensively with trypsin, and harvested with lysis buffer (20 mM Tris, 150 mM NaCl, 1% Tx100, 2 mM PMSF, 2 mM MG132, 10 mM ALLN, protease inhibitor cocktail (Roche)), or fixed, at 10 minutes or 30 minutes after secondary infection. Tarp and MOMP were immunoprecipitated using anti-Tarp and anti-MOMP protein A sepharose beads (available from GE Healthcare), detected in a Typhoon9410 Variable Image Phosphor Imager (available from Amersham Biosciences), and quantified using ImageQuant 5.1TL software (available from GE Healthcare). To test the effect of inhibitory peptide, cells were treated with 12 µM peptides for the duration of the secondary infections. To distinguish intracellular from extracellular EBs, cells were infected with CellTracker (Invitrogen)-labeled EBs for 30 min, fixed without permeabilization and extracellular EBs were immunostained with an anti-LGV-L2 antisera. Radiolabeled Tarp, but not the outer membrane protein MOMP, was efficiently degraded in HeLa cells harboring mature inclusions but not in uninfected HeLa cells (FIG. 8C).

Example 6

A Cell-Permeable Inhibitor of CPAF Prevents Cleavage of CPAF Substrates in Chlamydia-Infected Cells A peptide of SEQ ID NO:7, but not a scrambled control peptide (SEQ ID NO:11), inhibited cleavage of the host substrates CPAF vimentin and puma in vivo when applied to Chlamydia-infected cells (FIG. 8F), indicating that mammalian cells efficiently internalize the peptide and that CPAF activity can be inhibited within live infected cells. A peptide of SEQ ID NO:7 also restored the accumulation of Tyr-phosphorylated proteins at EB attachments sites on pre-infected cells (FIG. 8B) and blocked the degradation of Tarp in pulse-chase experiments (FIG. 8C).

CPAF-mediated degradation of effectors secreted by EBs during invasion may protect preinfected cells against superinfection. To test whether infected cells are refractory to reinfection, we quantified the number of EBs internalized by uninfected cells and preinfected cells. We observed a significant decrease in the number of newly internalized EBs in cells that contains a mature inclusion compared to uninfected cells (FIG. 8G). This resistance to reinfection is partially mediated by CPAF, as treatment of preinfected cells with anti-CPAF peptides increased EB entry (FIG. 8H).

Figure 9:
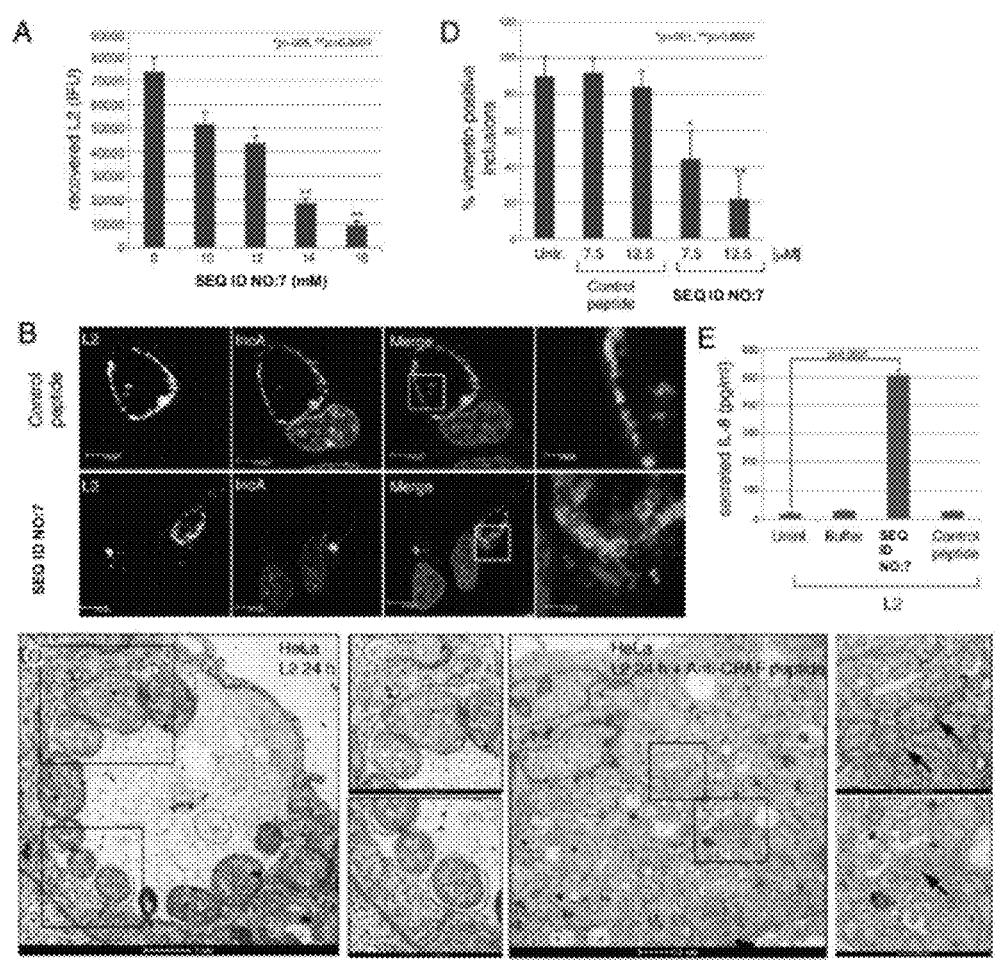
FIG. 9 depicts (A) CPAF inhibitory peptides block the generation of Chlamydia infectious particles. L2-infected HeLa cells were treated at 12 hpi with increasing concentration of peptides. EBs were harvested at 30 hpi and inclusion-forming units (IFU) were quantified on fresh cell monolayers. (B-D) CPAF activity is required to maintain inclusion integrity. The integrity of the inclusion was determined by assessing the immunolocalization of the inclusion membrane marker IncA (red) and Chlamydia (green) (B) and by transmission electron microscopy (C). Collapse of IncA-positive membranes and loss of inclusion integrity was observed with bacteria in the cytoplasm (arrows) of infected cells lacking CPAF activity (right panels). (D) The percentage of vimentin-positive inclusions was determined by IF in infected cells treated with SEQ ID NO:7 and SEQ ID NO:11 (12 hpi) peptides at 24 hpi. (E) Activation of inflammatory cytokines upon inhibition of CPAF activity. Levels of IL-8 supernatants from Chlamydia infected cells treated with peptides as in (B-D) were determined at 24 hpi by ELISA.
Figure 10:
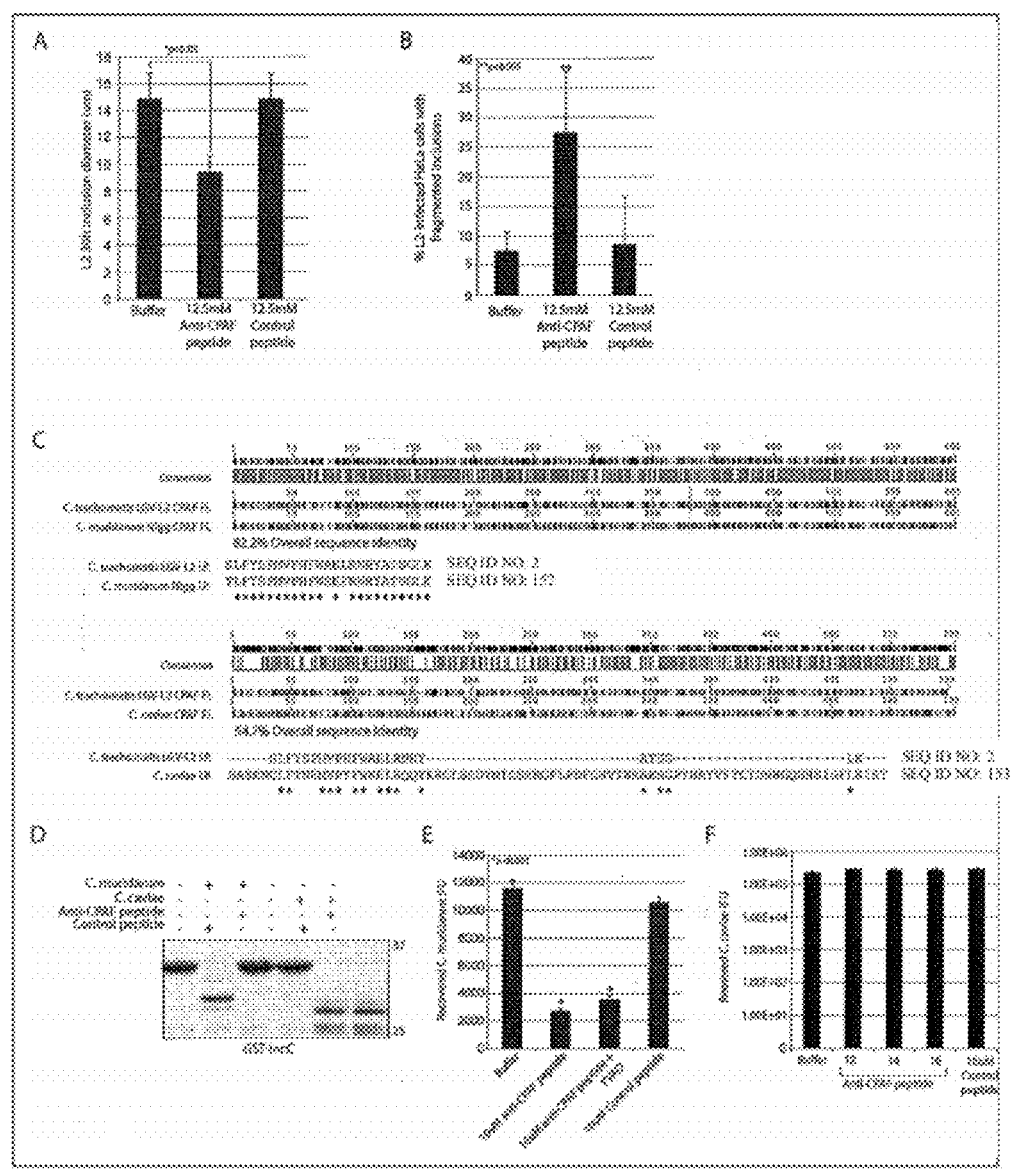
FIG. 10 depicts (A-B) HeLa cells infected with C. trachomatis and treated with CPAF inhibitors exhibited decreased inclusion diameter (A) and increased frequency of fragmented inclusions (B). Cells were infected with an MOI of 1 and treated with CPAF inhibitor (SEQ ID NO:7) or control (SEQ ID NO:11) peptides at 12 hpi, fixed at 24 hpi and analyzed by IF with anti-L2 polyclonal antisera. Inclusion size was determined by measuring the inclusion diameter in µm by confocal microscopy of 50 infected cells. The number of cells with fragmented inclusions was determined by counting the number of infected cells out of 50 with more than one inclusion. (C) Sequence alignment and % sequence identify of full length CPAF and predicted inhibitory peptide sequence between C. trachomatis serovar LGV-L2, Chlamydia muridarum, and Chlamydophila caviae was determined using Geneious software (available at the Geneious website). (D) SEQ ID NO:7 inhibits C. muridarum CPAF, but not C. ceviae CPAF. GPIC or C. muridarum infected whole cell protein lysate was preincubated with SEQ ID NO:7 peptide or SEQ ID NO:11 control peptide, mixed with GST-IncC at 37° C., resolved by SDS-PAGE and stained with Coomassie blue. (E-F) Treatment with SEQ ID NO:7 impairs growth in C. muridarum, but not in C. caviae. Inhibition of C. muridarum (E) and C. ceviae (F) growth was determined by counting the number of recovered IFUs. The Caspase-1 inhibitor Ac-YVAD-CMK at 2 hpi does not rescue the growth defect of C. muridarum in infected cells treated with SEQ ID NO:7 (E). Inclusions were detected by IF with anti-LGV-L2 (A, B, E) antisera or anti-chlamydial LPS (F) monoclonal antibodies, and host nuclei sere detected by staining.

Next, Chlamydia-infected cells were treated with peptide (SEQ ID NO:7 or SEQ ID NO:11), and treatment with SEQ ID NO:7 significantly lowered yields of EBs and stunted inclusion growth (FIGS. 9A, 10A, 10B). Next, the mechanism underlying the block in chlamydial replication was assessed by performing microscopy analyses of Chlamydia-infected cells treated with an inhibitor of CPAF (SEQ ID NO:7). Prolonged treatment with (>8 h) with SEQ ID NO:7, but not SEQ ID NO:11, led to the collapse of the inclusion structure with the inclusion membrane markers IncA and Cap1 localizing to aggregates (FIG. 9B). Ultra-structural analysis of these cells by transmission electron microscopy confirmed the loss of inclusion integrity, disruption of the inclusion membrane with intact Chlamydia cells residing in the cytoplasm (FIG. 9C). Accordingly, the treated cells exhibited a loss of vimentin re-organization around the inclusion (FIG. 9D), indicating a loss inclusion stability. Consistent with the increased load of microbial products in the cytoplasm, treated cells also exhibited increased IL-8 secretion (FIG. 9E). HeLa cells were infected with C. trachomatis LGV-L2 at an MOI of 1. At 3 hours post-infection, cells were treated with 40 µM Z-VAD-FMK (available from Promega) or 400 µM Ac-YVAD-CMK (available from Enzo Life Sciences). At 12 hours post-infection, cells were treated with peptides at 12.5 µM (either SEQ ID NO:7 or SEQ ID NO:11). IL-8 secretion into the media was determined with a Human IL-8 ELISA kit (available from BioLegend).

These observations indicated that SEQ ID NO:7 is an inhibitor of CPAF that can efficiently inhibit CPAF activity in vivo.

The specificity of SEQ ID NO:7 was evaluated by testing its effect on HeLa cells infected with C. muridarum and C. caviae, two Chlamydiae species that display varying degrees of CPAF conservation with C. trachomatis (FIG. 10C). Consistent with the higher conservation between C. trachomatis and C. muridarum CPAFs, SEQ ID NO:7 prevented cleavage of substrate by C. muridarum CPAF (FIG. 10D) and blocked C. muridarum replication (FIG. 10E). In contrast, C. caviae and C. trachomatis CPAF are much more divergent, and C. caviae CPAF was not sensitive to inhibition by SEQ ID NO:7 (FIGS. 10D, 10F).

Figure 19:
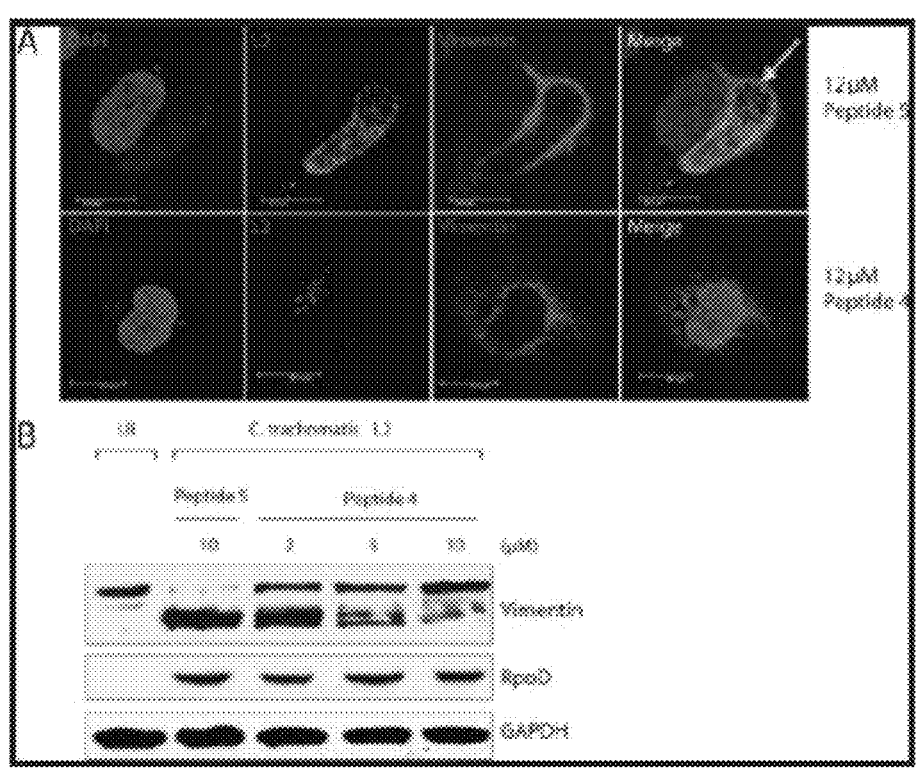
FIG. 19 depicts HeLa cells infected with C. trachomatis L2, treated with SEQ ID NO:11 and SEQ ID NO:7, and harvested at 30 hpi. (A) Immunofluorescence microscopy via staining with an anti-vimentin antibody ("vimentin") and an anti-Chlamydia L2 antibody ("L2"). Note the loss of the vimentin cage (arrow) surrounding the inclusion in cells treated with peptide 4. (B) Cells were lysed in the presence of protease inhibitors, resolved by SDS-PAGE, and subjected to immunoblot analysis. Vimentin, RpoD (bacterial loading control), and GAPDH (host loading control) were visualized with substrate-specific antibodies).

Treating C. trachomatis LGV-L2 434-infected HeLa cells with lactacystin resulted in fiber oligomerization of vimentin due to inhibition of CPAF-mediated proteolysis (Kumar et al., (2008) Cell Host Microbe 4, 159-169). To establish if CPAF was inhibited by SEQ ID NO:7 during infection, vimentin cleavage was assessed in C. trachomatis LGV-L2 434-infected HeLa cells after treatment with a range of concentrations (2-10 µM). Under similar conditions, infected HeLa cells were treated with a sequence-scrambled control peptide that possessed no CPAF inhibitory activity in vitro [H-NFALSHFRLPLSTYKEMPYVSHWAGR-RRRRRRRR-NH$_2$ (SEQ ID NO:11)]. SEQ ID NO:7, but not the SEQ ID NO:11, markedly inhibited CPAF-mediated degradation of vimentin in a dose dependent manner (FIG. 19B). This result strongly suggested that SEQ ID NO:7 not only penetrated the cell membrane but also selectively targeted CPAF activity ex vivo. The permeability of these peptides is most likely modest with respect to the percentage of peptide being delivered; however, the ability to inhibit still renders them useful.

Chlamydia remodels and recruits cytoskeletal components of the host cell such as F-actin and vimentin to form a dynamic scaffold or "cage" that provides structural stability to the inclusion. As the inclusion expands, secreted CPAF progressively modifies the intermediate filament scaffold, presumably to increase the inclusion's flexibility and accommodate the increased bacterial load. In infected cells, CPAF processing of vimentin filaments occurs several hours after the hour postinfection (hpi) at which CPAF can be detected in the cytosol. Treatment of C. trachomatis-infected HeLa cells with SEQ ID NO:7, but not SEQ ID NO:11, resulted in a loss of vimentin processing (FIG. 19B) and increased disorder in the position of the vimentin cage surrounding the inclusion (FIG. 19A). These data suggest that SEQ ID NO:7 selectively inhibits CPAF activity, which prevents vimentin cleavage and proper deposition of vimentin surrounding the intracellular vacuole (FIG. 19A). Because intermediate filaments like vimentin are stable structures that provide mechanical support to maintain vacuole integrity in infected cells, it is likely that SEQ ID NO:7 altered the integrity of the vacuole, which may have a broader impact on bacterial survival within the host.

Example 7

Figure 11:
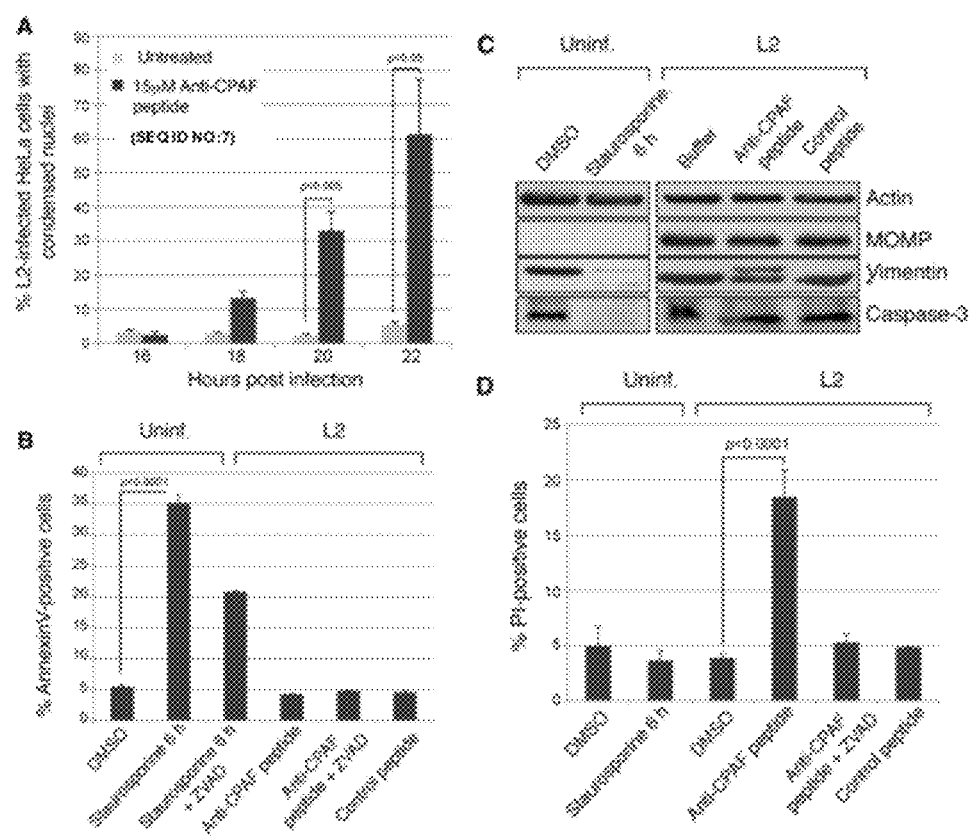
FIG. 11 depicts (A) that inhibiting CPAF activity induces host cell death. The indicated peptides (anti-CPAF peptide refers to SEQ ID NO:7) were added to infected cells 12 hpi and the percentage of infected cells with condensed nuclei was quantified at the indicated times. (B-C) Inhibition of CPAF activity induces apoptosis. Infected cells were treated with peptides and the percentage of AnnexinV-FITC positive (propidium iodide (PI) negative) was determined by flow cytometry (B). In parallel samples, cleavage of Caspase-3, a hallmark of apoptosome activation, was monitored by immunoblot analysis. Actin and MOMP are host and bacterial loading controls respectively. Staurosporine (2 µM)-treatment was used as a positive control and the pan-caspase inhibitor ZVAD-FMK were used as controls. (D) Cell death is blocked by a pan-Caspase inhibitor. Infected cells were treated as in (A) in the presence or absence of ZVAD-FMK, labeled with PI and analyzed by flow cytometry. Cells pre-treated with ZVAD-FMK and the control peptide lacked PI staining.
Figure 12:
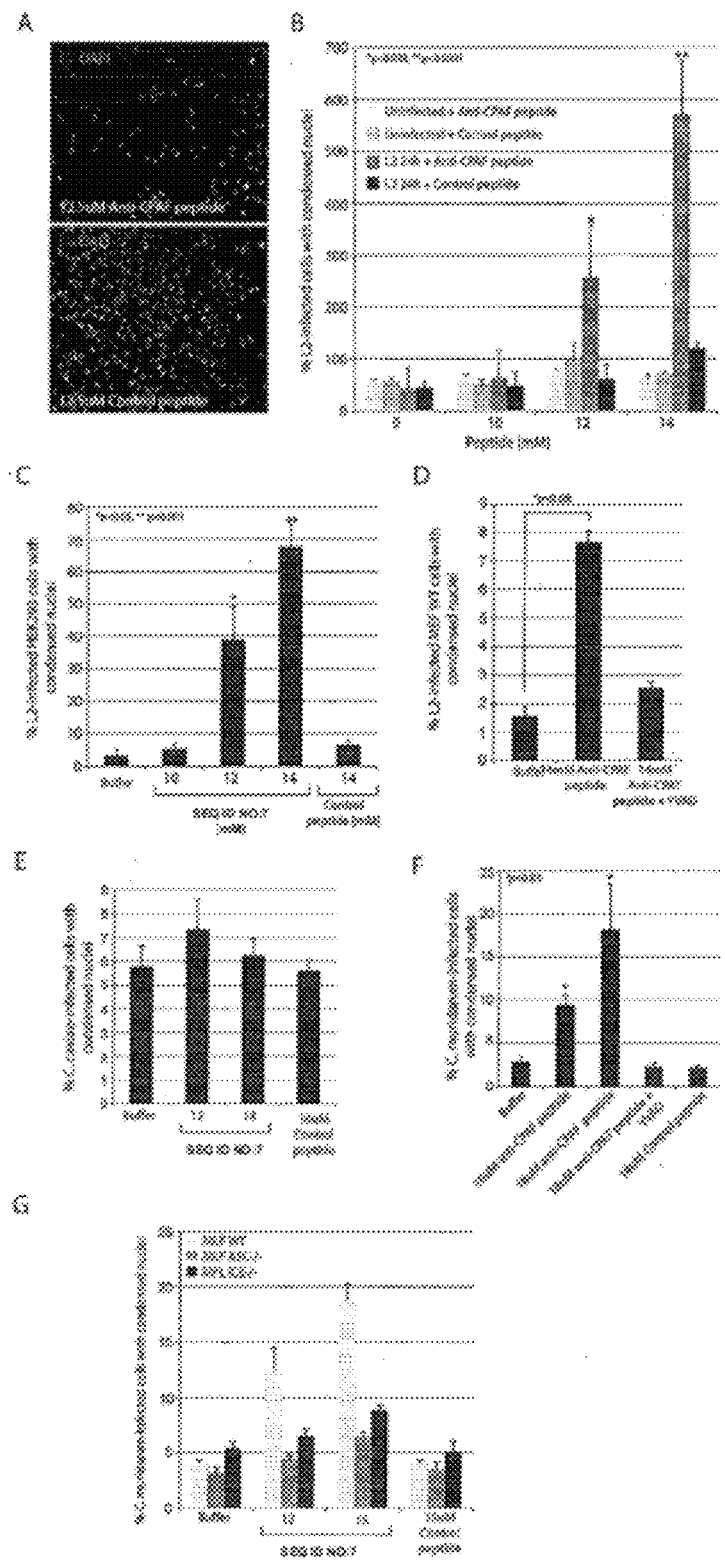
FIG. 12 depicts (A) low-magnification view of C. trachomatis LGV-L2 infected HeLa monolayers (30 h) treated with SEQ ID NO:7 or SEQ ID NO:11 peptides. (B) The frequency of condensed nuclei in treated cells is dependent on peptide concentration and Chlamydia infection. (C-D) Toxicity of CPAF inhibitors to Chlamydia-infected cells is observed in non-myeloid cells including human embryonic kidney cells HEK293 (C) and mouse embryo fibroblasts (D). (E) EQ ID NO:7 peptides do not cause cell death in C. ceviae infected HeLa cells. (F-G) Cell death induced by anti-CPAF peptides requires Caspase-1 activation. HeLa cells infected with C. muridarum were treated with Ac-YVAD-CMK at 2 hpi, SEQ ID NO:7 peptide or SEQ ID NO:11 control peptide at 12 hpi and the percentage of infected cells with condensed nuclei was assessed at 48 hpi (F). Mouse lung fibroblasts (MLF) derived from congenic WT, ICE1$^{-/-}$ and ASC$^{-/-}$ animals were infected with C. muridarum and treated with the indicated concentrations of anti peptides 12 hpi. The percentage of infected cells with condensed nuclei was assessed at 48 hpi (G). LGV-L2 inclusions were immunostained with anti-L2 antisera and C. muridarum and C. caviae inclusions were immunostained with an anti-chlamydial LPS monoclonal antibody. Cell death in infected and uninfected cells treated with CPAF inhibitory peptides or control peptides was determined by counting the number of condensed nuclei of ~1000 cells.

In Vivo Inhibition of CPAF Induces Caspase-1 Dependent Death of Infected Cells In general, Chlamydia-infected cells are highly resistant to intrinsic and extrinsic apoptotic stimuli. Nonetheless, in a dose-dependent manner, treatment with SEQ ID NO:7, but not control peptide SEQ ID NO:11, led to a marked increase in the number of condensed nuclei in epithelial cells infected with C. trachomatis and C. muridarum, but not C. caviae (FIGS. 11A, 12A, 12B). The onset of death in infected cells at approximately 20 hours post-infection coincided with translocation of CPAF into the host cytoplasm (FIG. 11A) and was observed in several non-myeloid cell lines (FIGS. 10A, 10B).

Subsequent experiments tested whether CPAF inhibition led to the onset of apoptosis in infected cells. HeLa cells were infected with C. trachomatis LGV-L2 at an MOI of 1. At 3 hours post-infection, cells were treated with 40 µM Z-VAD-FMK (available from Promega) or 400 µM Ac-YVAD-CMK (available from Enzo Life Sciences). At 12 hours post-infection, cells were treated with peptides at 12.5 µM (either SEQ ID NO:7 or SEQ ID NO:11). Apoptotic cells were identified with an AnnexinV-FLOUS Staining Kit (available from Roche) and activation of Caspase-1 was determined by labeling active Caspase-1 with a Carboxyfluorescein FLICA Detection Kit (available from Immunochemistry) and analyzed in a FACScanner (available from BD Biosciences). *Chlamydia*-infected cells were labeled with propidium iodide and an AnnexinV staining kit to monitor the loss of plasma membrane asymmetry in intact cells a hallmark of apoptosis. *Chlamydia*-infected cells treated with SEQ ID NO:7 peptide did not stain for AnnexinV, indicating that the observed cell death is unlikely the result of classical apoptosis (FIG. 11B). Consistent with result, Caspase-3 cleavage, another characteristic of apoptotic cell death, was not detected (FIG. 11C).

Figure 13:
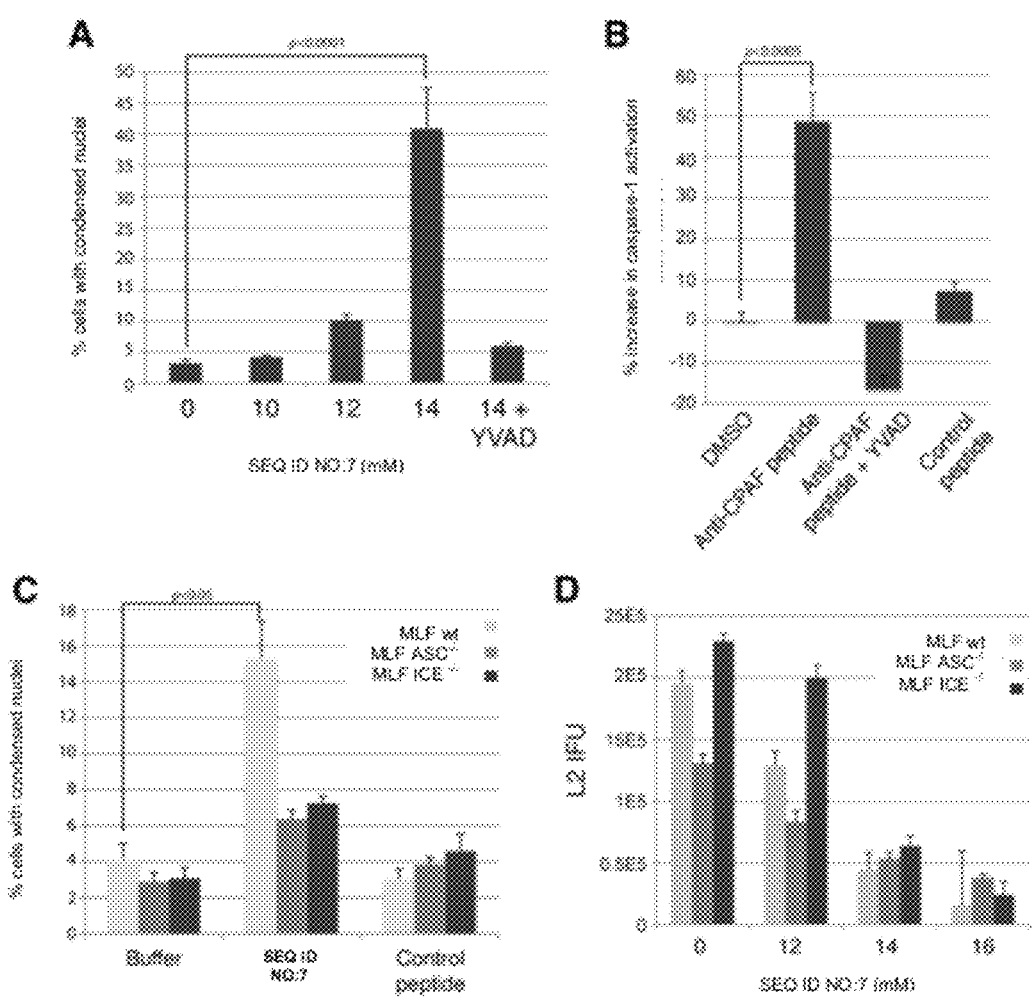
FIG. 13 depicts (A) that Caspase-1 inhibitors block Chlamydia-mediated cell death. Infected cells were treated with the Caspase-1 inhibitor Ac-YVAD-CMK at 2 hpi, and increasing concentrations of CPAF inhibitor added at 12 hpi. Cells were fixed and the percentage of cells with condensed nuclei determined at 24 hpi. (B) Enhanced Caspase-1 activation in infected cells lacking CPAF activity. Infected cells were labeled with a cell-permeable fluorescent substrate of Caspase-1 and treated with inhibitory peptides, and Caspase-1 activity was monitored by flow cytometry. (C) Caspase-1 and ASC are required for Chlamydia-mediated host cell death. Chlamydia-infected lung fibroblast derived from Caspase-1 (ICE$^{-/-}$) and ASC adaptor (ASC$^{-/-}$) knockout mice were resistant to cell-death induced by CPAF inhibitor peptides. (D) CPAF is required for chlamydial replication independently of its role in suppressing Caspase-1 mediated cell death. Chlamydia replication and generation of IFUs in MLFs was assessed as in FIG. 9. Note dose-dependent loss in IFU yields in all MLF lines.

The pan-caspase inhibitor ZVAD-FMK efficiently blocked the death of *Chlamydia*-infected cells treated SEQ ID NO:7 (FIG. 11D). In myeloid cells, activation of Caspase-1 by infectious agents can lead to pyroptosis, a cell death pathway accompanied by pore-formation and the release of pro-inflammatory cytokines. The caspase-1 inhibitor Ac-YVAD-CMK efficiently blocked the death of *Chlamydia*-infected cells treated with SEQ ID NO:7 (FIG. 13A). In addition, caspase-1 activity, as assessed with a fluorescently labeled caspase-1 substrate (Darzynkiewicz et al., *Methods Mol. Biol.*, 682:103-114 (2011)), was significantly increased during treatment with SEQ ID NO:7 (FIG. 13B). Further experiments confirmed the role played by caspase-1 and its upstream activator, the inflammasome adaptor proteins ASC in mediating cell death by infecting mouse lung fibroblasts derived from caspase-1 (ICE$^{-/-}$) and ASC (ASC$^{-/-}$) knockout mice with *C. trachomatis* and *C. muridarum*. These cells, unlike their wild-type counterparts, were resistant to host cell death in response to treatment SEQ ID NO:7, indicating that inflammasome-dependent activation of caspase-1 is required for host-induced cell death (FIGS. 13C, 12H). Pharmacological or genetic inhibition of caspase-1 did not rescue bacterial replication, (FIGS. 13D, 10F). These findings indicate that CPAF suppresses caspase-1 dependent cell death during Chlamydial infection.

Example 8

CPAF Enzyme Kinetics

Proteolytic enzyme kinetics of CPAF were measured using an HPLC-based assay that quantifies the cleavage of an Abz-tagged model CPAF substrate derived from human vimentin:

```
(SEQ ID NO: 9; scissile S-S bond underlined)
Abz-V-R-L-R-S-S-V-P-G-V-NH2
```

Figure 14:
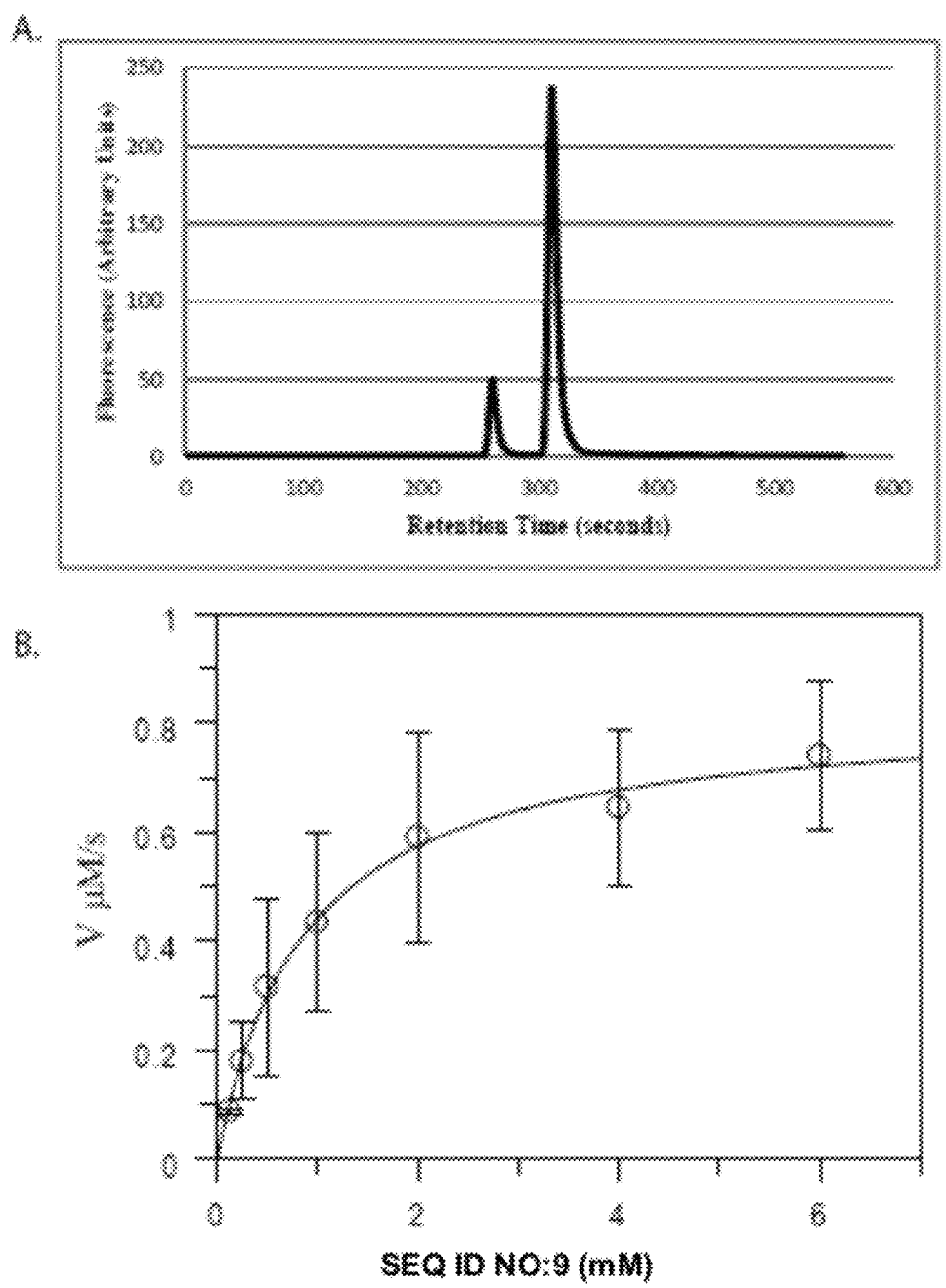
FIG. 14 depicts an embodiment of the HPLC-based methods for assessing CPAF activity, CPAF inhibitors, and candidate compounds. (A) Representative HPLC trace showing the model CPAF substrate SEQ ID NO:9 (Abz-VRLRSSVPGV) and the Abz-containing product resulting from cleavage of the model CPAF substrate by CPAF (Abz-VRLRS). The chromatograph corresponds to fluorescence emission at 420 nm of a 20 µL aliquot of a quenched assay. Initial velocities (Vi) were calculated from the linear portion of each assay, and peak area was converted to concentration using standard methods. (B) Determination of kinetic parameters for CPAF using the model CPAF substrate SEQ ID NO:9 in an HPLC-based assay. Assays were performed in a total volume of 100 µL containing assay buffer, CPAF (62.5 nM), and varying concentrations of CPAF substrate (SEQ ID NO:9) (0-6 mM). Kinetic parameters of KM=0.88 mM and kcat=13.2 $s^{-1}$ were obtained.

Standard assays were performed in a total volume of 100 µL containing Assay Buffer (150 mM NaCl, 50 mM Tris pH 7.5), CPAF (62.5 nM), and varying concentrations (0-6 mM) of CPAF substrate (SEQ ID NO:9). Reactions were initiated by the addition of enzyme and incubated at 25° C. for 90 seconds. Incubation was followed by removal of 80 µL aliquots and quenched by the addition of 40 µL 1.2 M HCl. The reaction mixtures were injected directly onto a Vydac reversed-phase C18 fast analytical HPLC column (available from Grace Davison Discovery Sciences) and the peptides were separated using a linear gradient from 100% H20/TFA (100/0.1, v/v) to 75%, MeOH/TFA (90/0.1, v/v) over 6 min Abz is a fluorescent molecule that is excited at 318 nm and emits at 420 nm, allowing detection of Abz-tagged peptides or peptide fragments. Abz-containing peptides were detected by fluorescence emission at 420 nm, and the composition and identity of each product were confirmed by mass spectrometry by LCMS. HPLC was performed using an Agilent 1200 series apparatus. FIG. 14A shows a representative HPLC trace with peaks for uncleaved model substrate (SEQ ID NO:9) and the Abz-containing cleavage product resulting form CPAF cleavage (Abz-VRLRS-OH). The percentage of substrate converted to product was calculated from the HPLC data by integrating the area under the peaks in the chromatograms using PeakFit v4.11 (available from Systat Software), followed by analysis in Grafit 6.0 (available from Erithacus Software) using the following equation:

$$v = \frac{V_{max} \times [S]}{K_M + [S]}$$

The following kinetic parameters were determined for CPAF proteolysis: (1) $k_{cat}$=13.2 5$^{-1}$; (2) $K_M$=0.88 mM; and (3) $k_{cat}/K_M$=1.5×10$^4$ M$^{-1}$s$^{-1}$ (see FIG. 14B).

Example 9

Assays for Measuring Inhibition of CPAF Activity and/or Identifying an Inhibitor of CPAF The efficiency of candidate compounds as CPAF inhibitors was tested in vitro using HPLC- and FRET-based assays that measure the cleavage of model CPAF substrates comprising SEQ ID NO:8 and derived from human vimentin.

HPLC-based assays comprised an Abz-tagged model CPAF substrate (SEQ ID NO:9) and were performed in a final volume of 100 µL containing 150 mM NaCl, 50 mM Tris pH 7.50, purified CPAF (62.5 nM), fluorescent-tagged model CPAF substrate (0.5 mM), and varying concentrations of each candidate compound (0-240 µM). IC$_{50}$ values were determined by pre-incubating CPAF with varying concentrations of candidate compound for 5 min at room temperature prior to initiation of the reaction via the addition of model CPAF substrate. Reactions were allowed to proceed for 90 seconds at 25° C., followed by removal of 80 µL aliquots and quenching by the addition of 1.2 M HCl (40 µL). Data were converted to percent activity relative to a control reaction without candidate compound and fit to the following equation using GraFit v6.0, where [I] is the concentration of candidate compound and s is a slope factor:

$$\% \text{ Activity} = 100 \left\{ \frac{1}{\left[1 + \left(\frac{[I]}{IC_{50}}\right)^s\right]} \right\}$$

Figure 17:
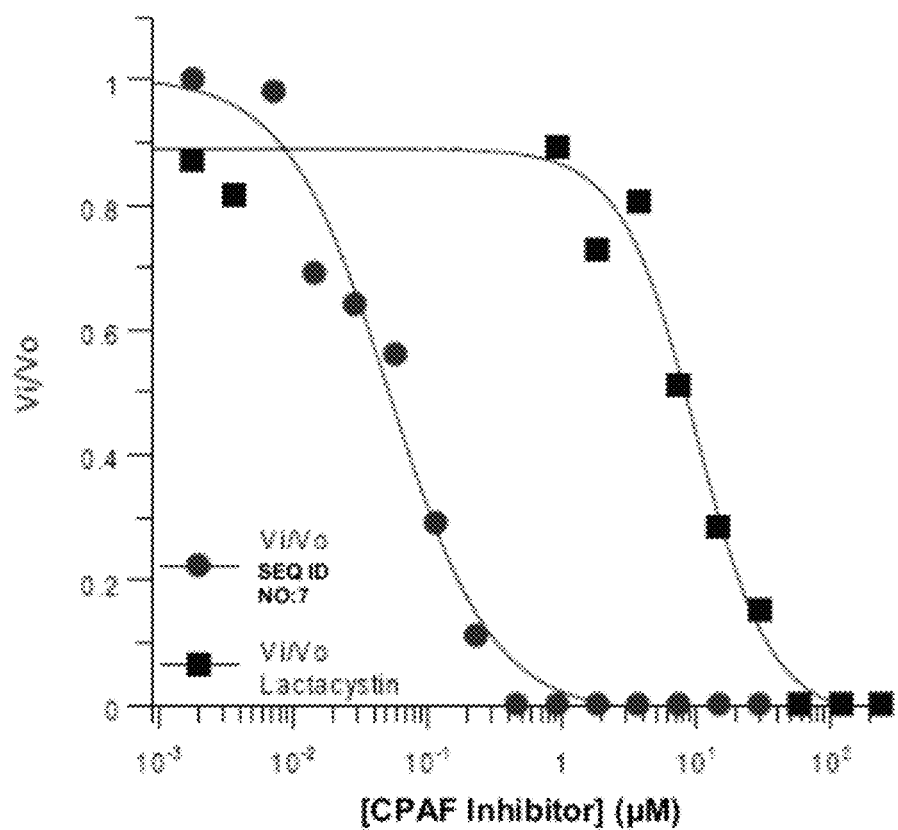
FIG. 17 depicts the results of an HPLC-based CPAF inhibition assay comparing CPAF inhibition by SEQ ID NO:7 peptide and lactacystin. Fluorescence assays were performed as described in a final volume of 100 µL containing assay buffer, CPAF (62.5 nM), SEQ ID NO:9 model CPAF substrate (0.5 mM), and varying concentrations of lactacystin or SEQ ID NO:7 peptide (0-240 µM). The assays produced a calculated $IC_{50}$ value for lactacystin of 10.2±2.3 µM, and a calculated $IC_{50}$ value for the SEQ ID NO:7 peptide of 0.05±0.007 µM.

The HPLC-based assay confirmed lactacystin as an inhibitor of CPAF, with a calculated IC$_{50}$ of 10.2±2.3 µM. Peptides of SEQ ID NO:2 and SEQ ID NO:7 functioned as more potent inhibitors of CPAF, with calculated IC$_{50}$ values of 1.6±0.6 µM and 0.05±0.007 µM, respectively. See FIGS. 1 and 17. SEQ ID NO:7 yielded about 200-fold greater than that of lactacystin and about 30-fold greater than that of SEQ ID NO:2. By analysis of the model of SEQ ID NO: 7 bound to mature CPAF (FIG. 2), the increase in inhibitory activity may be attributed to enhanced binding due to favorable electrostatic interactions between the nona-arginine C-terminus and a large region of electronegative potential proximal to the active site where the helical 25-mer is predicted to bind.

FRET-based assays comprised an Abz-tagged model CPAF substrate with an additional C-terminal 3-nitrotyrosine quencher:

(SEQ ID NO: 10; scissile S-S bond underlined)
Abz-V-R-L-R-<u>S-S</u>-V-P-G-V-(3-NO₃)Tyr-NH₂

Figure 15:
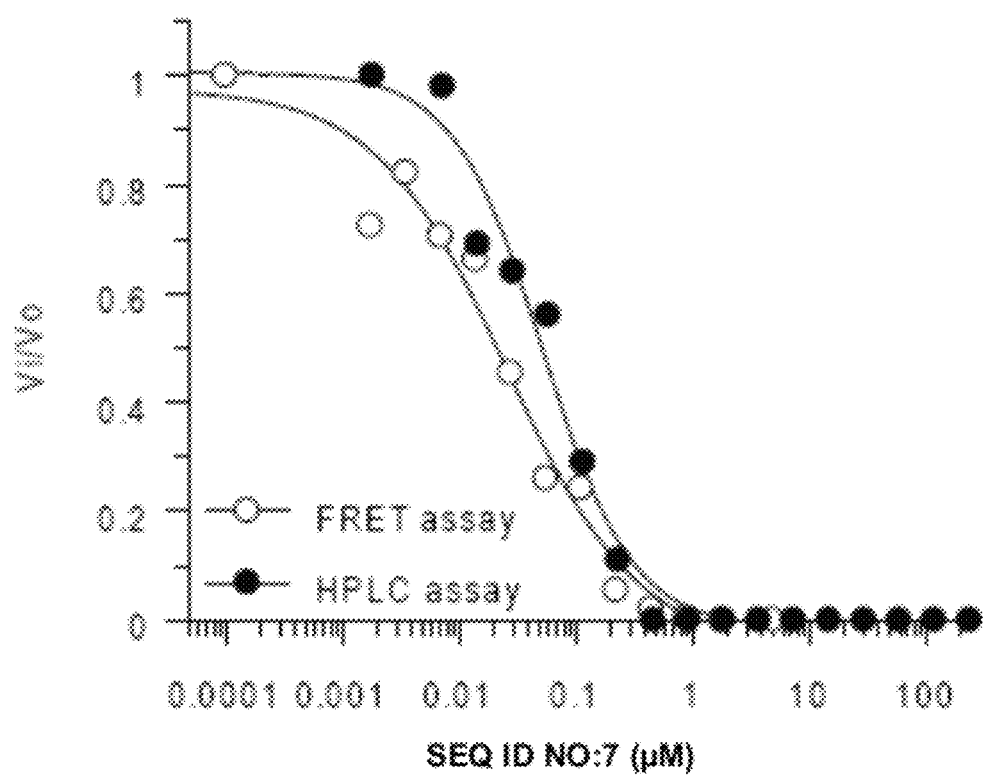
FIG. 15 depicts a comparison of results obtained using embodiments of the disclosed HPLC-based and FRET-based assays for evaluating the inhibition of CPAF activity by a CPAF inhibitor (SEQ ID NO:7). Fluorescence assays were performed in a final volume of 100 µL containing assay buffer, CPAF (62.5 nM), model CPAF substrate (SEQ ID NO:9 for HPCL-based assays and SEQ ID NO:10 for FRET-based assays), and varying concentrations of SEQ ID NO:7 peptide (0-240 µM). The HPLC-based assay yielded an $IC_{50}$ value for the SEQ ID NO:7 peptide of 0.05±0.007 µM, and the FRET-based assay yielded an $IC_{50}$ value of 0.03±0.00 µM.
Figure 16:
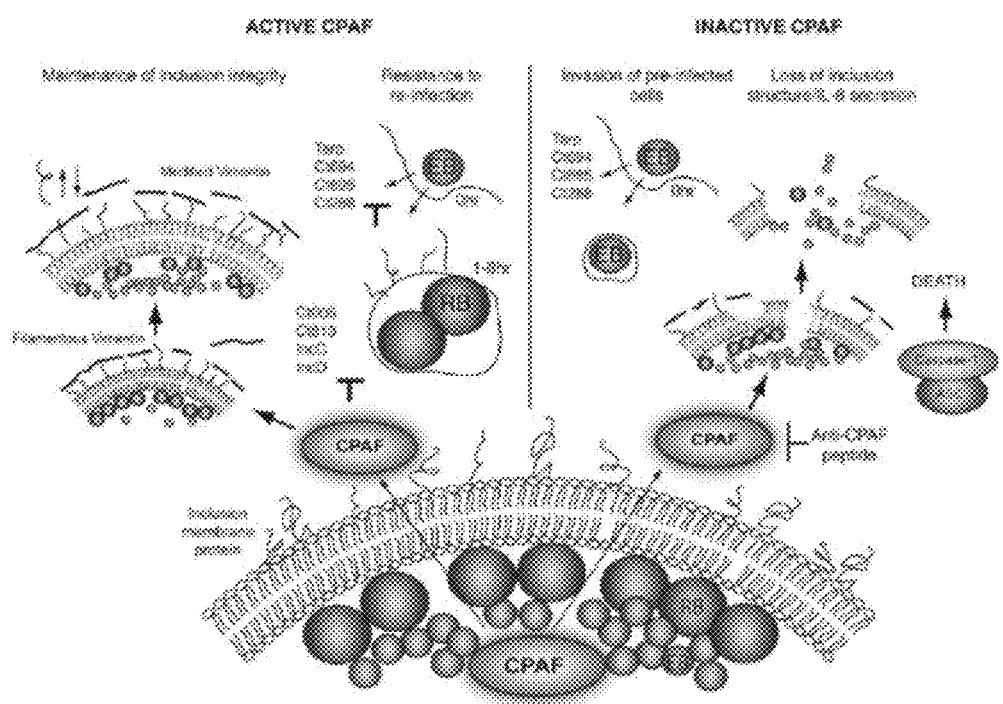
FIG. 16 depicts a schematic model of CPAF as a regulator of early inclusion membrane proteins and inclusion integrity. CPAF reorganizes intermediate filaments at the inclusion periphery to promote inclusion stability. In addition, CPAF mediates the turnover of a subset of inclusion membrane proteins that are expressed early in inclusion biogenesis. Inhibition of CPAF activity leads to a loss of inclusion membrane integrity, hyper-activation of inflammatory cytokines, inflammasome-dependent activation of Caspase-1, and cell death.
Figure 18:
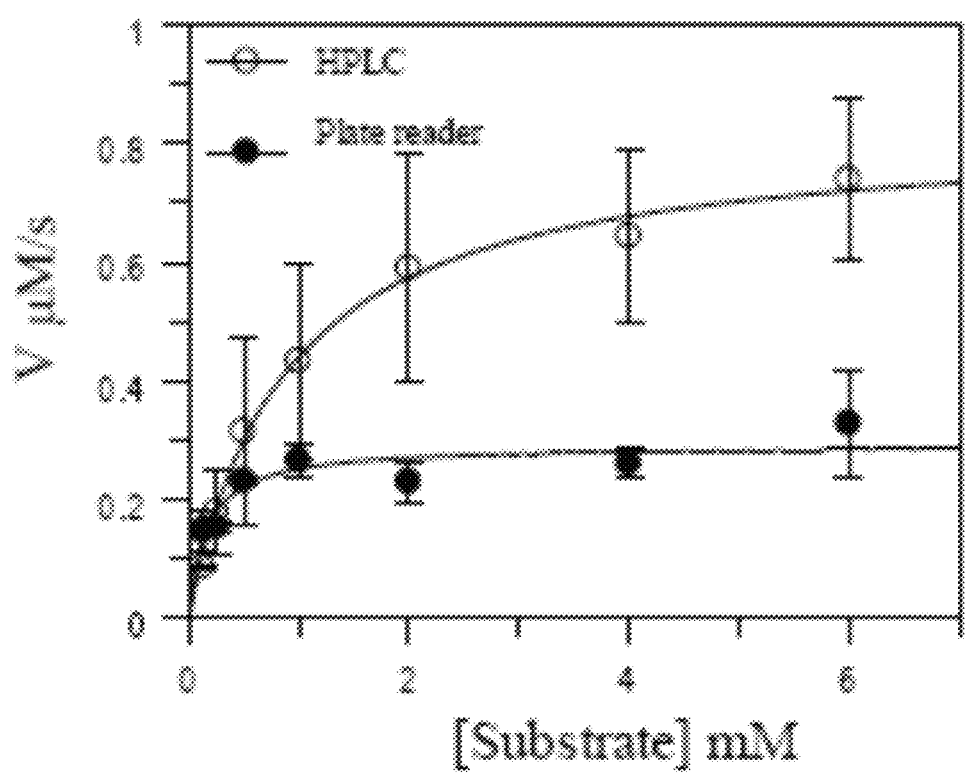
FIG. 18 depicts a comparison between embodiments of the disclosed HPLC-based and FRET-based assays measuring CPAF enzyme activity. Enzyme kinetic parameters for CPAF were determined in parallel using either an HPLC-based assay (with model CPAF substrate of SEQ ID NO:9) or a FRET-based assay (with model CPAF substrate of SEQ ID NO:10). Assays were performed in a total volume of 100 µL containing assay buffer, CPAF (62.5 nM), and varying concentrations of model CPAF substrate (0-6 mM). Due to inter-filter effects when using the FRET-based assay, the resulting Michealis-Menten curve exhibits premature leveling when compared to the curve generated using the HPLC-based assay.

The 3-nitrotyrosine moiety quenches Abz fluorescence until substrate cleavage occurs. FRET-based assays were performed in optical plates in a final volume of 100 µL containing 150 mM NaCl, 50 mM Tris pH 7.50, purified CPAF (62.5 nM), varying concentrations of model CPAF substrate (0.5 mM), and varying concentrations of each candidate compound (0-240 µM). $IC_{50}$ values were determined by pre-incubating CPAF with varying concentrations of candidate compound for 5 min at room temperature prior to initiation of the reaction via the addition of model CPAF substrate. Reactions were initiated and read continuously at 420 nm for 10 minutes using a fluorescence microplate reader. The percentage of substrate converted was calculated using initial velocity over the first 90 seconds and converting RFU to concentration based on a standard curve with Abz followed by analysis in Graffit 6.0 using the equation of Example 8. The FRET-based assay identified peptide of SEQ ID NO:7 as an inhibitor of CPAF, with a calculated $IC_{50}$ value of 0.03±0.006 µM, comparable to the $IC_{50}$ value calculated for SEQ ID NO:7 using the HPLC-based assay. See FIGS. 15 and 18.

---

We claim:

1. An isolated inhibitor of Chlamydial Protease-like Activity Factor (CPAF), wherein the isolated inhibitor consists of SEQ ID NO:2 (SLFYSPMVPHFWAELRNHYATSGLK).

2. An isolated inhibitor of Chlamydial Protease-like Activity Factor (CPAF) wherein the isolated inhibitor consists of SEQ ID NO:6 (SLFYSPMVPHFWAELRNHYATSGLKX$_1$X$_2$X$_3$X$_4$X$_5$X$_6$X$_7$X$_8$X$_9$X$_{10}$), wherein each amino acid X$_1$-X$_{10}$ is optionally absent and each is independently selected from the group consisting of arginine (R), histidine (H), lysine (K), aspartate (D), and glutamate (E).

3. An isolated inhibitor of Chlamydial Protease-like Activity Factor (CPAF) wherein the isolated inhibitor comprises SEQ ID NO:7 (SLFYSPMVPHFWAELRNHYATSGLKRRRRRRRRR).

4. A method of treating a *Chlamydia* infection in a subject in need thereof, comprising administering to the subject an effective amount of the isolated inhibitor of CPAF according to claim 1.

5. A method of treating a *Chlamydia* infection in a subject in need thereof, comprising administering to the subject an effective amount of the isolated inhibitor of CPAF according to claim 2.

6. A method of treating a *Chlamydia* infection in a subject in need thereof, comprising administering to the subject an effective amount of the isolated inhibitor of CPAF according to claim 3.

7. A composition comprising the isolated inhibitor of CPAF according to claim 1, and one or more of a carrier, vehicle, diluent, or adjuvant.

8. A method of treating a *Chlamydia* infection in a subject in need thereof, comprising administering to the subject an effective amount of the composition of claim 7.

9. A method of eliciting an anti-Chlamydia immune response in a subject, comprising administering to the subject an effective amount of the isolated inhibitor of CPAF according to claim 1.

10. A method of inhibiting a *Chlamydia* infection in a cell, comprising contacting the cell with an effective amount of the isolated inhibitor of CPAF according to claim 1.

11. A method of reducing the virulence of a *Chlamydia* infection, comprising contacting a *Chlamydia*-infected cell with an effective amount of the isolated inhibitor of CPAF according to claim 1.

12. A composition comprising the isolated inhibitor of CPAF according to claim 2, and one or more of a carrier, vehicle, diluent, or adjuvant.

13. A composition comprising the isolated inhibitor of CPAF according to claim 3, and one or more of a carrier, vehicle, diluent, or adjuvant.

14. A method of treating a *Chlamydia* infection in a subject in need thereof, comprising administering to the subject an effective amount of the composition of claim 12.

15. A method of treating a *Chlamydia* infection in a subject in need thereof, comprising administering to the subject an effective amount of the composition of claim 13.

* * * * *